US008053629B2

(12) United States Patent
Kasukabe et al.

(10) Patent No.: US 8,053,629 B2
(45) Date of Patent: *Nov. 8, 2011

(54) PLANTS WITH IMPROVED MORPHOGENESIS AND METHOD OF CONSTRUCTING THE SAME

(75) Inventors: Yoshihisa Kasukabe, Otsu (JP); Izumi Ihara, Otsu (JP); Shoji Tachibana, Age-gun (JP); Keisuke Matsui, Osaka (JP); Masako Mizutani, Kyoto (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 435 days.

This patent is subject to a terminal disclaimer.

(21) Appl. No.: 12/239,117

(22) Filed: Sep. 26, 2008

(65) Prior Publication Data

US 2009/0100546 A1    Apr. 16, 2009

Related U.S. Application Data

(63) Continuation of application No. 10/926,450, filed on Aug. 26, 2004, now Pat. No. 7,446,242, which is a continuation-in-part of application No. PCT/JP03/04427, filed on Apr. 8, 2003.

(30) Foreign Application Priority Data

Apr. 8, 2002 (JP) ................................. 2002-105583

(51) Int. Cl.
*C12N 15/82* (2006.01)
(52) U.S. Cl. .......................... 800/278; 800/287; 800/290
(58) Field of Classification Search .......................... None
See application file for complete search history.

(56) References Cited

U.S. PATENT DOCUMENTS

| | | | | |
|---|---|---|---|---|
| 5,831,060 | A | 11/1998 | Wada et al. | |
| 6,297,429 | B1 | 10/2001 | Takatsuji et al. | |
| 7,238,861 | B2 * | 7/2007 | Kasukabe et al. | 800/289 |
| 7,446,242 | B2 * | 11/2008 | Kasukabe et al. | 800/290 |
| 7,888,554 | B2 | 2/2011 | Kasukabe et al. | |
| 2003/0163851 | A1 | 8/2003 | Kasukabe et al. | |
| 2005/0150015 | A1 | 7/2005 | Kasukabe et al. | |
| 2008/0010702 | A1 | 1/2008 | Kasukabe et al. | |
| 2009/0100547 | A1 | 4/2009 | Kasukabe et al. | |
| 2010/0083401 | A1 | 4/2010 | Kasukabe et al. | |

FOREIGN PATENT DOCUMENTS

| | | |
|---|---|---|
| JP | 10-4978 | 1/1998 |
| JP | 11-262390 | 9/1999 |
| JP | 2000-270873 | 5/2000 |
| JP | 2000-290102 | 10/2000 |
| JP | 2001-46079 | 2/2001 |
| WO | WO 00/67558 A1 | 11/2000 |
| WO | WO 01/09358 A1 | 2/2001 |
| WO | WO 01/11062 A2 | 2/2001 |
| WO | WO 02/18547 A1 | 3/2002 |
| WO | WO 02/23974 A1 | 3/2002 |
| WO | WO 200223974 * | 3/2002 |
| WO | WO 2003/084314 A1 | 10/2003 |
| WO | WO 2006/057306 A1 | 6/2006 |

OTHER PUBLICATIONS

Yamanoha et al (1984, Journal of Biochemistry 96(4):1273-1281; abstract only).*
Yamanoha et al (1984, Journal of Biochemistry 96(4):1273-1281).*
Kumar et al., *Trends in Plant Science*, 2(4): 124-130 (Apr. 1, 1997).
Arif et al., *Plant Molecular Biology*, 26: 327-338 (1994).
Bagni et al., "Polyamines and Morphogenesis in Normal . . . Cultures" in *Morphogenesis in Plants* (Plenum Press), pp. 89-111 (1993).
Bell et al., *Mol. Gen. Genet.*, 224: 431-436 (1990).
Bolle et al., *Plant Physiol.*, 107: 1461-1462 (1995).
Bouchereau, *Plant Science*, 140(2): 103-125 (1999).
Bowie et al., *Science*, 247: 1306-1310 (1990).
Burtin et al., *Biochem J.*, 325: 331-337 (1997).
Capell et al., *Mol. Gen. Genet.*, 264(4): 470-476 (2000).
Capell et al., *Theor. Appl. Genet.*, 97(1-2): 246-254 (1998).
Carbonell et al., *Plant Molecular Biology*, 39(5): 933-943 (1999).
Franceschetti et al., *Biochemical J.*, 353: 403-409 (2001).
Fujihara et al., *Physiologia Plantarum*, 113: 416-423 (2001).
Galston et al., *Plant Physiology*, 94: 406-410 (1990).
Hanfrey et al., *J. Biol. Chem.*, 277(46): 44131-44139 (2002).
Hanzawa et al., *The EMBO Journal*, 19(16): 4248-4256 (2000).
Hare et al., *Physiologia Plantarum*, 91: 128-136 (1994).
Hashimoto et al., *Plant Cell Physiol.*, 39(1): 73-79 (1998).
Hatanaka et al., *Plant Science*, 140: 161-168 (1990).
Kakkar et al., *Biologia Plantarum*, 43(1): 1-11 (2000).
Kakkar et al., *Phytochemistry*, 33(6): 1281-1288 (1993).
Kasukabe et al., *19th Biotechnology Symposium Abstracts*, 19: 31-34 (2001).
Kasukabe et al., *19th Biotechnology Symposium Abstracts*, 19: 216-219 (2001).
Kasukabe et al., *Biotechnology Symposium Abstracts*, 18: 310-313 (2000).
Kumar et al., *The Plant Journal*, 9(2): 147-158 (1996).
Lee et al., *Plant Science*, 122: 111-117 (1997).
Marco et al., *Planta*, 214: 641-647 (2002).
Masgrau et al., *The Plant Journal*, 11(3): 465-473 (1997).
Mcconnell et al., *Nature*, 411(6838): 709-713 (2001).
Michael et al., *Biochem J.*, 314: 241-248 (1996).
Noh et al., *Transgenic Research*, 3: 26-35 (1994).
Noury et al., *Plant Molecular Biology*, 43: 537-544 (2000).
Pedros et al., *Planta*, 209: 153-160 (1999).
Perez-Amador et al., *Plant Molecular Biology*, 28: 997-1009 (1995).
Poster Sessions—Abstracts, *Plant Physiol.*, 114(3): 297 (1997).
Raney et al., *J. Biol. Chem.*, 277(8): 5988-5994 (2002).
Rastogi et al., *Plant Physiol.*, 103: 829-834 (1993).
Rorat et al., *Plant Science*, 124(1): 69-78 (1997).
Roy et al., *Plant Science*, 160: 869-875 (2001).
Tachibana, *Chemical Regulation of Plant*, 35(1): 56-66 (2000).

(Continued)

*Primary Examiner* — Stuart F. Baum
(74) *Attorney, Agent, or Firm* — Leydig, Voit & Mayer, Ltd.

(57) ABSTRACT

The invention relates to plants and their progeny with improved morphogenesis in a variety of organs; to a method for producing the plants; and to a method for producing calli.

5 Claims, 15 Drawing Sheets

OTHER PUBLICATIONS

Tassoni et al., *Plant Physiology & Biochemisty*, 38(5): 383-393 (2000).
Walden et al., *Plant Physiol.*, 113: 1009-1013 (1997).
Watson et al., *Plant Physiol.*, 111: 1077-1083 (1996).
Watson et al., *The Plant Journal*, 13(2): 231-239 (1998).
Wi et al., *Plant Biology*, 41(390): 41 (1999).
Fengzhi et al., *Journal of Agricultural University of Hebei*, 19(3): 94-98 (1996).
Sharma et al., *J. Agronomy & Crop Science*, 181: 189-191 (1998).
Alabadi et al., "Molecular Cloning and Characterization of a Tomato Spermidine Synthase cDNA (Accession No. AJ006414)" [Plant Gene Register PGR 99-103], *Plant Physiology*, 120: 933-935 (1999).
Alabadi et al., *Plant Molecular Biology*, 39: 933-943 (1999).
Apse et al., *Science*, 285: 1256-1258 (1999).
Aziz et al., *Physiologia Plantarum*, 104: 195-202 (1998).
Bastola et al., *Plant Physiol.*, 109: 63-71 (1995).
Broglie et al., *Science*, 254: 1194-1197 (1991).
De La Fuente et al., *Science*, 276: 1566-1568 (1997).
Descenzo et al., *Plant. Molecular Biology*, 22: 113-127 (1993).
Erdei et al., *J. Plant Physiol.*, 147: 599-603 (1996).
Flores et al., *Plant Physiol.*, 75: 102-109 (1984).
Galston et al., *Botanica Acts.*, 110(3): 197-207 (1997).
Guo et al., *Proc. Natl. Acad. Sci.*, 101(25): 9205-9210 (Jun. 22, 2004).
Keskin et al., *Protein Science*, 13: 1043-1055 (2004).
Krishnamurthy et al., *Plant Physiol.*, 91: 500-504 (1989).
Kurepa et al., *Plant Cell Physiol.*, 39(9): 987-992 (1998).
Mad Arif et al., *Plant Molecular Biology*, 26: 327-338 (1994).
Maniatis et al., *Molecular Cloning: A Laboratory Manual, Cold Spring Harbor Laboratory* (1982), pp. v-x, 324-343, and 387-389.
Minocha, *Plant Physiology*, 114(3—Suppl.): 297, Abstract 1552 (1997).
Murakami et al., *Science*, 287: 476-479 (2000).
Murata et al., *Nature*, 356(23): 710-713 (1992).
Nam et al., *Plant Cell Physiol.*, 38(10): 1156-1166 (1997).
Ngo et al., "Computational Complexity, Protein Structure Prediction, and the Levinthal Paradox" in *The Protein Folding Problem and Tertiary Structure Prediction*, K. Merz and S. Le Grand (eds), pp. 492-495 (Birkhauser, Boston, 1994).
Prakash et al., *Austr. J. Plant Physiol.*, 15: 761-767 (1998).
Rajam et al., *J. Biosci.*, 23(4): 473-482 (Oct. 1998).
Shah et al., *Science*, 233: 478-481 (1986).
Shen et al., *Journal of the Japanese Society for Horticultural Science*, 68(4): 780-787 (1999).
Shen et al., *Journal of the Japanese Society for Horticultural Science*, 68(5): 967-973 (Sep. 1999).
Shen et al., *Plant Physiol.*, 124: 431-439 (2000).
Thornton et al., *Nature Structural Biology, Structural Genomics Supplement*: 991-994 (Nov. 2000).
Torrigiani et al., *New Phytol.*, 135: 467-473 (1997).
Valvekens et al., *Proc. Natl. Acad. Sci. USA*, 85: 5536-5540 (Aug. 1988).
Wells, *Biochemistry*, 29(37): 8509-8517 (1990).
Wen et al., *Transgenic Research*, DOI 10.1007/s11248-007-9098-7, 13 pages (published on-line on Jun. 5, 2007).
Wen et al., *Transgenic Research*, 17(2): 251-263 (2008).
Wi et al., *Plant Biology*, 2000: 108, Abstract 485 (2000).
Yoder et al., *Biotechnology*, 12: 263-267 (1994).
Yoza et al., *Food Science and Technology*, 37: 59-76 (1998).
Zhang et al., "Structure and expression of spermidine synthase genes in apple: two cDNAs are spatially and developmentally regulated through alternative splicing," *Mol. Gen. Genomics*, 268: 799-807 (2003).

\* cited by examiner 1. pBI101-35S-SPDS(+)-Hm2

2. pBI101-35S-SPDS(-)-Hm2

ANALYSIS OF THE NUMBER OF FLOWER STEMS OF ARABIDOPSIS THALIANA

ANALYSIS OF THE NUMBER OF MAIN FLOWER STEMS OF ARABIDOPSIS THALIANA
COMPARISON OF WILD TYPE PLANT AND HOMOTRANSGENIC PLANT

ANALYSIS OF THE NUMBER OF SIDE FLOWER STEMS OF ARABIDOPSIS THALIANA
COMPARISON OF WILD TYPE PLANT AND HOMOTRANSGENIC PLANT

COMPARISON OF DAYS TO BLOOMING OF WILD TYPE PLANTS AND TRANSGENIC PLANTS

WT          TSP

Free polyamine content in leaves

Free polyamine content in tuberous roots

PLANTS WITH IMPROVED MORPHOGENESIS AND METHOD OF CONSTRUCTING THE SAME

CROSS-REFERENCE TO RELATED APPLICATION

This patent application is a continuation of U.S. patent application Ser. No. 10/926,450, filed on Aug. 26, 2004, now U.S. Pat. No. 7,446,242, which is a continuation-in-part application of PCT/JP03/04427, filed on Apr. 8, 2003 designating the United States, under 35 U.S.C. §§120 and 363, which claims the benefit of Japanese Patent Application No. 2002-105583 filed on Apr. 8, 2002, which priority is hereby claimed as set forth under 35 U.S.C. §365(b), all of which patent applications are incorporated by reference herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 35,763 bytes ASCII (Text) file named "703502SequenceListing.TXT," created on Sep. 22, 2008.

TECHNICAL FIELD

The present invention relates to plants with various types of improved morphogenesis, in particular to plants with morphogenetically improved stems, leaves, flowers, ovaries (pods, fruit), roots, tubers, tuberous roots and seeds. The present invention further relates a method of producing such plants.

BACKGROUND ART

Plants adapt to various types of environmental factors of their roots. For example, plants have a capacity to change shapes corresponding to the environment of growth and development. Once a plant has sent down roots in a given place, if the environment of that place somehow becomes unsuitable to that plant, the plant cannot move, but adapts and continues to grow and develop by changing its own shape. The ability to change shapes is an essential condition of survival for a plant.

Cross-breeding, breeding using recent genetic engineering techniques, and methods utilizing the action of plant hormones and plant regulators have been implemented in order to improve various types of morphological modification.

Numerous studies have been conducted using *Arabidopsis thaliana* in order to understand the control mechanisms of the morphogenesis and morphological modification of plants. There have been reports of LEAFY (LFY), APETALA1 (AP1), AGAMOUS (AG), SUPERMAN(SUP) and FIL (FIL) as genes that participate in flower formation. There have been reports of TCH4 and dbp, etc. as genes that participate in stem formation. There have been reports of LAN1 and MAC as genes that participate in leaf formation. There have been reports of ttg, g12, CPC and IRE as genes that participate in root formation.

Plants with improved morphological modification and morphogenesis have already been created using genetic engineering techniques. There have been reports of morphological changes of the flowers of petunia by introducing a transcription factor (PetSPL3) having a zinc finger motif (Japanese Enexamined Patent Publication No. 262390/1999). There have been reports of morphological changes of the roots of *Arabidopsis thaliana* by introducing a CPC gene or an IRE gene (Japanese Enexamined Patent Publication No. 4978/1998, Japanese Enexamined Patent Publication No. 270873/2000). However, most plants in which these genes have been transgenetically modified have not actually obtained sufficient effect to have industrial applicability, and currently a practical level has not yet been reached.

Polyamines, the general term for aliphatic hydrocarbons with 2 or more primary amino groups, are ubiquitous natural substances in organisms, with more than 20 types discovered so far. Typical polyamines include putrescine, spermidine, and spermine. The known primary physiological action of polyamines includes (1) nucleic acid stabilization and structural modification through interaction with nucleic acids; (2) promotion of various nucleic acid synthesis systems; (3) activation of protein synthesis systems; and (4) stabilization of cell membranes and enhancement of membrane permeability of substances.

Reports on the role of polyamines in plants include cell protection and promotion of nucleic acid or protein biosynthesis during cellular growth or division. The involvement of polyamines in various types of environmental stress has recently attracted attention.

There have been several reports on morphological modification and polyamine relating to somatic embryogenesis and adventitious root formation. For example, it has been demonstrated that polyamine promotes somatic embryogenesis in carrots (Planta, 162, 532, 1984, Science, 223, 1433, 1984), oats (Plant Growth Reg., 3, 329, 1985), Chinese cabbage (Plant Sci., 56, 167, 1988), and petunia (Plant Sci., 62, 123, 1989), and promotes adventitious root formation in mung beans (Physiol. Plant., 64, 53, 1985, Plant Cell Physiol., 24, 677, 1983). Thus far, there have been hardly any reports on the participation of polyamine in the morphogenesis of flowers, stems, leaves, and ovaries.

Known polyamine metabolism-related enzymes involved in the biosynthesis of plant polyamines include arginine decarboxylase (ADC), ornithine decarboxylase (ODC), S-adenosylmethionine decarboxylase (SAMDC), spermidine synthase (SPDS), and spermine synthase (SPMS). Several polyamine metabolism-related enzyme genes coding for such polyamine metabolism-related enzymes have already been isolated from plants. The ADC gene has been isolated from oats (Mol. Gen. Genet., 224, 431-436 (1990)), tomatoes (Plant Physiol., 103, 829-834 (1993)), *Arabidopsis thaliana* (Plant Physiol., 111, 1077-1083 (1996)), and peas (Plant Mol. Biol., 28, 997-1009 (1995)); the ODC gene has been isolated from datura (Biochem. J., 314, 241-248 (1996)); the SAMDC gene has been isolated from potatoes (Plant Mol. Biol., 26, 327-338 (1994)), spinach (Plant Physiol., 107, 1461-1462 (1995)), and tobacco; and the SPDS gene has been isolated from *Arabidopsis thaliana* (Plant Cell Physiol., 39(1), 73-79 (1998)).

Thus, an object of the present invention is to produce recombinant plants with various types of improved morphogenesis by artificially controlling the expression of polyamine metabolism-related enzyme genes, and by varying the polyamine levels.

BRIEF DESCRIPTION OF THE INVENTION

FIG. 1 indicates the structure of an expression construct containing a polyamine metabolism-related enzyme gene;

FIG. 2 indicates the results of expression of the *Cucurbita ficifolia* Bouche SPDS gene in transformants. In FIG. 2, 1. wild type (WT); 2. transformant (TSP-14); 3. transformant (TSP-15); 4. transformant (TSP-16); 5. transformant (TSP-17); 6. transformant (TSP-19).

FIG. 3 indicates a comparison of the number of stems of a wild type plant and of a plant in which a polyamine metabolism-related enzyme gene has been introduced;

Figure 8:
Figure 9:
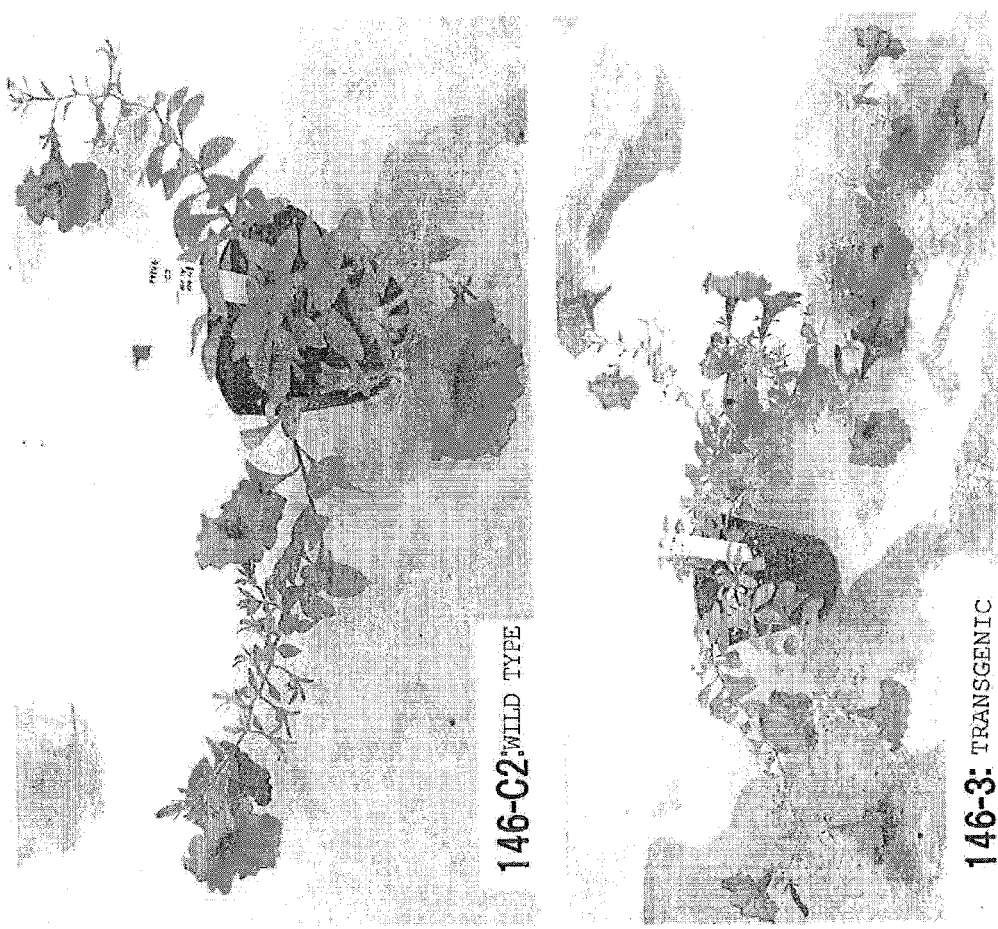

FIG. 8 indicates the results of measuring the changes over time in the number of flowers per individual for an individual plant expressing a foreign gene; and FIG. 9 indicates the results of measuring the changes over time in the number of flowers per individual for individual expressing a foreign gene.

Figure 10:
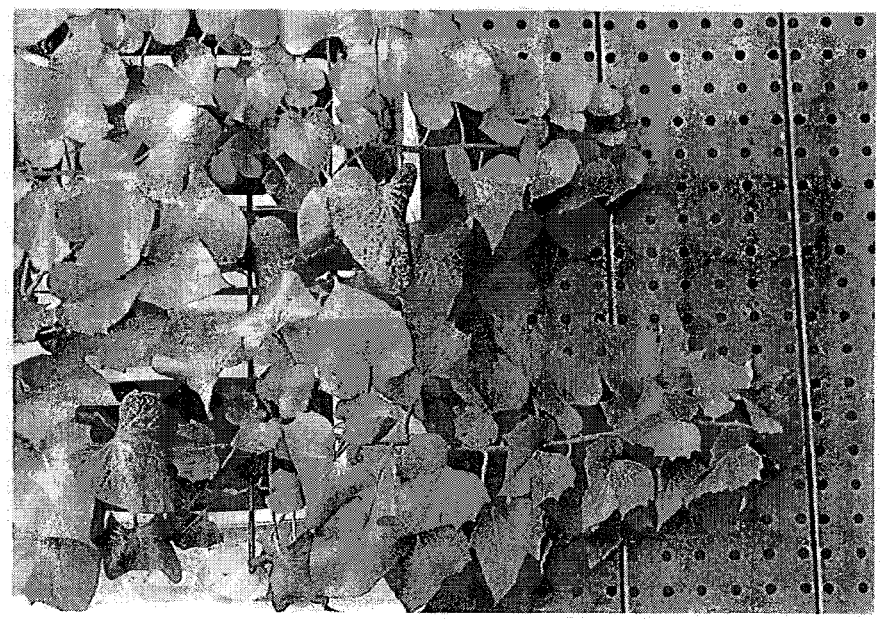
Figure 10:
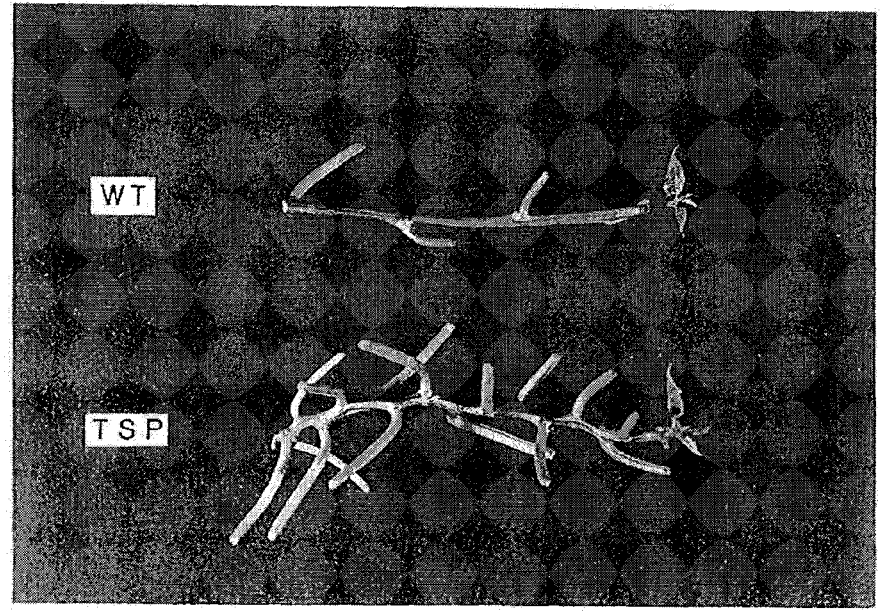

FIG. 10 indicates a comparison of stems, leaves and vines of wild type sweet potatoes and of transgenic sweet potatoes into which a polyamine metabolism-related enzyme gene is introduced.

Figure 11A:
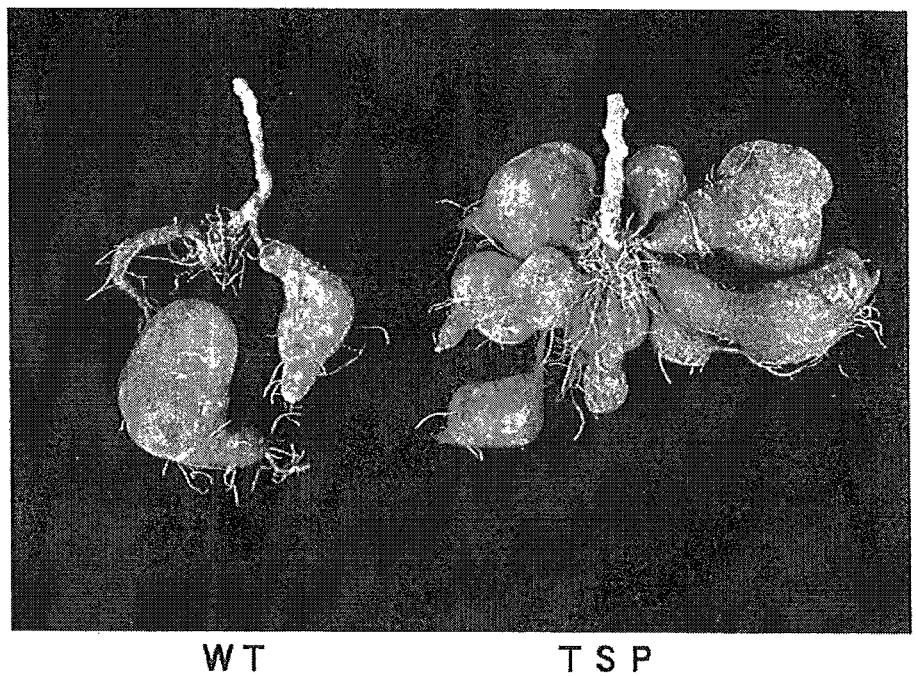
Figure 11A:
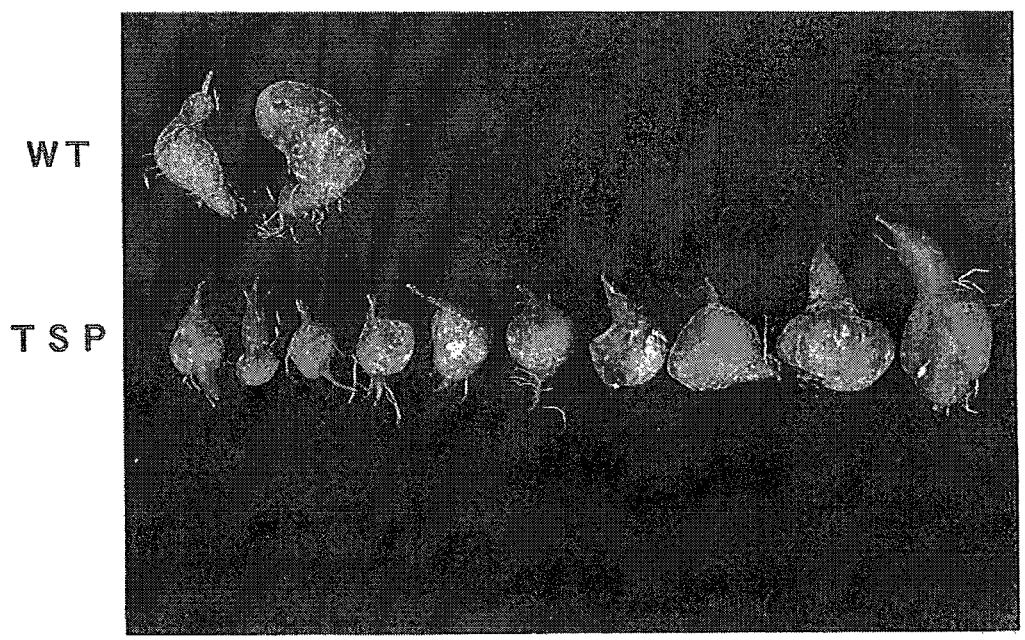
Figure 11B:
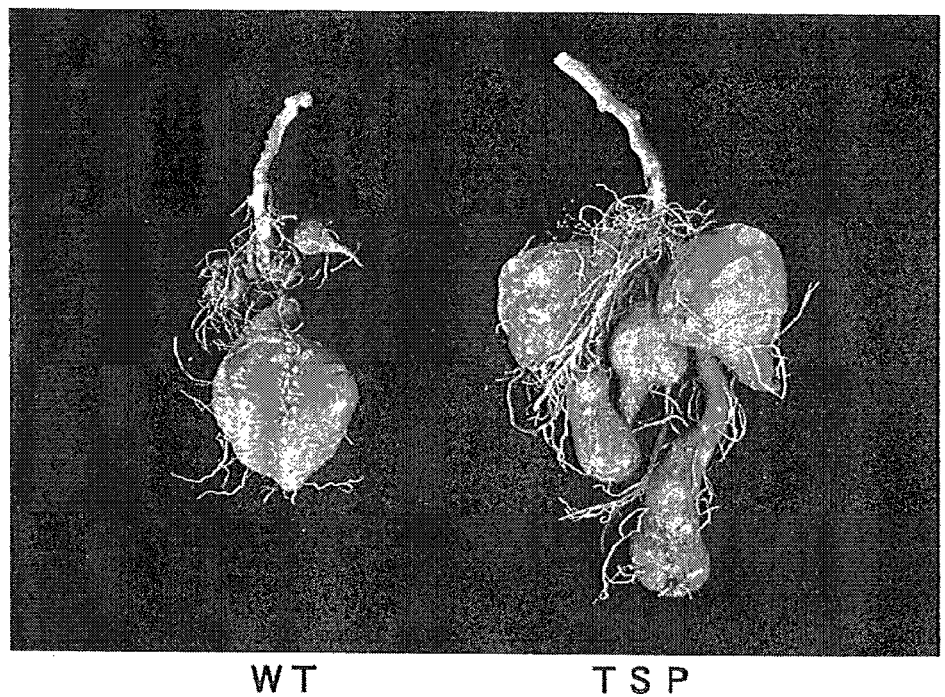
Figure 11B:
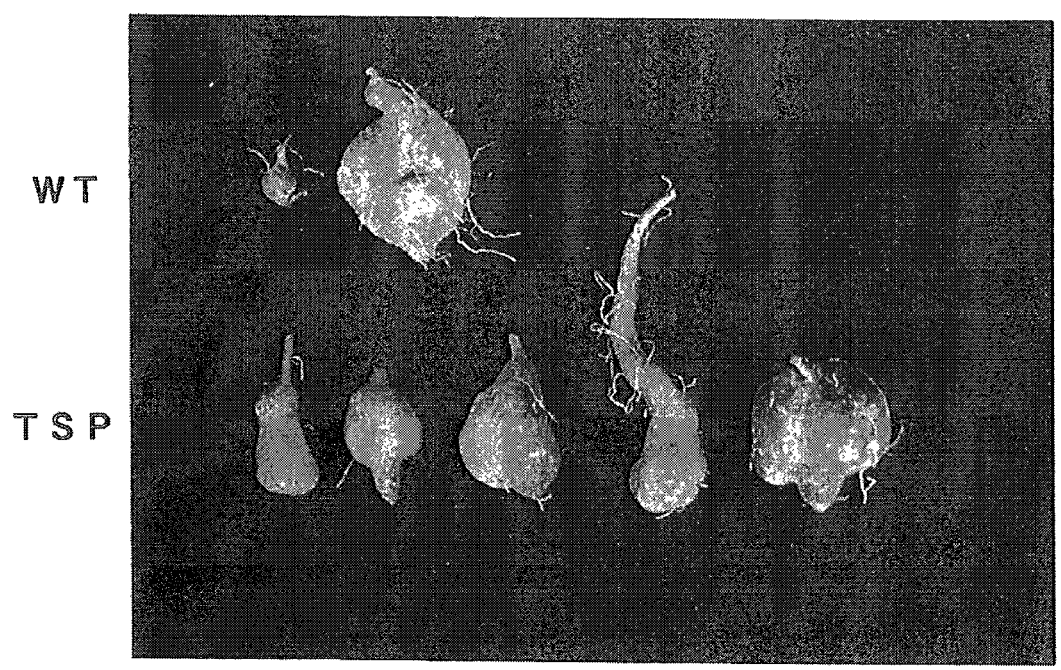

FIGS. 11A and 11B indicate a comparison of roots (tuberous roots) of wild type sweet potatoes and of transgenic sweet potatoes into which a polyamine metabolism-related enzyme gene is introduced.

Figure 12:
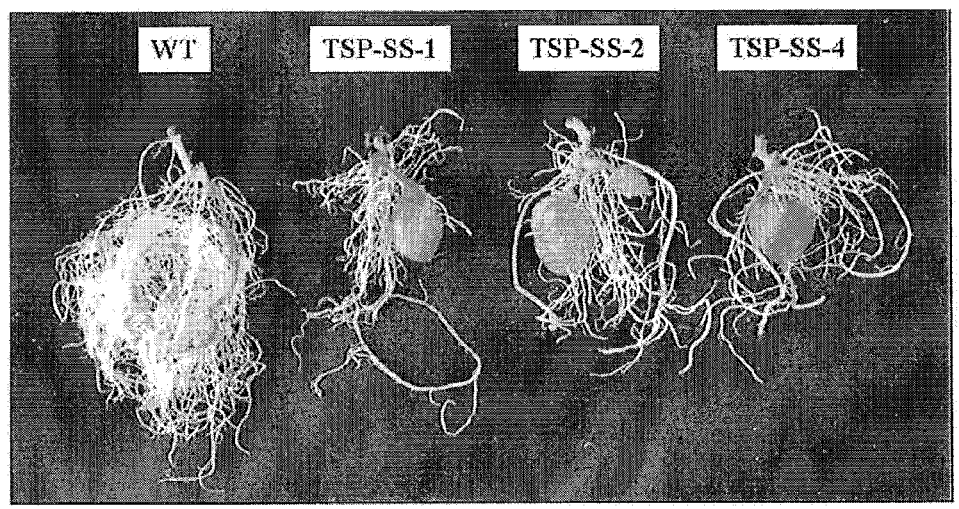

FIG. 12 indicates a comparison of roots of wild type sweet potatoes and transgenic sweet potatoes into which a polyamine metabolism-related enzyme gene is introduced, which are cultivated under moderately stressful condition.

Figure 13:
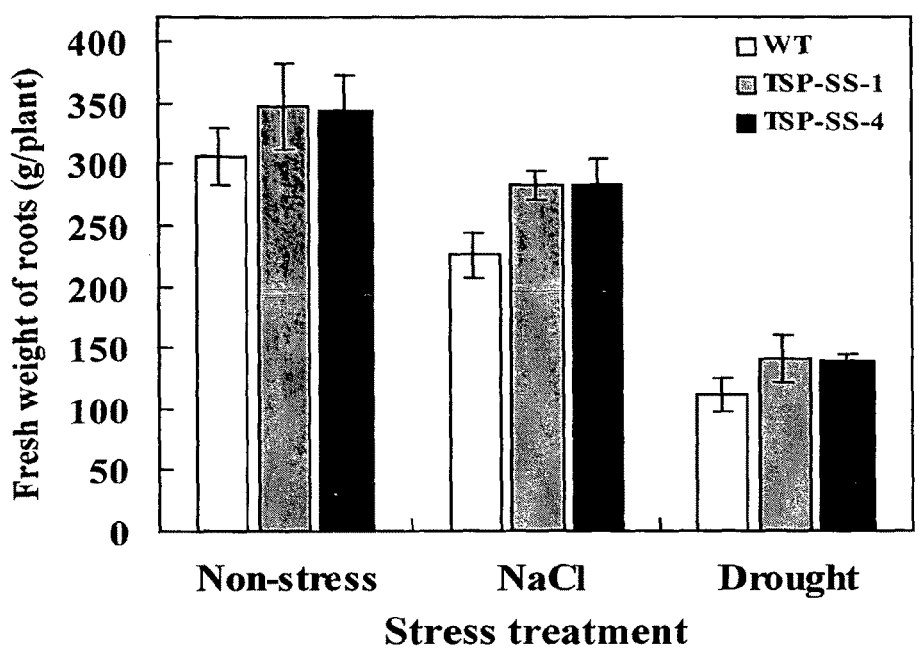

FIG. 13 indicates a comparison of fresh weight of tuberous roots of wild type sweet potatoes and of transgenic sweet potatoes to which a polyamine metabolism-related enzyme gene is introduced, which are cultivated under non-stress, salt stress or drought stress conditions.

Figure 14:
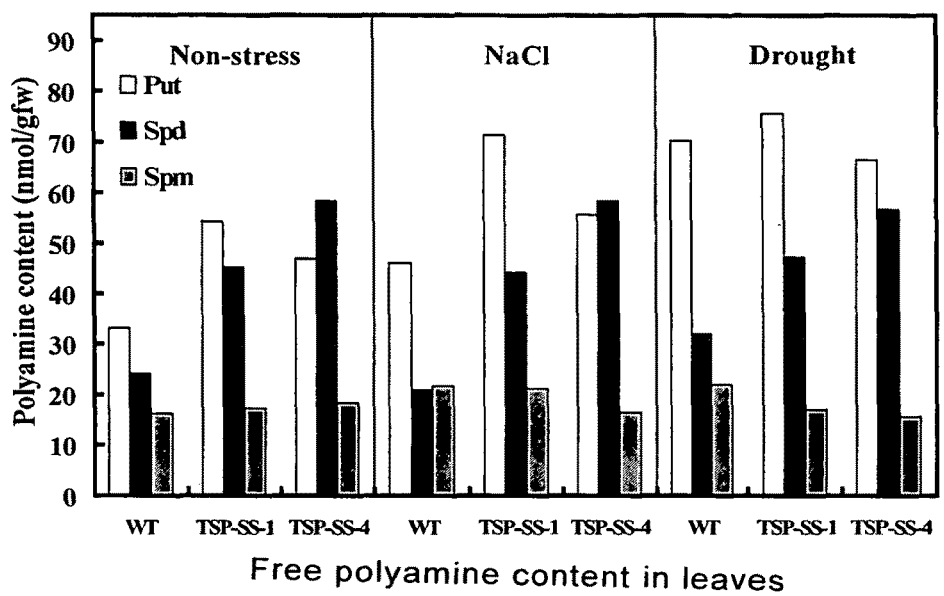
Figure 14:
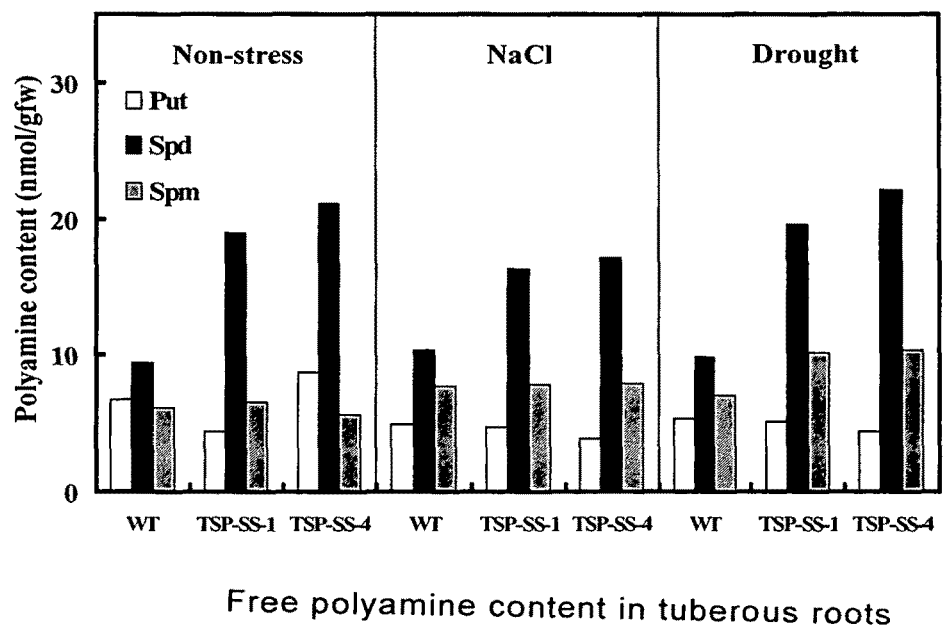

FIG. 14 indicates a comparison of polyamine content in leaves and tuberous roots of wild type sweet potatoes and of transgenic sweet potatoes into which a polyamine metabolism-related enzyme gene is introduced, which are cultivated under non-stress, salt stress or drought stress conditions.

DISCLOSURE OF THE INVENTION

As a result of extensive research to achieve the aforementioned objects, the inventors discovered that various parameters of morphogenesis, such as stems, leaves, flowers, ovaries (pods, fruit) and seeds (ovule) are improved when polyamine metabolism-related enzyme genes involved in polyamine biosynthesis are isolated and are introduced and overexpressed in plants so as to bring about changes in the polyamine level through the manipulation of polyamine metabolism.

Polyamines are basic substances containing an abundance of amines per molecule, typical examples of which include the diamine putrescine, the triamine spermidine, and the tetraamine spermine. Examples of polyamine metabolism-related enzymes involved in the biosynthesis of such polyamines include ADC and ODC for putrescine, SAMDC and SPDS for spermidine, and SAMDC and SPMS for spermine. Polyamine metabolism-related enzyme genes coding for such polyamine metabolism-related enzymes have already been insolated in several plants. Further, some polyamine metabolism-related enzyme genes are incorporated in plants. However, there have been no reports on improved morphogenesis of stems, leaves, flowers, ovaries, roots, tubers, tuberous roots and seeds of the resulting transgenic plants.

As a result of extensive research in view of the foregoing to improve the morphogenesis of plants, the inventors discovered that the content of the polyamines spermidine and spermine, in particular, is important for morphogenesis in plant. The inventors actually isolated and identified polyamine metabolism-related enzyme genes (SPDS, SAMDC, ADC) involved in spermidine and spermine biosynthesis from plant tissue. The inventors perfected the present invention upon discovering that the introduction and over-expression of these genes in plants brought about changes in the polyamine level through the manipulation of polyamine metabolism, leading to improvement of various morphogenesis parameters with respect to stems, leaves, flowers, ovaries (pods, fruit), roots, tubers, tuberous roots and seeds (ovules).

The present invention is intended to provide the following.

1. Plants and their progeny, which stably retain at least one nucleic acid sequence modulating an amount of one or more polyamines under the control of one or more promoters capable of functioning in plants, and the plants and their progeny have at least one kind of improved morphogenesis compared to the plant lacking said nucleic acid sequence.

22. A method for producing plants that stably retains at least one nucleic acid sequence modulating an amount of one or more polyamines under the control of one or more promoters that can function within the plant, and that has improved morphogenesis compared to the plant lacking said nucleic acid sequence, comprising the step of transforming the cells of a plant lacking said nucleic acid sequence.

24. A method for producing plants with improved morphogenesis compared to plants lacking a nucleic acid sequence modulating an amount of one or more polyamines, comprising the step of transforming cells of a plant lacking said nucleic acid sequence with at least one expression vector containing at least one said nucleic acid sequence under the control of one or more promoters capable of functioning in plants.

40. A method for producing a plant with fixed traits, which is a homozygote with respect to a nucleic acid sequence modulating an amount of one or more polyamines and which has improved morphogenesis compared to plants lacking said nucleic acid sequence, comprising the steps of:

(1) transforming cells of a plant lacking said nucleic acid sequence with at least one expression vector containing at least one said nucleic acid sequence under the control of one or more promoters capable of functioning in plants;

(2) regenerating plants with improved morphogenesis compared to plants lacking said nucleic acid sequence from the transformed cells;

(3) harvesting seeds by pollination from the plant bodies; and (4) assaying the nucleic acid sequence in the seeds obtained by pollination from the plant bodies, which have been obtained by cultivation of the seeds so as to select a homozygote with respect to the nucleic acid sequence.

41. A method for producing calli with fixed traits, which is a homozygote with respect to a nucleic acid sequence modulating an amount of one or more polyamines and which has improved morphogenesis compared to plants lacking said nucleic acid sequence, comprising the steps of:

(1) transforming cells of a plant lacking said nucleic acid sequence with at least one expression vector containing at least one inhibitor of the nucleic acid sequence under the control of one or more promoters capable of functioning in plants; and (2) inducing calli from the transformed cells.

42. The method according to any of items 22 to 41, wherein the plant with improved morphogenesis is a root and tuber crop.

43. The method according to item 42, wherein the tuber plant is a sweet potato plant.

44. A method for producing tubers or tuberous roots having an improved morphogenesis independent of presence or absence, or degree of environmental stress compared to reference tubers or tuberous roots comprising the steps of:

(1) cultivating one or more root and tuber crops obtained by the method of item 42; and (2) harvesting tubers or tuberous roots.

45. A method for producing one or more useful substances by separating one or more useful substances from the plants and their progeny according to any one of items 1 to 19 or the plant obtained from the method according to any one of items 22 to 40.

46. A method for producing starch from tubers or tuberous roots comprising the steps of:

(1) cultivating one or more root and tuber crops obtained by the method of item 42 to harvest tubers or tuberous roots; and (2) separating starch from the resulting one or more root and tuber crops.

47. A method for producing biodegradable plastic comprising the steps of (1) cultivating one or more root and tuber crops obtained by the method of item 42 to harvest tubers or tuberous roots;

(2) separating starch from the resulting tubers or tuberous roots; and (3) converting the starch to biodegradable plastic.

48. The method according to item 47, wherein said biodegradable plastic is polylactic acid.

According to the invention, "organ" means all organs (tissues) of the plant, and indicates, for example, stems, tubers, leaves, roots, tuberous roots, buds, flowers, petals, ovaries, fruit, pods, capsules, seeds, fibers and ovules, etc. The traits relating the form of the organ (tissue) may be of the quantity, the growth and development period, shape, color, properties, and characteristics, etc. Because the amount of expression of polyamine closely relates to the quantity of organs, increase of polyamines advances the beginning and delays the end of growth and development with respect to leaves, flowers, fruit, roots, tubers, tuberous roots, pods and capsules, these can be appreciated and enjoyed for an extended period.

The amount of expression of polyamine in a plant obtained by the present invention may be increased without being influenced by the growing environment (for example environmental stress), and can improve morphogenesis.

Exogenous polyamine metabolism-related enzyme genes or inhibitors of endogenous polyamine metabolism-related enzyme genes may be cited as nucleic acid sequences that modulate the amount of polyamines. Exogenous polyamine metabolism-related enzyme genes increase the amount of polyamine in the plant, and inhibitors of endogenous polyamine metabolism-related enzyme genes reduce the amount of polyamine in the plant.

With respect to the present invention, "plants that do not have the nucleic acid sequence to modulate the amount of polyamine" means all plants that do not have in the genome the nucleic acid sequence (for example, exogenous polyamine metabolism-related enzyme genes or inhibitors of endogenous polyamine metabolism-related enzyme genes). Consequently, in addition to wild-type varieties, this encompasses cultivars established by ordinary cross-breeding, natural or artificial mutants, and transgenic plants in which exogenous genes other than polyamine metabolism-related enzyme genes have been introduced.

The "polyamines" referred to in the present invention are common natural substances ubiquitous in organisms, and are aliphatic hydrocarbon compounds with two or more primary amine groups. Examples include 1,3-diaminopropane, putrescine, cadaverine, norspermidine, spermidine, homospermidine, aminopropylcadaverine, thermine (norspermine), spermine, thermospermine, canavalmine, aminopentylnorspermidine, N,N-bis(aminopropyl)cadaverine, homospermine, caldopentamine, homocaldopentamine, caldohexamine, and homocaldohexamine.

In the specification, "root and tuber crop" include sweet potatoes and white potatoes.

Polyamine Metabolism-Related Enzyme Genes

As used in the present invention, "polyamine metabolism-related enzyme genes" are genes coding for amino acids of enzymes involved in polyamine biosynthesis in plants. Examples which are believed to be involved, and to be rate limiting, include arginine decarboxylase (ADC) and ornithine decarboxylase (ODC) genes for the typical polyamine putrescine, S-adenosylmethionine decarboxylase (SAMDC) and spermidine synthase (SPDS) genes for spermidine, and S-adenosylmethionine decarboxylase (SAMDC) and spermine synthase (SPMS) genes for spermine.

Arginine decarboxylase (ADC: EC4.1.1.19.) is an enzyme catalyzing the reaction producing agmatine and carbon dioxide from L-arginine. Ornithine decarboxylase (ODC: EC4.1.1.17.) is an enzyme catalyzing the reaction producing putrescine and carbon dioxide from L-ornithine. S-adenosylmethionine decarboxylase (SAMDC: EC4.1.1.50.) is an enzyme catalyzing the reaction producing adenosylmethylthiopropylamine and carbon dioxide from S-adenosylmethionine. Spermidine synthase (SPDS: EC2.5.1.16.) is an enzyme catalyzing the reaction producing spermidine and methylthioadenosine from putrescine and adenosylmethylthiopropylamine.

These genes, any of which may be derived, can be isolated from various plants. Specific examples include dicotyledons such as Cucurbitaceae; Solanaceae; Brassicaceae such as *Arabidopsis thaliana*; Papilionaceae such as alfalfa and *Vigna unguiculata*; Malvaceae; Asteraceae; Chenopodiaceae; and Convolvulaceae; or monocotyledons such as Gramineae, including rice, wheat, barley, and corn. Drought-resistant cactus or *Mesembryanthemum crystallinum* are also included. Cucurbitaceae are preferred, and *Cucurbita ficifolia* Bouche is especially preferred.

Plant tissue in which the plant-derived polyamine metabolism-related enzyme genes of the invention are isolated may be in the form of seeds or in the process of growing. The genes may be isolated from part or all of the tissue of growing plants. Any part can be used to isolate genes, but whole plants, buds, flowers, ovaries, fruit, leaves, stems, roots, and the like are preferred.

Preferred examples of polyamine metabolism-related enzyme genes used in the present invention include the spermidine synthase gene, S-adenosylmethionine decarboxylase, and arginine decarboxylase gene. Specific examples include:

DNA having the base sequence represented by base numbers 77 through 1060 in the base sequence given in SEQ ID NO. 1;

DNA having the base sequence represented by base numbers 456 through 1547 in the base sequence given in SEQ ID NO. 3; and DNA having the base sequence represented by base numbers 541 through 2661 in the base sequence given in SEQ ID NO. 5.

Further examples include:

DNA having a base sequence capable of hybridizing under stringent conditions with any of the above sequences, and coding for a polypeptide with polyamine metabolism-related enzyme activity equivalent to those sequences.

Still further examples include:

DNA comprising any of the above base sequences with 1 or more bases deleted, substituted, inserted, or added, and coding for a polypeptide with polyamine metabolism-related enzyme activity equivalent to those sequences.

The "stringent conditions" referred to here mean conditions under which only base sequences coding for a polypeptide with polyamine metabolism-related enzyme activity equivalent to the polyamine metabolism-related enzyme encoded by a specific polyamine metabolism-related enzyme gene sequence form hybrids with the specific sequence (referred to as specific hybrids), and base sequences coding for polypeptides with no such equivalent activity do not form hybrids with the specific sequence (referred to as non-specific hybrids). One with ordinary skill in the art can readily select such conditions by varying the temperature during the hybridization reaction and washing process, the salt concentration during the hybridization reaction and washing process, and so forth. Specific examples include, but are not limited to, conditions under which hybridization is brought about at 42° C. in 6×SSC (0.9 M NaCl, 0.09 M trisodium citrate) or 6×SSPE (3M NaCl, 0.2 M NaH$_2$PO$_4$, 20 mM EDTA-2Na, pH 7.4), and the product is washed with 0.5×SSC at 42° C.

In general, it is well known by those skilled in the art that substitution, deletion, insertion or addition of one or more amino acids in amino acid sequence of biologically active proteins may maintain those physiological activities. The "base sequences with 1 or more bases deleted, substituted, inserted, or added" referred to here include genes that have such modifications and that code for a polyamine metabolism-related enzyme, such genes are included within the scope of the present invention. For example, the poly A tail or 5', 3' end nontranslation regions may be "deleted," and bases may be "deleted" to the extent that one or more amino acids are deleted. Bases may also be "substituted", as long as no frame shift results. Bases may also be "added" to the extent that amino acids are added. However, it is essential that such modifications do not result in the loss of polyamine metabolism-related enzyme activity. "Genes with one or several bases deleted, substituted, or added" are preferred.

Such modified DNA can be obtained by modifying the DNA base sequences of the invention so that amino acids at specific sites are substituted, deleted, inserted, or added by site-specific mutagenesis, for example (Nucleic Acid Research, Vol. 10, No. 20, 6487-6500 (1982)).

In the present invention, "antisense genes" refer to genes with a sequence complementary to the base sequence of a polyamine metabolism-related enzyme gene. Antisense DNA is complementary the base sequence of SEQ ID NOS. 1, 3, or 5, for example. Antisense RNA is produced from that.

Inhibitors of Endogenous Polyamine Metabolism-Related Enzyme Genes

The inhibitors suppress the expression of the genes, and are not particularly limited, and, for example, include antisense DNA, or double stranded RNA (dsRNA) or RNAi of the gene and sequences selected from upstream or downstream.

In the antisense method, a DNA fragment (antisense DNA), having a sequence complementary to that of the cDNA or the mRNA precursor of the target gene is introduced in the plant for inducing the production of antisense RNA. The produced RNA then base-pairs with the mRNA of the target gene thus inhibiting the translation of the protein. The antisense DNA sequence may be any sequence provided it results in the base-pairing with the mRNA of at least one type of endogenous polyamine metabolism-related enzyme gene. The sequence may preferably have the same source as the endogenous polyamine metabolism-related enzyme gene, or may be a sequence from a different origin if the polyamine metabolism-related enzyme gene has a high interspecies homology. The antisense DNA may have any length, total or partial sequence, provided it results in the base-pairing with the mRNA of at least one type of endogenous polyamine metabolism gene. The source of the sequences need not necessarily be the same.

The antisense DNA may be complementary to either a regulatory region on the 5' upstream side that includes an intron or exon of the gene, or a promoter of the gene, or a region on the downstream side of the termination codon, which affects gene expression. The length of the antisense DNA is at least 20 bases, preferably at least 100 bases, more preferably at least 300 bases, most particularly at least 500 bases. The transcription product of the antisense DNA is hybridized with mRNA of endogenous polyamine metabolism-related enzyme genes, or is hybridized to a non-coding region (for example promoter, intron, transcription termination factor) of endogenous polyamine metabolism-related enzyme genes or an upstream or downstream sequence thereof.

RNAi comprises RNA having a sense sequence in relation to a target gene and an antisense sequence in relation to a target gene, and the sense sequence and antisense sequence may be included on 2 strands of RNA respectively and function as double stranded RNA, or may be included on 1 RNA strand and function as a single RNA molecule having a double strand portion and a loop sequence which links sense and antisense sequences.

The RNA interference method (RNAi) is a method developed in recent years wherein double-stranded RNA (dsRNA) that is introduced in the cell causes the specific breakup of mRNA having a sequence homologous to that of dsRNA, thus suppressing the expression of the gene. RNAi was used in plants in 1998 for the transformation of potatoes by hairpin dsRNA transcription suppressing the expression of the exogenous GUS (beta-glucuronidase) gene, as reported in Proc. Natl. Acad. Sci. USA, 95, 13959-13964, 1998); in 2000 was also reported the suppression of the endogenous gene in *Arabidopsis thaliana* (Proc. Natl. Acad. Sci. USA, 97, 4985-4990, 2000). RNAi can also take place in plants by direct transgenic introduction of dsRNA or siRNA (small interfering RNA) or vectors of transcribed hairpin dsRNA using protoplast electroporation (Proc. Natl. Acad. Sci. USA, 99, 11981-11986, 2002; Plant J., 24, 895-903, 2000). Reports so far concerning numerous plants, i.e. rice, *Arabidopsis thaliana*, tobacco, maize, barley, wheat, cotton, etc. (Plant J., 27, 581-590, 2001, Plant Cell, 14, 857-867, 2002) indicate that RNAi seems to be universal mechanism in a wide range of situations.

Plant and their Progeny with Improved Morphogenesis

"Organ" in the present invention, as described above, means all organs (tissues) of the plant, including, for example, stems, tubers, leaves, roots, tuberous roots, buds, flowers, petals, ovaries, fruit, pods, capsules, seeds, fibers and ovules, etc. The traits relating to the form of the organ (tissue) may be of the quantity, the growth and development period, shape, color, properties, and characteristics, etc.

A "plant in which morphogenesis has been improved" and a "plant having improved morphogenesis" of the present invention refers to a plant wherein an exogenous polyamine metabolism-related enzyme gene or an inhibitor of an endogenous polyamine metabolism-related enzyme gene is introduced to make a trait relating to morphogenesis that, compared to prior to introduction, enhance, improves or suppresses quantity, the growth and development period, shape, color, properties, or characteristics. For example, by introducing into a plant a polyamine metabolism-related enzyme gene or the inhibitor, the traits related to the formation of the stems, leaves, flowers, or seeds are improved compared to a plant not having the exogenous polyamine metabolism-related enzyme gene or the inhibitor. However, the invention is not limited to these.

Concretely, a "plant with the number of stems improved" by a genetic sequence that modulates the amount of polyamine is a plant with an increased number of plant stems (including main stems, side stems, flower stalks, trunks, branches, etc.) and a plant with a decreased or reduced number of plant stems (including main stems, side stems, flower stalks, trunks, branches, etc.) based on the inhibitor.

A "plant having an improved number of leaves" is a plant with an increased or a decreased number of or reduced plant leaves.

A "plant having an improved number of flowers or flower blooming period" is a plant with an increased or a decreased number of or reduced plant flowers, or a plant with an early plant flower blooming period or an extended blooming period. A "plant having an improved number of ovaries or ovary development period" is a plant with an increased or a decreased number of or reduced plant ovaries, fruit, pods and capsules, or a plant with an increased or a decreased or a reduced growth or development period from bearing to maturity of ovaries, fruit, pods and capsules.

A "plant having an improved number of seeds" is a plant with an increased or a decreased number of, or reduced plant seeds (including ovules).

In this way, improvement of product quality, productivity and yield of the plant (organs and tissues, etc.), as well as improved product characteristics can be expected. Moreover, in edible plants such as vegetables and fruit, it is possible that reducing the amount of polyamine of the edible part (leaves, fruit, tuber, tuberous root, etc.) will have a beneficial result on the characteristics, such as the product quality. Consequently, it is possible to attempt to improve the yield while improving the quality by expressing the inhibitor in these edible parts, and by expressing polyamine metabolism-related enzyme genes in the other parts.

Further, improvement of the adaptability (resistance) to various kinds of environmental stress may be expected by improving morphogenesis and varying the shape and formation of the plant. Specifically, it appears that the number of leaves and the green color of leaves based on chlorophyll may be increased; roots (including tuberous roots and tubers) may be elongated; the number and thickness of stems may be increased; consequently, the environmental adaptability of the plant may be increased.

In one of the preferable embodiments of the present invention, the difference in external appearance of the plant during the vegetative growth period is small (the leaves are darker green), but a notable improvement in such organs as the leaves, flowers and stems is more notable during the reproductive growth period, and this reveals that the latent capacity (potential) of the plant was improved.

The plants of the invention include not only the plant in its entirety (whole plant), but also calli, seeds, all plant tissues, leaves, stems, tubers, roots, tuberous roots, buds, flowers, petals, ovaries, fruit, pods, ovules and fibers. Their progeny are also included in the plants of the invention.

Useful substances obtained from plants and their progeny in the present invention indicate useful substances produced by plants and their progeny in which the introduction of an exogenous polyamine metabolism-related enzyme gene provides or improves morphogenesis compared to before the gene was introduced. Examples of useful substances include amino acids, oils and lipids, starches, proteins, phenols, hydrocarbons, cellulose, natural rubber, pigment, enzymes, antibodies, vaccines, medicinal products, and biodegradable plastics.

The plants of the present invention are plants with no exogenous polyamine metabolism-related enzyme gene, to which such an exogenous polyamine metabolism-related enzyme gene is introduced by genetic engineering and is retained in a stable manner. As used herein, retained in a stable manner means that the polyamine metabolism-related enzyme gene is expressed in the plant at least in which the polyamine metabolism-related enzyme gene has been introduced, and is retained in the plant cells long enough to result in the improvement of morphogenesis. The polyamine metabolism-related enzyme gene is, therefore, preferably incorporated on the chromosomes of the host plant. The polyamine metabolism-related enzyme gene or genes should even more preferably be retained in subsequent generations.

As used herein, "exogenous" means not endogenous to the plant, but externally introduced. Accordingly, an exogenous polyamine metabolism-related enzyme gene may be a polyamine metabolism-related enzyme gene homologous to the host plant (that is, derived from the host plant), which is externally introduced by genetic manipulation. The use of a host-derived polyamine metabolism-related enzyme gene is preferred in consideration of the identity of the codon usage.

The exogenous polyamine metabolism-related enzyme gene may be introduced into plants by any method of genetic engineering. Examples include protoplast fusion with heterologous plant cells having the polyamine metabolism-related enzyme gene, infection with a plant virus having a viral genome genetically manipulated to express the polyamine metabolism-related enzyme gene, or transformation of host plant cells using an expression vector containing the polyamine metabolism-related enzyme gene.

The plants of the invention are preferably transgenic plants which are obtained by the transformation of cells of plants lacking the exogenous polyamine metabolism-related enzyme gene in an expression vector containing the exogenous polyamine metabolism-related enzyme gene under the control of a promoter capable of functioning in plants.

Examples of promoters capable of functioning in plants include the 35S promoter of the cauliflower mosaic virus (CaMV) which is constitutively expressed in plant cells, the nopaline synthase gene (NOS) promoter, octopine synthase gene (OCS) promoter, phenylalanine ammonia lyase (PAL) gene promoter, and chalcone synthase (CHS) gene promoter. Other well-known plant promoters not limited to these are also available.

Not only promoters constitutively expressed in the entire organ such as the 35S promoter, but also promoters specific to organs or tissues can be used to express the target gene in only target organs or tissues so as to improve morphogenesis in specific organs or tissues. For example, a polyamine metabolism-related enzyme gene and a promoter capable of function specific to flower organ (such as WO99/43818, Japanese Unexamined patent publication 178572/1999, Japanese Unexamined patent publication 316582/2000) can be used to improve the number of flowers and a flowering period. In addition, growth and duration of development of ovary and fruit can be improved by using promoters specific to ovary and fruit (Plant Mol. Biol., 11, 651-662, 1988).

If a time specific promoter is used, the target gene can be expressed only at a specific time, and the morphogenesis can be improved at only the specified time period. For example, morphogenesis can be improved only during the vegetative growth period by using a polyamine metabolism-related enzyme gene, and a promoter that works in the vegetative growth period.

Promoters regulated by low temperature, elevated temperature, stress, drought, light, heat, hormones, damage or the like can be used to express the target gene according to the living environment. For example, a polyamine metabolism-related enzyme gene and a promoter capable of transcription only when the plant is exposed to low temperatures (such as the BN115 promoter: Plant Physiol., 106, 917-928 (1999)) can be used to control the polyamine metabolism of the plant only at low temperatures and to improve morphogenesis. A polyamine metabolism-related enzyme gene and a promoter capable of transcription only when the plant is exposed to drought (such as the Atmyb2 promoter: The Plant Cell, 5, 1529-1539, 1993) can also be used to control the polyamine metabolism of the plant during drought and to improve morphogenesis.

The exogenous polyamine metabolism-related enzyme gene in the expression vector of the present invention is located downstream of the promoter so that transcription is controlled by the promoter capable of functioning in plants. A transcription termination signal (terminator region) capable of functioning in plants should also be added downstream of the polyamine metabolism-related enzyme gene. An example is the terminator NOS (nopaline synthase) gene.

The expression vector of the present invention may also contain a cis-regulatory element such as an enhancer sequence. The expression vector may also contain a marker gene for selecting transformants such as a drug-resistance gene marker, examples of which include the neomycin phosphotransferase II (NPTII) gene, the phosphinothricin acetyl transferase (PAT) gene, and the glyophosate resistance gene. Because the incorporated gene is sometimes dropped in the absence of selection pressure, it is advantageous to ensure that a herbicide resistance gene is also present on the vector so that the use of a herbicide during cultivation will always result in conditions involving selection pressure.

To facilitate mass production and purification, the expression vector should also contain a selection marker gene (such as ampicillin resistance gene or tetracycline resistance gene) in *E. coli* and a replication origin capable of autonomous replication in *E. coli*. The expression vector of the present invention can be constructed in a simple manner by inserting the selection marker gene as needed and an expression cassette of the polyamine metabolism-related enzyme gene at the cloning site of an *E. coli* vector (pUC or pBR series).

When the exogenous polyamine metabolism-related enzyme gene is introduced by infection with *Agrobacterium tumefaciens* or *Agrobacterium rhizogenes*, the polyamine metabolism-related enzyme gene expression cassette can be inserted in the T-DNA region (region transferred to plant chromosome) on a Ti or Ri plasmid of the cells. At present, binary vector systems are used in standard methods of transformation with *Agrobacterium*. The necessary functions for T-DNA transfer are independently provided by both the T-DNA itself and the Ti (or Ri) plasmid, these structural elements being divided on separate vectors. The binary plasmid has 25 bp border sequences at both ends necessary for cleaving and combining the T-DNA, and the plant hormone gene inducing crown gall (or hairy root) is removed, simultaneously providing room for inserting the exogenous gene. Examples of commercially available binary vectors include pBI101 and pBI121 (both by Clontech). The Vir region involved in the incorporation of the T-DNA has trans action on the separate Ti (or Ri) plasmid referred to as the helper plasmid.

Various conventionally known methods can be used for the transformation of the plants. Examples include the PEG method in which protoplasts are isolated from plant cells by treatment with a cell wall-degrading enzyme such as cellulase or hemicellulase, and polyethylene glycol is added to a suspension of the protoplasts and an expression vector containing the aforementioned polyamine metabolism-related enzyme gene expression cassette to incorporate the expression vector into the protoplasts by a process such as endocytosis; the liposome method in which an expression vector is introduced by ultrasonic treatment or the like into lipid membrane vesicles such as phosphatidylcholine, and the vesicles are fused with protoplasts in the presence of PEG; methods of fusion in a similar process using micelles; and electroporation in which electrical pulses are applied to a suspension of protoplasts and an expression vector to incorporate the vectors in the external solution into the protoplasts. However, these methods are complicated in that they require a culturing technique for the redifferentiation of the protoplasts into plants. Processes for introducing the gene into intact cells with cell walls include direct injection such as microinjection in which a micropipette is inserted into cells to inject the vector DNA in the pipettes under hydraulic or gas pressure into the cells, or the particle gun method in which metal microparticles coated with DNA are accelerated through the detonation of an explosive or gas pressure and thus introduced into the cells, and methods involving the use of infection with *Agrobacterium*. Drawbacks of microinjection are the need for considerable training and the small number of cells that are handled. It is therefore more desirable to transform plants with more convenient methods such as the *Agrobacterium* method and the particle gun method. The particle gun method is useful in that genes can be directly introduced into the apical meristem of plants while cultivated. In the *Agrobacterium* method, the genomic DNA of a plant virus such as the tomato golden mosaic virus (TGMV) or another gemini virus is simultaneously inserted between the border sequences into the binary vector, so that the viral infection can spread throughout the entire plant and the target gene can be simultaneously introduced into the entire plant simply by inoculating cells at any location of the cultivated plant with the viral cell suspension.

Specific examples of methods for obtaining polyamine metabolism-related enzyme genes as well as methods for introducing the target gene using *Agrobacterium* to produce transformants are given below. With respect to inhibitors of endogenous polyamine metabolism-related enzyme genes, those skilled in the art can produce a transgenic plant with reference to the following description.

1. Obtaining Polyamine Metabolism-Related Enzyme Genes
  (1) Preparation of cDNA Library for PCR
  Poly(A)$^+$RNA is extracted in the usual manner from root tissue of *Cucurbita ficifolia* Bouche which has undergone 3 days of low temperature treatment at 18° C. daytime/14° C. night time. A cDNA library can be prepared for use in PCR from the isolated poly(A)$^+$RNA using a commercially available marathon cDNA Amplification Kit (by Clontech) or the like. The isolated poly(A) $^+$RNA is used as template, and reverse transcriptase and modified lock-docking oligo(dT) primer with two degenerate nucleotide positions at the 3' end are used to synthesize the first-strand cDNA. Double-stranded cDNA is obtained by polymerase reaction. The double-stranded cDNA is blunted with T4 DNA polymerase, and a Marathon cDNA adapter is ligated, giving a library of double-stranded cDNA with the adapter added.

(2) Design of PCR Primer

The SPDS gene, SAMDC gene, ADC gene, and ODC gene can be isolated as the polyamine metabolism-related enzyme gene. The SPDS gene can be isolated from *Cucurbita ficifolia* Bouche or *Hyoscyamus niger*, the SAMDC gene can be isolated from potatoes, spinach, or tobacco, the ADC gene can be isolated from soybean, peas, or tomatoes, and the ODC gene can be isolated from *Datura*. The base sequences have already been determined. Extremely well conserved regions can therefore be selected by comparing known base sequences, and DNA oligomers can be synthesized to design primers for PCR.

(3) Obtaining SPDS Gene, SAMDC Gene, and ADC Gene Fragments by PCR

The cDNA library for PCR prepared in (1) above is used as template, and the primers designed in (2) above are used to carry out PCR. The PCR products are isolated by gel electrophoresis and are purified with glass milk or the like. The purified PCR products are ligated to a cloning vector such as the TA vector.

The base sequences of the cloned cDNA are determined by the method of Maxam-Gilbert, the dideoxy method, or the like. Either method can be carried out using commercially available kits, and an auto sequencer can be used for automatic sequencing.

(4) Isolation of Full-Length Gene

The full-length gene can be obtained in the usual manner by plaque hybridization, RACE (rapid amplification of cDNA ends), Marathon RACE, or the like.

The genes thus obtained are genes that participate in polyamine biosynthesis, and using these genes it is possible to control polyamine levels by controlling the expression of genes on a molecular biological level, and to produce plants with various types of improved morphogenesis.

2. Introduction of Target Gene with *Agrobacterium* into *Arabidopsis Thaliana*, and Preparation of Transgenic Plant The genes obtained in 1. above can be introduced into a plant host to produce transgenic plants with improvement of various types of morphogenesis such as morphogenesis of stems, leaves, flowers, ovaries, fruit, pods and seeds in particular.

(1) Preparation of Expression Construct and Transformation of *Agrobacterium*

Expression constructs can be prepared by cleaving the polyamine metabolism-related enzyme gene obtained in 1. above with suitable restriction enzymes so as to include all of the open reading frame, then ligating suitable linkers as needed, and inserting the gene into a plant transformation vector. Examples of plant transformation vectors which can be used include pBI101 and pBI121.

The resulting expression construct is amplified in *E. coli*, and the expression construct is then transformed by tripartite conjugation (Nucleic Acid Research, 12, 8711 (1984)), freeze thawing, electroporation, or the like with *Agrobacterium tumefaciens* C58, LBA4404, EHA101, or the like. Tripartite conjugation involves, for example, the culture of *E. coli* having an expression construct containing the target gene, *E. coli* having a helper plasmid (such as pRK2013), and *Agrobacterium* on medium containing an antibiotic (such as rifampicillin, kanamycin, or hygromycin) so as to obtain transformed *Agrobacterium*.

(2) Production of Transgenic Plant

Parts of plants to which genes can be introduced in the present invention include the entire plant, plant organs (such as leaves, stems, roots, flower organs, vegetative points, and seeds), plant tissue (such as epidermis, phloem, parenchyma, xylem, and vascular bundle), and plant cultured cells.

The target gene can be introduced upon infecting plants with the transformed *Agrobacterium* prepared in (1) by callus regeneration (Plant Cell Reports, 12, 7-11 (1992)), for example. That is, MSO plates (4.6 g Murashige-Skoog mineral salts, 10 g sucrose, 1 mL/L of 1000× vitamin stock, pH 6.2) can be inoculated with seeds of *Arabidopsis thaliana* in the usual manner for aseptic culture. After taking root, slices of root can be used in the culture of callus on CIM plates (MSO plates supplemented with 2,4-dichlorophenoxyacetic acid to a final concentration of 0.5 µg/mL and kinetin to a final concentration of 0.05 µg/mL). *Agrobacterium* transformed with plasmid containing the target gene joined to the promoter, kanamycin and hygromycin resistance genes is cultured, diluted samples are aliquoted into tubes, and slices of the roots on which callus is forming are soaked for several days of co-cultivation on CIM plates. When the strains have grown enough to become visible to the naked eye, they are disinfected for several days of culture on SIMC plates (MSO plates supplemented with N6-[2-isopentenyl]adenine to a final concentration of 5 µg/mL, indoleacetic acid (IAA) to a final concentration of 0.15 µg/mL, and claforan to a final concentration of 500 µg/mL). The slices are finally cultured on SIMCS plates (plates containing kanamycin and hygromycin) and repeatedly transplanted to fresh plates every week. The transformed slices continue to be grown, resulting in callus. Slices that have not been transformed will turn brown, as the selection is based on antibiotics. The transformants are about 5 mm, and are cultured until rosette leaves are formed. When the complete rosette form is evident, the roots of the transformants are cut with a scalpel to leave out the callus and are transplanted to RIM plates (MSO plates supplemented with IAA to a final concentration of 0.5 µg/mL). When large calli are attached, the roots will show through the callus even if they have taken root, and vascular bundles will not often become joined to the rosettes. After about 8 to 10 days, they become planted on rock wool soaked with mineral salts (5 mM $KNO_3$, 2.5 mM K-phosphate buffer (pH 5.5), 2 mM $MgSO_4$, 2 mM $Ca(NO_3)_2$, 50 µM Fe-EDTA, 1000× microelements (70 mM $H_3BO_3$, 14 mM $MnCl_2$, 0.5 mM $CuSO_4$, 1 mM $ZnSO_4$, 0.2 mM $NaMoO_4$, 10 mM NaCl, 0.01 mM $CoCl_2$) 1 mL/L). Plants that have flowered and formed pods are transplanted to soil soaked with mineral salt media, allowing the seeds to be obtained. The seeds are disinfected and are allowed to germinate upon the inoculation of MSH (MSO plates supplemented with hygromycin to a final concentration of 5 U/mL), thereby allowing transformants to be obtained.

Plants can be infected with the transformed *Agrobacterium* prepared in (1) by infiltration at reduced pressure (The Plant Journal, 19(3), 249-257 (1999)) to introduce the target gene. That is, potting commercial nursery soil (such as Metromix) is inoculated with seeds of *Arabidopsis thaliana*, which are cultivated under conditions involving long days (such as 16 hour days and 8 hour nights) at 22° C. After about 3 to 4 weeks, the extended main axis (flower stalk) is cut to begin induction of lateral shoots. After about 1 week of top pruning, the *Arabidopsis thaliana* is dipped in a suspension of cultured *Agrobacterium* transformants, is placed in a dessicator, which is suctioned with a vacuum pump to about −0.053 MPa (400 mmHg), and is then allowed to stand at ambient temperature for 10 minutes. The infected pot is transferred to a deep-bottomed tray and tilted on its side to allow a small amount of water to drip into the bottom of the tray, a transparent covering is placed on it, and it is then allowed to stand for about 1 day under humid conditions. The infected pot is then raised, and cultivation is started under conditions involving long days at 22° C. to harvest the seeds.

The seeds are harvested for about 2 to 4 weeks, and the harvested seeds are strained through a tea strainer or the like to remove debris and husks, and are dried and stored in a dessicator.

The selection of transgenic plants involves sterilizing the harvested seeds in the usual manner and suspending them in about 9 mL of 0.1% agar aqueous solution, then spreading the suspension on selection medium (such as 1×MS salt, 1× Gamborg B5 vitamin, 1% sucrose, 0.5 g/L MES, 0.8% agar, 100 mg/L carbenicillin, 50 mg/L kanamycin, 40 mg/L hygromycin) for aseptic culture at 22° C. Transgenic plants showing resistance to the antibiotics will grow well and can be identified in about 1 to 2 weeks. Transgenic plants with about 4 to 6 true leaves are transplanted to pots containing potting commercial nursery soil to begin cultivation during long days at 22° C.

DNA is extracted in the usual manner from the resulting transgenic plants, the DNA is cleaved with suitable restriction enzymes, and the polyamine metabolism-related enzyme gene can be used as probe in Southern hybridization to determine whether or not the gene has been introduced.

RNA can be extracted in the usual manner from transgenic or non-transgenic plants to prepare probes with the polyamine metabolism-related enzyme gene sense sequence or antisense sequence, and the probes can be used in Northern hybridization to study the expression of the target gene.

Callus can be induced from the resulting transgenic plants to produce callus.

The proportion of transformed progeny T2, created by self-pollination, of transgenic plants (T1) obtained by reduced pressure infiltration will ordinarily follow Mendel's laws. For example, when the polyamine metabolism-related enzyme gene is heterozygously incorporated in a gene locus, the proportion of transformants in T2 progeny will be 3:1. In terms of T3 progeny produced by self-pollination upon cultivation of T2 progeny, when transformants appear in all progeny, the T2 transgenic plants will be homozygotes, and when transformants are isolated in a proportion of 3:1, the T2 transgenic plants will be heterozygotes with respect to the introduced polyamine metabolism-related enzyme gene.

The plants thus selected, which are homozygote with respect to the introduced polyamine metabolism-related enzyme gene, are very useful in the field of seed industry as independent line in which improved morphogenesis is fixed.

The transgenic plant whose gene expression analysis of polyamine metabolism-related enzyme gene is conducted by Southern analysis or Northern analysis can be subjected to evaluation of polyamine content and various types of morphogenesis.

In the case of polyamine assay, for example, 5% perchloric acid aqueous solution is added to 0.05 to 1 g sample to extract the polyamine. Assay of the extracted polyamines involves fluorescent labeling by benzoylation, dansylation, or the like, followed by analysis with an internal standard using high performance liquid chromatography (HPLC) with a UV detector or fluorescence detector.

For example, there are methods to evaluate the various types of morphogenesis. Stem formation can be evaluated by sowing in a suitable culture medium or potting soil T2 or T3 seeds obtained by self-pollination of a transgenic plant, growing under long day conditions (day length of daylight/dark: 16 hours/8 hours) at 20 to 25° C., and investigating the number and shape of stems (for example, main flower stalks, side flower stalks, branches, etc.). Leaf formation can be evaluated by sowing in a suitable culture medium or potting soil T2 or T3 seeds obtained by self-pollination of a transgenic plant, growing under long day conditions (day length of daylight/dark: 16 hours/8 hours) at 20 to 25° C., and investigating the number and shape of leaves (for example, rosette leaves, true leaves, etc.). Flower formation can be evaluated by germinating in a suitable culture medium or potting soil T2 or T3 seeds obtained by self-pollination of a transgenic plant, growing under long day conditions (day length of daylight/dark: 16 hours/8 hours) at 20 to 25° C., and investigating the number, blooming time, blooming period, shape, and color of flowers, etc. Ovary formation can be evaluated by germinating in a suitable culture medium or potting soil T2 or T3 seeds obtained by self-pollination of a transgenic plant, growing under long day conditions (day length of daylight/dark: 16 hours/8 hours) at 20 to 25° C., and investigating the number, shape, color, and development period from setting the fruit to maturation of the ovaries (for example, pods and fruit, etc.). Seed formation can be evaluated by germinating in a suitable culture medium or potting soil T2 or T3 seeds obtained by self-pollination of a transgenic plant, growing under long day conditions (day length of daylight/dark: 16 hours/8 hours) at 20 to 25° C., and investigating the number and shape of seeds, as well as germination rate after harvesting, etc.

Examples of plants which may be transformed in the invention include, but are not limited to, dicotyledons, monocotyledons, herbaceous plants, and shrubs. Examples include sweet potatoes, tomatoes, cucumbers, squash, melons, watermelon, tobacco, *Arabidopsis thaliana*, bell peppers, eggplant, beans, taro, spinach, carrots, strawberries, white potatoes, rice, corn, alfalfa, wheat, barley, soybeans, rapeseed or canola, *sorghum, Eucalyptus*, poplar, kenaf, *Eucommia ulmoides*, sugarcane or sugarbeet, *Chenopodium album*, lilies, orchids, carnations, roses, petunia, *Torenia fournieri, Antirrhinum majus, Cyclamen persicum, Gypsophila elegans, Pelargonium graveolens*, sunflowers, *Zoisia japonica*, cotton, matsutake mushrooms, shiitake mushrooms, mushrooms, ginseng, citrus fruit, bananas, and kiwi fruit, *Manihot utilissima, Metroxylon sagu* Roxb. Sweet potatoes, white potatoes, tomatoes, cucumbers, rice, corn, soybeans, wheat, *petunia, Torenia fournieri, Eucalyptus* and cotton are preferred.

According to the present invention, improvement of various types of morphogenesis in plants is possible, and it may be expected that the quality of plant organs and tissue, value, productivity and yield may be improved, or that resistance to collapsing may be improved by making dwarves, etc. Specifically, it may be expected that when producing the organs as an agricultural product by increasing the number of stems, leaves, flowers, ovaries, fruit, pods, and seeds, increased quality, productivity and yield may be expected. For example, it may be expected that increasing the number of seeds per rice plant will augment the yield of rice that can be harvested. It may be expected that increasing the number of female ears per corn plant will augment the yield of kernels. It may be expected that increasing the number of pods per soybean plant will augment the yield of beans. It may be expected that increasing the number of cotton bolls per plant will augment the yield of fiber harvested. It may be expected that increasing the number of tubers and tuberous roots of white potatoes and sweet potatoes will augment the yield of potatoes. It may be expected of fruit trees that increasing the number of fruit (ovaries) set and lengthening the development period will improve producibility. It may be expected of ornamental plants that increasing the number of stems, leaves, and especially, flowers, as well as delaying the blooming period and making better visual appeal by miniaturization, will increase the commercial value. Further, it may be expected that by changing the shape and formation of the plant, various environmental adaptability may be improved, stabilization of cultivation and producibility may be improved, and the land under cultivation may be expanded.

The polyamine treatment of plants according to the present invention can be suitably used for tubers including sweet potatoes and white potatoes, in particular, sweet potatoes.

From tuber potato are obtained large amounts of tuber (sweet potato and white potato) starch and other saccharides, which are used as raw materials in the manufacture of biodegradable plastics. Examples of biodegradable plastics include, among others, polyhydroxybutyrate, polyhydroxyvalerate, poly-beta-hydroxybutyric acid, polycaprolactone, poly(butylene succinate), poly(butylene adipate), poly(ethylene succinate), poly(D,L,DL)lactate (polylactide), poly(glycolic acid) (polyglycolide), cellulose acetate, chitosan/cellulose/starch, modified starches, etc. or binary and ternary copolymers of the above, etc. These biodegradable plastics are compounds known in the art and may be manufactured using conventional fermentation or chemical synthesis methods, etc.

BEST MODE FOR CARRYING OUT THE INVENTION

The invention is illustrated in further detail by the following examples, but they are provided only as examples and do not in any way limit the scope of the invention.

Example 1

Cloning of Plant-Induced Polyamine Metabolism-Related Enzyme Gene (1) Preparation of Poly(A) $^+$RNA Vermiculite was inoculated with *Cucurbita ficifolia* Bouche, and the plants were transplanted to pots filled with commercially available fine soil (Sansan soil, by Takii & Co., Ltd.) at the cotyledon development stage. The potted *Cucurbita ficifolia* Bouche was placed in incubators (air temperature: day 26° C./night 22° C., 13 hour long days) for plant cultivation. At the two leaf stage, the incubator temperature was lowered to day 18° C./night 14° C. to begin low temperature treatment. After 3 days of low temperature treatment, the plants were divided into roots, stems, and leaves for sampling. The samples were stored in an −80° C. freezer until RNA extraction.

About 4 g of *Cucurbita ficifolia* Bouche root tissue was immediately frozen in liquid nitrogen and finely milled in a mortar and pestle in the presence of liquid nitrogen. 10 mL of 0.2 M Tris acetate buffer (5 M guanidine thiocyanate, 0.7% β-mercaptoethanol, 1% polyvinyl pyrrolidone (M.W. 360,000), 0.62% N-lauroylsarcosine sodium salt, pH 8.5) for extraction was then added, and the tissue was milled for 2 minutes while cooled on ice using a Polytron homogenizer (by Kinematica). The mercaptoethanol and polyvinyl pyrrolidone were added just before use. The milled product was then centrifuged for 20 minutes at 17,000×g, and the supernatant was recovered.

The supernatant was filtered through mira cloth, the filtrate was gently layered in 1.5 mL of 5.7 M cesium chloride solution placed in an ultracentrifugation tube, the contents were centrifuged for 20 hours at 155,000×g, the supernatant was then discarded, and the RNA precipitate was recovered. The precipitate was dissolved in 3 mL of 10 mM Tris-HCl, 1 mM EDTA-2Na, pH 8.0 (referred to as TE buffer), an equivalent amount of phenol:chloroform:isoamyl alcohol (volumetric ratio of 25:24:1) was furthermore added, the ingredients were mixed and then centrifuged, and the upper aqueous layer was recovered. $^1/_{10}$-fold 3 M sodium acetate (adjusted to pH 6.2 with glacial acetic acid) and 2.5-fold ethanol were added to the aqueous layer, the ingredients were mixed, and the mixture was allowed to stand over night at −20° C. The mixture was then centrifuged for 20 minutes at 17,000×g, and the resulting precipitate was washed with 70% ethanol and dried at reduced pressure.

The dried preparation was dissolved in 500 μL of the aforementioned TE buffer, giving total RNA solution. The RNA solution was incubated for 5 minutes at 65° C. and then quenched on ice. An equivalent amount of 2× binding buffer (10 mM Tris-HCl, 5 mM EDTA-2Na, 1 M NaCl, 0.5% SDS, pH 7.5) was added to the RNA solution, and the solution was layered on an oligo dT cellulose column (by Clontech) equilibrated with equilibration buffer (10 mM Tris-HCl, 5 mM EDTA-2Na, 0.5 M NaCl, 0.5% SDS, pH 7.5). The column was then flushed with about 10-fold equilibration buffer described above, and the poly (A) $^+$RNA was eluted with elution buffer (10 mM Tris-HCl, 5 mM EDTA-2Na, pH 7.5).

$^1/_{10}$-fold 3 M sodium acetate aqueous solution described above and 2.5-fold ethanol were added to the resulting eluate, the ingredients were mixed, and the mixture was allowed to stand at −70° C. The mixture was then centrifuged for 20 minutes at 10,000×g, and the resulting precipitate was washed with 70% ethanol and dried at reduced pressure. The dried preparation was again dissolved in 500 μL TE buffer and repeatedly purified on an oligo dT cellulose column. The resulting poly (A) $^+$RNA from the roots of the low temperature treated *Cucurbita ficifolia* Bouche was used to prepare a cDNA library for PCR and a cDNA library for isolating the full-length gene.

(2) Preparation of cDNA Library for PCR

The cDNA library was prepared using a Marathon cDNA Amplification Kit (by Clontech). The poly (A) $^+$RNA from the roots of the *Cucurbita ficifolia* Bouche obtained in (1) was used as template, and reverse transcriptase and modified lock-docking oligo(dT) primer with two degenerate nucleotide positions at the 3, end were used to synthesize double-stranded cDNA according to the method of Gubler, Hoffman, et al (Gene, 25, 263-269 (1983)).

A Marathon cDNA adapter (the 5' end phosphorylated to facilitate binding to both ends of the ds cDNA with T4 DNA ligase) was ligated to both ends of the resulting cDNA. The resulting adapter-linked cDNA was used as a *Cucurbita ficifolia* Bouche root-derived cDNA library for PCR.

(3) Design of PCR Primers

The base sequences of arginine decarboxylase, S-adenosylmethionine decarboxylase, and spermidine synthase genes already isolated from plants or mammals were compared.

Regions with extremely highly conserved homology were selected to synthesize DNA oligomers (sequence primers I through VI).

```
SPDS primer I (SEQ ID NO. 7):
5'-GTTTTGGATGGAGTGATTCA-3'

SPDS primer II (SEQ ID NO. 8):
5'-GTGAATCTCAGCGTTGTA-3'

SAMDC primer III (SEQ ID NO. 9):
5'-TATGTGCTGTCTGAGTCGAGC-3'

SAMDC primer IV (SEQ ID NO. 10):
5'-GCTAAACCCATCTTCAGGGGT-3'

ADC primer V (SEQ ID NO. 11):
5'-GGGCT(T/G)GGA(G/A)T(G/C)GACTA(C/T)-3'

ADC primer VI (SEQ ID NO. 12):
5'-(T/C)CC(A/G)TC(A/G)CTGTC(G/A)CA(G/C)GT-3'
```

(4) Amplification by PCR

The cDNA library for PCR obtained in (2) was used as template, and the sequence primers designed in (3) were used for PCR. The PCR steps involved 5 cycles of 30 seconds at 94° C., 1 minute at 45° C., and 2 minutes at 72° C., followed by 30 cycles of 30 seconds at 94° C., 1 minute at 55° C., and 2 minutes at 72° C.

(5) Agarose Gel Electrophoresis

Electrophoresis of the PCR amplified products on 1.5% agarose was followed by ethidium bromide staining of the electrophoresed gel and detection of amplified bands on a UV transilluminator.

(6) Verification and Recovery of PCR Amplified Products

The detected amplified bands were verified and were cut out of the agarose gel with a razor. The pieces of gel were transferred to 1.5 mL microtubes, and the DNA fragments were isolated and purified from the gel using a QIAEX II Gel Extraction Kit (by QIAGEN). The recovered DNA fragments were subcloned to the pGEMT cloning vector (by Promega), transformed with *E. coli*, and then used to prepare plasmid DNA in the usual manner.

(7) Sequencing

The sequencing of the sequences inserted into the plasmids were determined by the dideoxy method (Messing, Methods in Enzymol., 101, 20-78 (1983)). Three types of SPDS gene, one type of SAMDC gene, and two types of ADC gene were isolated.

(8) Detection of Homology

A homology search of the base sequences of these genes against a database of known gene base sequences revealed that the SPDS genes had 70% homology with known plant-derived SPDS genes, that the SAMDC gene had at least 70% homology with known plant-derived SAMDC genes, and that the ADC genes had at least 67% homology with known plant-derived ADC genes.

(9) Obtaining Full-Length Genes

Full-length genes were obtained by plaque hybridization. cDNA libraries were prepared using the ZAP-cDNA Synthesis Kit (Stratagene). The poly (A) +RNA from the roots of *Cucurbita ficifolia* Bouche obtained in (1) was used as template, and oligo(dT) primers were used to synthesize double-stranded cDNA according to the method of Gubler, Hoffman, et al (Gene, 25, 263-269 (1983)).

EcoRI adapters (with internal XhoI and SpeI sites) were ligated to both ends of the resulting cDNA, which was digested with XhoI, the fragments were ligated to the EcoRI and XhoI sites in the arm of a λ phage vector (λ ZAPII) and were then packaged using an in vitro packaging kit (Gigapack Gold, by Stratagene), and the *E. coli* SURE strain (OD 660=0.5) was infected, giving numerous recombinant λ phages. These were used as the *Cucurbita ficifolia* Bouche root-derived cDNA library. The library size was $8.0 \times 10^6$.

To prepare probe, the insert cDNA was isolated and purified from the plasmid DNA of the SPDS, SAMDC, and ADC genes prepared in (6), the resulting cDNA was used as template, and a Random Primed DNA Labeling Kit (USB) was used to prepare $^{32}$P labeled probe. The resulting $^{32}$P labeled cDNA was used as probe.

The phages used to construct the *Cucurbita ficifolia* Bouche root-derived cDNA library were used to infect *E. coli* for amplification on LB agar medium, and about 50,000 copies of phage DNA were transferred to nylon membranes (Hy-Bond-N, by Pharmacia).

The nylon membranes on which the phage DNA was transferred were transferred onto filter paper containing alkali denaturation solution (0.5 M NaOH, 1.5 M NaCl), the membranes were allowed to stand for 4 minutes, and they were then transferred onto filter paper containing neutralization solution (0.5 M Tris-HCl, 1.5 M NaCl, pH 8.0) and allowed to stand for 5 minutes. The membranes were washed with 2×SSC (0.3 M NaCl, 0.03 M trisodium citrate), and the DNA was then fixed on the membranes using Stratalinker (by Stratagene). The nylon membranes on which the DNA had been fixed were placed in hybridization solution (50% formamide, 0.5% SDS, 6×SSPE (3 M NaCl, 0.2 M $NaH_2PO_4$, 20 mM EDTA-2Na, pH 7.4), 5×Denhardt's solution (0.1% Ficoll, 0.1% polyvinyl pyrrolidone, 0.1% bovine serum albumin), 50 μg/mL denatured salmon sperm DNA) to bring about pre-hybridization for 3 hours at 42° C., the cDNA probe that had been prepared was added, and hybridization was brought about for 18 hours at 42° C. The membranes were then taken out and washed for 1 to 2 hours at 42° C. with solution containing 2×SSC, 1×SSC, 0.5×SSC, and 0.1×SSC. The membranes were dried and were then placed on X-ray film and exposed over night.

Positive clones hybridized with probe obtained from the SPDS, SAMDS, and ADC gene fragments could thus be selected.

Plasmid clones with cDNA inserts were prepared by in vivo excision from the phage DNA of the positive clones. The in vivo excision followed the method in the ZAP-cDNA Synthesis Kit (Stratagene).

A 200 μL amount of each phage solution containing the SPDS, SAMDC, and ADC genes respectively, 200 μL *E. coli* XL1-Blue suspension, and 1 μL of helper phage R408 suspension were mixed, the mixtures were incubated for 15 minutes at 37° C., 3 mL of 2×YT medium was added for 2 hours of shaking culture at 37° C., the cultures were treated for 20 minutes at 70° C. and centrifuged (10 minutes at 4,000×g), and the supernatant was recovered. 30 μL of the resulting supernatant and 30 μL *E. coli* SURE suspension were mixed, the mixture was incubated for 15 minutes at 37° C., and several μL was used to inoculate LB agar medium containing 50 ppm ampicillin for culture over night at 37° C. The *E. coli* forming colonies contained plasmids with cDNA inserts. The base sequences of the inserted sequences in the plasmids were sequenced by the dideoxy method (Messing, Methods in Enzymol., 101, 20-78 (1983)). The results showed that the plasmids contained start codons.

The resulting full-length spermidine synthase genes from *Cucurbita ficifolia* Bouche were designated FSPD1 (SEQ ID NOS. 1 and 2), the S-adenosylmethionine decarboxylase gene was designated FSAM24 (SEQ ID NOS. 3 and 4), and the arginine decarboxylase gene was designated FADC76 (SEQ ID NOS. 5 and 6).

The amino acids of the resulting FSPD1 were compared with those of known plant-derived spermidine synthase genes (Table 1). The results of Table 1 show that FSPD1 from *Cucurbita ficifolia* Bouche roots had high homology at the amino acid level with other plant-derived SPDS genes.

TABLE 1

Comparison of *Cucurbita ficifolia* Bouche FSPD1 gene and other SPDS genes

| Plant | Origin | Amino acid homology (%) |
|---|---|---|
| *Arabidopsis thaliana* | | 83.8 |
| *Nicotiana sylvestris* | Leaves | 82.1 |
| *Hyoscyamus niger* | roots | 86.5 |

The amino acids of the resulting FSAM24 were compared with those of known plant-derived S-adenosylmethionine decarboxylase genes (Table 2). The results of Table 2 show that FSAM24 from *Cucurbita ficifolia* Bouche roots had high homology at the amino acid level with other plant-derived SAMDC genes.

TABLE 2

Comparison of *Cucurbita ficifolia* Bouche FSAM24 gene and other SAMDC genes

| Plant | Origin | Amino acid homology (%) |
|---|---|---|
| *Arabidopsis thaliana* | seedlings | 66.3 |
| *Spinacia oleracea* | | 63.3 |
| *Solanum tuberosum* | | 68.2 |
| *Pisum sativum* | undifferentiated-calli | 65.2 |

The amino acids of the resulting FADC76 were compared with those of known plant-derived arginine decarboxylase genes (Table 3). The results of Table 3 show that FADC76 from *Cucurbita ficifolia* Bouche roots had high homology at the amino acid level with other plant-derived ADC genes.

TABLE 3

Comparison of *Cucurbita ficifolia* Bouche FADC76 gene and other ADC genes

| Plant | Origin | Amino acid homology (%) |
|---|---|---|
| *Lycopersicon esculentum* | fruit | 77.1 |
| *Nicotiana sylvestris* | | 75.4 |
| *Arabidopsis thaliana* | | 70.7 |
| *Pisum sativum* | fruit | 70.6 |

Example 2

Preparation of Transgenic *Arabidopsis thaliana*

(1) Preparation of Expression Construct

Figure 1:
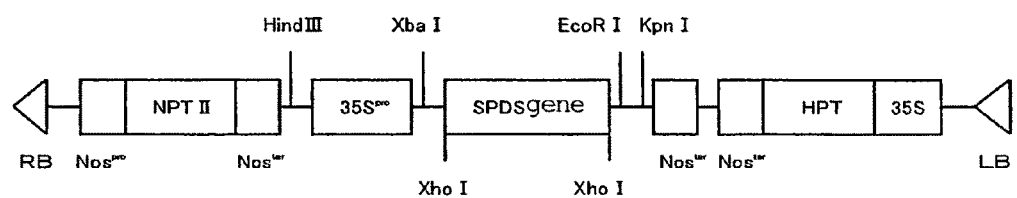
Figure 1:
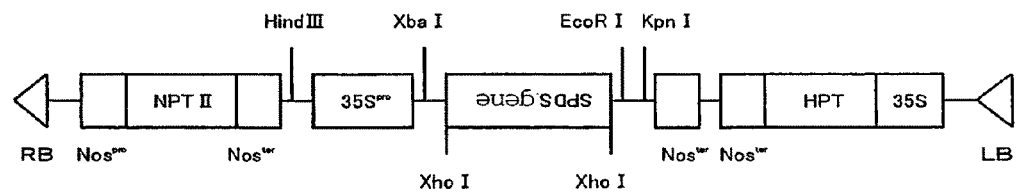
Figure 2:
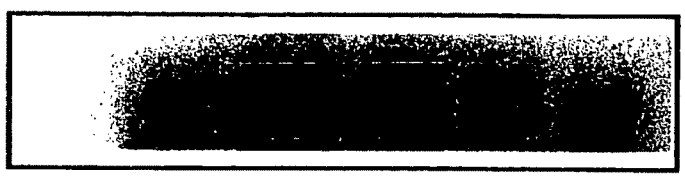

The FSPD1 polyamine metabolism-related enzyme gene given in SEQ ID NO. 1 was cleaved with XhoI in such a way that the entire reading frame of the base sequence was included, and the fragment was purified by the glass milk method. pGEM-7Zf (Promega) was then cleaved with XhoI, and the FSPD1 fragments were subcloned in the sense and antisense directions. The FSPD1 fragments were again cleaved with the XbaI and KpnI restriction enzymes at the multicloning site of pGEM-7Zf, and were subcloned in the sense and antisense direction to the binary vector pBI101-Hm2 to which the 35S promoter had been ligated. The resulting plasmid was designated pBI35S-FSPD1. The structure of this expression construct is given in FIG. 1. Transformed *E. coli* JM109 was designated *Escherichia coli* JM109/pBI35S-FSPD1 +/−.

The polyamine metabolism-related enzyme gene FSAM24 given in SEQ ID NO. 3 was cleaved with NotI in such a way that the entire reading frame of the base sequence was included, and the ends were blunted. The fragments were subcloned to the binary vector pBI101-Hm2 to which the (blunted) 35S promoter had been ligated. The resulting plasmid was designated pBI35S-FSAM24 +/−. Transformed *E. coli* JM109 was designated *Escherichia coli* JM109/pBI35S-FSAM24 +/−.

The polyamine metabolism-related enzyme gene FADC76 given in SEQ ID NO. 5 was cleaved with NotI in such a way that the entire reading frame of the base sequence was included, and the ends were blunted. The fragments were subcloned to the binary vector pBI101-Hm2 to which the (blunted) 35S promoter had been ligated. The resulting plasmid was designated pBI35S-FADC76 +/−. Transformed *E. coli* JM109 was designated *Escherichia coli* JM109/pBI35S-FADC76 +/−.

(2) Introduction of Plasmids to *Agrobacterium*

The *E. coli* pBI35S-FSPD1 +/−, *E. coli* pBI35S-FSAM24 +/−, or *E. coli* pBI35S-FADC76 +/− obtained in (1) and the *E. coli* HB101 strain with the helper plasmid pRK2013 were cultured for 1 night at 37° C. on LB medium containing 50 mg/L kanamycin, and the *Agrobacterium* C58 strain was cultured for 2 nights at 37° C. on LB medium containing 50 mg/L kanamycin. Cells were harvested from 1.5 mL of each culture in Eppendorf tubes and then washed with LB medium. The cells were suspended in 1 mL of LB medium, 100 μL each of the three types of cells were mixed to inoculate LB agar medium and cultured at 28° C. to allow the plasmids to be conjugated with the *Agrobacterium* (tripartite conjugation). After 1 or 2 days, portions were scraped with a platinum loop and smeared on LB agar medium containing 50 mg/L kanamycin, 20 mg/L hygromycin and 25 mg/L chloramphenicol. After 2 days of culture at 28° C., single colonies were selected. The resulting transformants were designated C58/pBI35S-FSPD1 +/−, C58/pBI35S-FSAM24 +/−, and C58/pBI35S-FADC76 +/−. Transgenic *Arabidopsis thaliana* was prepared by reduced pressure infiltration ((3) through (6) below) or callus regeneration ((7) through (12) below).

(3) Cultivation of *Arabidopsis thaliana*

Potting commercial nursery soil Metromix (Hyponex Japan) was placed in plastic pots, the surfaces were covered with netting mesh, and 2 to 5 seeds (donated by Professor Takayuki Kohchi of Nara Institute of Science and Technology Graduate University) of *Arabidopsis thaliana* (referred to below as the "Columbia strain" or "wild type") were inoculated through the interstices of the mesh. The pots were placed for 2 days at 4° C. in a low temperature chamber to germinate, and were then transferred for cultivation under 22° C. long-day conditions (16 hour long day/8 hour night). After about 4 to 6 weeks, lateral shoots were induced by top pruning plants in which the main axis flower stalk was extended to between 5 and 10 cm. After about 1 to 2 weeks of top pruning, the plants were infected with *Agrobacterium*.

(4) Preparation of *Agrobacterium* Suspension 2 days before infection, the *Agrobacterium* prepared in (2) above was used to inoculate 10 mL LB medium containing antibiotics (50 μg/mL kanamycin, 20 μg/mL hygromycin) for 24 hours of shaking culture at 28° C. Portions of the culture were transferred to 1000 mL LB medium containing antibiotics (50 μg/mL kanamycin, 20 μg/mL hygromycin) for about another 24 hours of shaking culture at 28° C. (to an $OD_{600}$ of between 1.2 and 1.5). Cells were harvested from the culture at ambient temperature and were resuspended in suspension medium for infiltration (0.5×MS salt, 0.5× Gamborg B5 vitamin, 1% sucrose, 0.5 g/L MES, 0.44 μM benzylaminopurine, 0.02% Silwet-77) to an $OD_{600}$ of between 0.8 and 1.

(5) *Agrobacterium* Infection

The potting soil in the pots of *Arabidopsis thaliana* prepared in (3) above was watered to prevent the potting soil from absorbing the *Agrobacterium* suspension prepared in (4) above. Approximately 200 to 300 mL of the *Agrobacterium* suspension was placed in 1000 mL beakers, and the potted *Arabidopsis thaliana* was turned upside down to dip the plants in the suspension. The beakers in which the pots had been placed were put into a dessicator, which was suctioned with a vacuum pump to about −0.053 MPa (400 mmHg), and the plants were then allowed to stand for about 10 minutes. The negative pressure was gradually released, the plants were then taken out of the *Agrobacterium* suspension, the excess *Agrobacterium* suspension was wiped off with a Kimtowel, and the pots were placed on their sides in deep-bottomed trays. A small amount of water was introduced, and the plants were covered with saran wrap. The plants were allowed to stand in this manner for about 1 day. The saran wrap was then removed, and the pots were placed upright and irrigation was stopped for about 1 week. The potting commercial nursery soil was then gradually watered, and seeds were harvested from matured pods for about 3 to 5 weeks. The harvested seeds were strained through a tea strainer to eliminate debris and husks, and the seeds were placed in a dessicator and thoroughly dried.

(6) Obtaining Transformed Plants

100 μL (about 2000) seeds obtained in (5) above were transferred to 1.5 mL Eppendorf tubes and soaked for 2 minutes in 70% ethanol and 15 minutes in 5% sodium hypochlorite solution, and the seeds were finally washed five times with sterile water to disinfect the seeds. The disinfected seeds were transferred to 15 mL falcon tubes, about 9 mL of 0.1% aseptic agar solution was added, and the contents were vigorously mixed. A 0.1% agar mixture of seeds was evenly spread on selection medium (1×MS salt, 1× Gamborg B5 vitamin, 1% sucrose, 0.5 g/L MES, 0.8% agar, 100 mg/L carbenicillin, 50 mg/L kanamycin, 40 mg/L hygromycin, 8 g/L Phytagar, pH 5.7) like plating the phages. The plates were dried for about 30 minutes in a clean bench, a 4° C. low temperature treatment was performed for 2 days, the plates were transferred to a 22° C. growth chamber, and transformants with antibiotic resistance were selected. Plants with about 3 to 5 true leaves were again transferred to fresh selection medium and cultivated until 4 to 6 true leaves had grown. Transformants with antibiotic resistance (T1) were planted in pots filled with commercial nursery soil and acclimated under humid conditions for about 5 to 7 days. After acclimation, the plants were cultivated at 23° C. under long day conditions (16 hour long days/8 hour nights). The resulting transgenic plants (T1) and plants T2 grown from seeds (T2) obtained from the transgenic plants were analyzed for genes introduced by PCR or Southern hybridization and their levels of expression by Northern hybridization were analyzed, so as to confirm that the target polyamine metabolism-related enzyme genes had been incorporated in a consistent manner and that transformants had been expressed. Seeds T3 were also harvested from the plants T2, and antibiotic resistance tests (segregation analysis) were conducted to obtain homozygotes (T2) based on the proportion in which transformants appeared. Seeds T2 and seeds T3 obtained from the homozygotes (T3 homozygous cell line) were used in the following tests.

(7) Aseptic *Arabidopsis thaliana* Cultivation 10 seeds (donated by Professor Atsuhiko Shinmyo of Nara Institute of Science and Technology Graduate University) of the *Arabidopsis thaliana* Wassilewskija strain (referred to below as the WS strain) were introduced into 1.5 mL tubes, 1 mL of 70% ethanol was added, and the seeds were allowed to stand for 3 minutes. The seeds were then dipped for 3 minutes in disinfecting solution (5% sodium hypochlorite, 0.02% Triton X-100), washed 5 times with sterilized water, and then planted in MSO plates (4.6 g Murashige-Skoog mineral salts, 10 g sucrose, 1 mL/L 1000× vitamin stock, pH 6.2). The plates were allowed to stand for 2 days at 4° C. to carry out low temperature treatment, and they were then cultured for 21 days in plant incubators (MLR-350HT, by Sanyo) under conditions involving long days (16 hour long days, 8 hour nights) at 22° C. and a light intensity of 6000 lux. To improve the infection efficiency, the plants were again aseptically plucked out, the roots were spread out on the surface of fresh MSO plates, and the culture was continued for another 2 days.

(8) *Agrobacterium* Infection

Several roots of the WS strain cultured for 21 days above were arranged and cut with a scalpel to between about 1.5 and 2.0 cm, and they were placed alongside each other on CIM plates (MSO plates supplemented with 2,4-dichlorophenoxyacetic acid to a final concentration of 0.5 μg/mL and kinetin to a final concentration of 0.05 μg/mL). Samples which had been cultured for 2 days at a light intensity of 3000 lux in 16 hours of light/8 hours of darkness and diluted 3-fold with MS dilution solution (6.4 g/L Murashige-Skoog mineral salts, pH 6.3) were aliquoted in 1 mL portions to tubes, and slices of the roots on which callus was forming were dipped for 10 minutes in the tubes. The slices were placed on doubled disinfected filter paper, the excess moisture was removed, and the slices were arranged on fresh CIM plates for two days of co-cultivation under the same conditions.

(9) Disinfection

Slices on which the strain had grown enough to become visible to the naked eye were transferred to a disinfection solution (MS diluting solution supplemented with claforan to a final concentration of 200 μg/mL) and gently shaken to wash them for 60 minutes. These operations were repeated 5 times, the moisture was removed on sterilized filter paper, and the slices were placed on SIMC plates (MSO plates supplemented with 2-ip to a final concentration of 5 μg/mL, IAA to a final concentration of 0.15 μg/mL, and claforan to a final concentration of 500 μg/mL) for 2 days of culture at a light intensity of 6000 lux in 16 hours of light/8 hours of darkness.

(10) Selection of Transformants

The slices cultured for 2 days above were transferred to SIMCS plates (SIMC plates supplemented with hygromycin B to a final concentration of 4.6 U/mL) for culture at a light intensity of 6000 lux in 16 hours of light/8 hours of darkness. The slices were subsequently transferred to fresh SIMCS plates every week. The transformed slices continued to be grown, forming dome-shaped callus, but slices that had not been transformed turned brown. After about 2 weeks, the callus of the transformants turned green. After about 1 month, leaves formed, and after that rosettes formed.

(11) Regeneration of Transformants

The roots of plants with rosette leaves were cut with a knife or scalpel to leave out the callus and were inserted so as to ride gently on RIM plates. After 8 to 10 days, those on which several roots of about 1 to 2 cm had formed were planted using tweezers and cultivated in rock wool minipots (by Nitto Boseki) soaked with mineral salt medium (5 mM $KNO_3$, 2.5 mM K-phosphate buffer (pH 5.5), 2 mM $MgSO_4$, 2 mM $Ca(NO_3)_2$, 50 µM Fe-EDTA, 1000× microelements (70 mM $H_3BO_3$, 14 mM $MnCl_2$, 0.5 mM $CuSO_4$, 1 mM $ZnSO_4$, 0.2 mM $NaMoO_4$, 10 mM NaCl, 0.01 mM $CoCl_2$) 1 mL/L). After flowering and the formation of pods, the plants were transplanted to soil prepared by mixing pearlite and vermiculite (by TES) in a 1:1 ratio, and then soaked with mineral salt media. After about 1 month, several hundred seeds of each strain were obtained. These were subsequently called T2 seeds.

(12) Obtaining Antibiotic Resistant Strains

About 100 T2 seeds were sterilized in the same manner as in (7) and used to inoculate MSH plates. Hygromycin B-resistant strains germinated in a proportion of about 3:1.

(13) DNA Extraction and Southern Hybridization

The germinated T2 seeds above were transplanted using tweezers to rock wool minipots soaked with mineral salts and cultured at a light intensity of 6000 lux and a temperature of 22° C. in 16 hours of light and 8 hours of darkness. After 2 weeks, the top soil was cut away with a scalpel to allow the surface of the rock wool to be stroked with a knife, and samples were immediately frozen with liquid nitrogen. The samples were finely milled in a mortar and pestle in the presence of liquid nitrogen, 3 mL of DNA extraction buffer (200 mM Tris-HCl (pH 8.0), 100 mM EDTA-2Na, 1% N-lauroylsarcosine sodium, 100 Hg/mL proteinase K) was added per gram, and the ingredients were thoroughly mixed. The mixture was incubated for 1 hour at 60° C. and then centrifuged (10 minutes at 10,000×g), and the supernatant was filtered through mira cloth and transferred to a fresh tube. It was extracted three times with phenol:chloroform:isoamyl alcohol (25:24:1) and then precipitated in ethanol. The precipitate was dissolved in TE buffer. 20 µg each of genomic DNA was obtained from about 2.0 g of each of the plants. 1 µg of DNA was cleaved with the EcoRI and HindIII restriction enzymes for 1% agarose electrophoresis and Southern hybridization.

Seeds of untransformed WS strain were germinated and allowed to grow, DNA was similarly extracted from the plants and digested with the EcoRI and HindIII restriction enzymes for 1% agarose electrophoresis and Southern hybridization. FSPD1, FSAM24, and FADC76 gene fragments were used as hybridization probes.

Southern hybridization was performed according to the method in *Molecular Cloning, a Laboratory Manual* (Chapter 9, pp. 31-58 (Cold Spring Harbor (1989))). Specifically, electrophoresis of the DNA material on 1% agarose gel was followed by alkali denaturation and Southern blotting overnight on nylon membranes (HyBond-N, by Amersham). The DNA was fixed by 3 minutes of irradiation with a UV transilluminator (254 nm). The membranes were pre-hybridized for 2 hours at 50° C. in 5 mL of pre-hybridization buffer (5×Denhardt's, 6×SSC, 0.1% SDS, 10 µg/mL salmon sperm DNA) Probes were added for hybridization over night at 50° C. After the hybridization, the membranes were washed twice for 10 minutes with washing solution containing 2×SSC and 0.1% SDS, and were then washed twice for 30 minutes at 50° C. with the same solution. The membranes were dried and exposed over night at −80° C. in cassettes filled with X-ray film (by Kodak) to take autoradiographs. The patterns of the signals detected by Southern hybridization were compared for untransformed strains (1), transformants containing FSPD1, FSAM24, and FADC76 (2), and transformants containing only the vector (3).

In addition to the endogenous signal shared in common by (1), (2), and (3), specific signals were observed in EcoRI digests and HindIII digests of (2), confirming that the target gene had been incorporated in (2).

Example 3

Northern Blotting Analysis

In order to ascertain whether the target gene was actually expressed in the T2 transformants obtained in Example 2, Northern blotting was performed in the following manner.

Total RNA was extracted from untransformed wild type (WT) and T2 transformant (cell lines: TSP-14, 15, 16, 17, 19) rosette leaves. The RNA was extracted in the same manner as in Example 2. 10 µg of the resulting total RNA was electrophoresed on 1.5% formaldehyde agarose gel and blotted over night on HyBond N nylon membranes. The RNA was fixed with a UV crosslinker and then pre-hybridized for 2 hours at 42° C. in pre-hybridization buffer (50% formamide, 5×SSPE, 5×Denhardt's, 0.1% SDS, 80 µg/mL salmon sperm DNA, pH 7.0). Probes were prepared with the use of $^{32}$P-dCTP and a random label kit (by Amersham) from the cDNA of the transformed *Cucurbita ficifolia* Bouche SPDS gene fragment. The probe was added to the pre-hybridization mixture for hybridization over night at 42° C. After the hybridization, the membranes were washed twice for 30 minutes at 55° C., beginning with a washing solution containing 2×SSC and 0.1% SDS, and ending with a washing solution containing 0.1×SSC and 0.1% SDS. Autoradiographs of the membranes were taken using X-ray film (Kodak).

The results of Northern blotting are given in FIG. 9. The results in FIG. 9 show that no expression of the exogenous *Cucurbita ficifolia* Bouche SPDS gene was detected in the wild type (WT), but that the *Cucurbita ficifolia* Bouche SPDS gene (FSPD1) was expressed in extremely high levels in all the T2 transformants.

Example 4

Evaluation of Polyamine Content (1) Selection of Cell Lines Containing Target Gene Cell lines were selected upon confirmation that the target gene had been introduced by PCR (or Southern analysis) and Northern analysis of the transformants prepared in Example 3, resulting in the selection of cell lines TSP-114, 115, 116, 117, 119, 131, 132, 151, 152, 221 and 222. Polyamine content was determined with respect to TSP-114 to 115 in which FSPD1 was introduced, TSP-131 and 132 in which FSAM24 was introduced, TSP-151 and 152 in which FADC76 was introduced, TSP-221 and 222 in which FSPD1 was introduced in antisense direction.

(2) Analysis of Polyamine Content

Approximately 0.1 to 0.3 g of rosette leaves (or true leaves) from the transgenic plants (TSP) and the wild type plants (WT), which were cultivated at the same time, were sampled, frozen and stored in plastic vials which could be tightly sealed. Dilution internal standard solution (1,6-hexanediamine, internal standard content=7.5 nmol) and 5% perchloric acid aqueous solution (5 to 10 mL per 1.0 g specimen fresh weight) were added to the sampled specimen, and was thoroughly ground down and extracted using an omnimixer at room temperature. The ground solution was centrifuged at 4° C., 35,000×g for 20 minutes, and the supernatant was collected and was taken as the free polyamine solution. Four hundred microliters of free polyamine solution, 200 μL of saturated sodium carbonate aqueous solution, and 200 μL of dansyl chloride/acetone solution (10 mg/mL) were added into a microtube with a screw cap, and lightly mixed. After firmly closing with a tube stopper and covering with aluminum foil, dansylation was conducted by heating for 1 hour in a 60° C. water bath. After allowing the tube to cool, 200 μL of proline aqueous solution (100 mg/mL) was added and mixed. The tube was covered with aluminum foil and heated again for 30 minutes in a water bath. After standing to cool, the acetone was removed by spraying nitrogen gas, and then 600 μL of toluene was added and vigorously mixed. After allowing the tube to stand quietly and separate into 2 phases, 300 μL of toluene in the upper layer was separated into a microtube. The toluene was completely removed by spraying nitrogen gas. 100 to 200 μL of methanol was added to the tube and the dansylated free polyamine was dissolved. The free polyamine content of putrescine, spermidine and spermine was assayed by the internal standard method using high performance liquid chromatography connected to a fluorescence detector (exitation wavelength is 365 nm, emission wavelength is 510 nm). A μBondapak C18 (manufactured by Waters, Co.: 027324, 3.9×300 mm, particle size 10 μm) was used for the HPLC column. The polyamine content in the specimens was calculated by deriving the peak areas of the polyamine and internal standard from the HPLC charts of the standard solution and specimens. The results are indicated in Table 4.

TABLE 4

| Cell line | Free polyamine content (nmolg$^{-1}$fw) | | | |
|---|---|---|---|---|
| | Putrescine | Spermidine | Spermine | Total polyamines |
| Wild type: WT | 5.41 ± 3.74 | 108.99 ± 12.63 | 11.95 ± 2.92 | 126.35 ± 16.04 |
| TSP-114 | 6.06 ± 3.04 | 149.96 ± 11.64 | 23.68 ± 2.06 | 179.70 ± 20.82 |
| TSP-115 | 8.33 ± 2.05 | 175.76 ± 16.30 | 21.53 ± 1.29 | 205.62 ± 20.82 |
| TSP-116 | 10.66 ± 3.98 | 182.94 ± 23.73 | 21.36 ± 6.48 | 214.96 ± 29.41 |
| TSP-117 | 12.40 ± 3.89 | 177.45 ± 12.70 | 13.33 ± 1.07 | 203.18 ± 16.77 |
| TSP-119 | 7.82 ± 3.55 | 169.13 ± 36.97 | 21.59 ± 3.10 | 198.54 ± 41.49 |
| TSP-131 | 7.02 ± 3.10 | 165.55 ± 11.54 | 19.11 ± 2.00 | 191.68 ± 14.66 |
| TSP-132 | 8.34 ± 3.65 | 162.34 ± 24.01 | 19.04 ± 7.01 | 189.72 ± 29.89 |
| TSP-151 | 10.99 ± 3.82 | 159.39 ± 12.45 | 18.98 ± 1.51 | 189.36 ± 15.89 |
| TSP-152 | 11.98 ± 3.72 | 158.99 ± 12.93 | 18.54 ± 2.90 | 189.51 ± 16.54 |
| TSP-221 | 4.89 ± 1.69 | 74.11 ± 8.57 | 7.37 ± 0.16 | 86.36 ± 8.08 |
| TSP-222 | 4.99 ± 1.00 | 71.31 ± 8.77 | 7.11 ± 1.03 | 83.41 ± 9.13 |

Table 4 shows that cell lines TSP-114, 115, 116, 117, 119, 131, 132, 151 and 152 in which the polyamine metabolism-related enzyme gene was introduced in sense direction had significantly higher levels of putrescine, spermidine and spermine contents than the wild type (WT), and that the total polyamine content was also significantly higher than in the wild type (WT). In particular, spermidine and spermine contents were increased remarkably. In addition, TSP-221 and 222 in which the polyamine metabolism-related enzyme gene was introduced in antisense direction had significantly lower levels of, in particular, spermidine and spermine contents than the wild type (WT), and that the total polyamine content was also significantly lower than in the wild type (WT).

The results showed that the introduction of the polyamine metabolism-related enzyme gene into plants in sense or actisence direction allowed the polyamine content to be increased or decreased. The results showed that the introduction of the polyamine metabolism-related enzyme gene into plants allowed the polyamine content to be controlled through the manipulation of polyamine metabolism.

Example 5

Evaluation of Various Types of Morphogenesis (1) Evaluation of the Number of Stems, Leaves, Flowers and Pods Seeds of T3 transgenic plants obtained in example 2 (cell lines: TSP-16-1, 16-2, in which FSPD1 was introduced in the sense direction) and of a wild type plant (WT: Columbia strain) were planted in plastic pots containing Metromix potting soil (manufactured by Hyponex Japan, Co.). After planting and treating at a low temperature of 4° C. for approximately 2 days, the pots were placed in plastic vats, and cultivation under long day conditions (day length of daylight/dark: 16 hours/8 hours) at 23° C. was started. The plants were grown for 15 weeks after planting. After growing, the number of stems (flower stalks) per individual plants in each line was investigated. Thirty individual plants of each line were studied. The results are indicated in FIG. 3.

Figure 3:
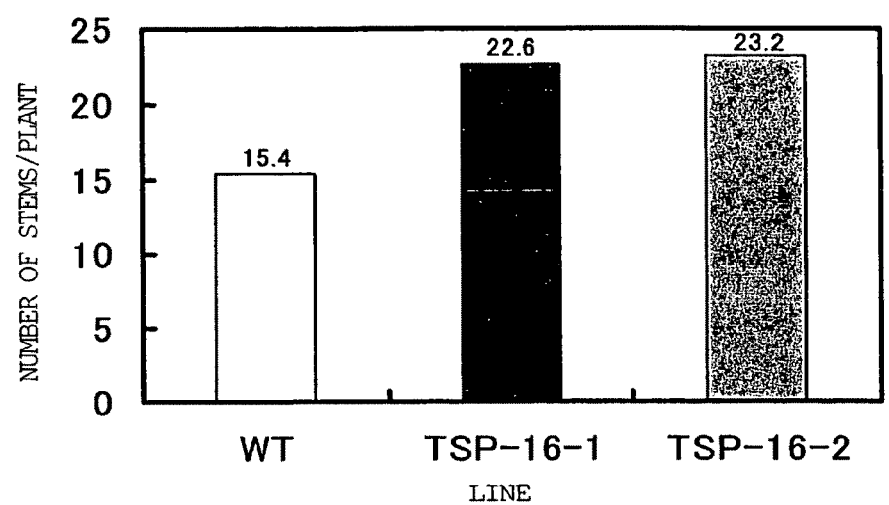
Figure 4:
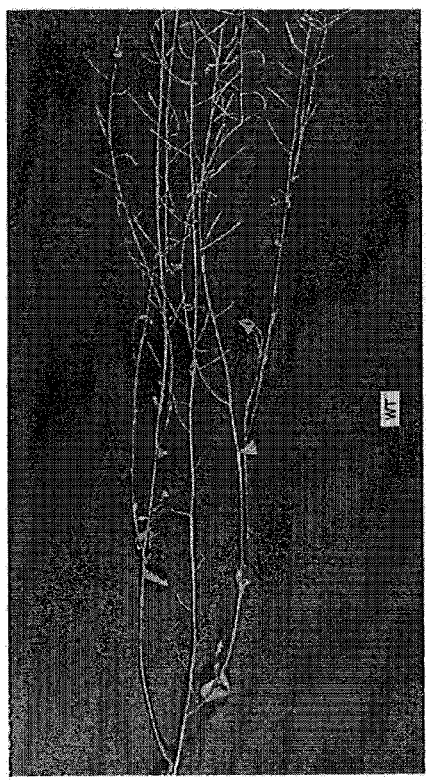
FIG. 4 is a photograph indicating a comparison of the number of stems, leaves, flowers, ovaries and seeds of a wild type plant and of a plant in which a polyamine metabolism-related enzyme gene has been introduced.
Figure 4:

The results of FIG. 3 demonstrate that compared to the wild type plant, the T3 transgenic plants (TSP-16-1, 16-2) had a significant increase in the number of stems by approximately 7 to 8 stems per plant. Further, it was demonstrated that by increasing the number of stems per plant, the number of leaves (cauline leaves), flowers and pods (ovaries) also increased notably. The plant habit of the wild type plant and TSP-16-1 are indicated in FIG. 4.

(2) Evaluation of the Number of Main Stems and Side Stems

From the results of (1) it was confirmed that the number of stems significantly increased in the T3 transgenic plants compared to the wild type plant. Then, because the stems of *Arabidopsis thaliana* may be divided into main stems (main flower stalks), and side stems (side flower stalks), the decision was made to study the respective numbers of main and side stems. Seeds of T3 transgenic plants (cell lines: TSP-161B, 162B, in which FSPD1 was introduced in the sense direction) and of a wild type plant (WT: Columbia strain) were planted in plastic pots containing Metromix potting soil (manufactured by Hyponex Japan, Co.). After planting and treating at a low temperature of 4° C. for approximately 2 days, the pots were placed in plastic vats, and cultivation under long day conditions (day length of daylight/dark: 16 hours/8 hours) at 23° C. was started. The plants were grown for 7 weeks after planting, and from week 7 (day 49) until week 13 (day 91) the respective numbers of main stems (main flower stalks) and side stems (side flower stalks) per individual plant in each line were investigated once per week. Thirty to 32 individual plants of each line were studied. The results are indicated in FIGS. 5 and 6.

Figure 5:
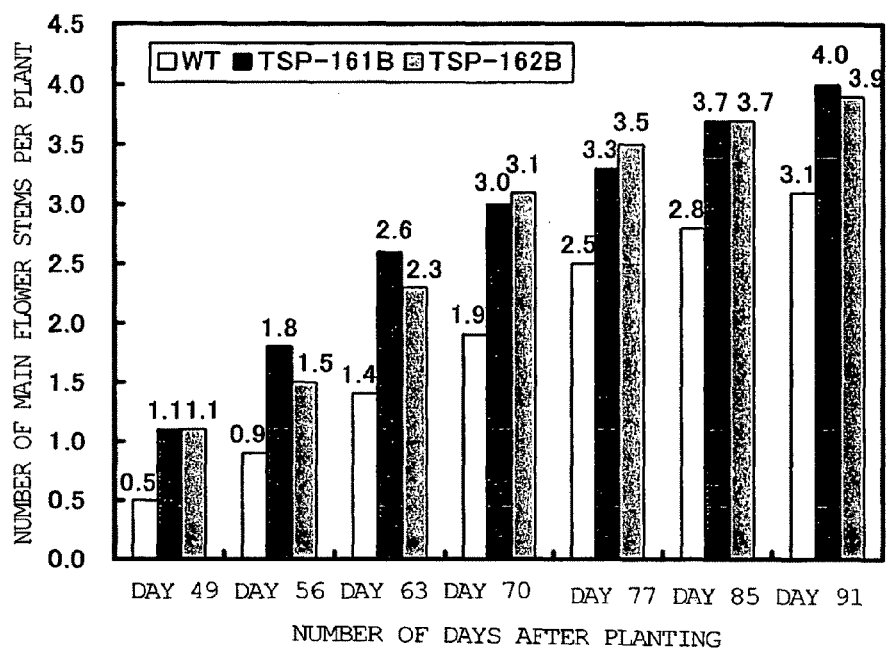
FIG. 5 is a diagram indicating a comparison of the number of main stems of a wild type plant and of a plant in which a polyamine metabolism-related enzyme gene has been introduced.

From the results of FIG. 5, the number of main flower stalks of the T3 transgenic plants increased significantly from day 49 compared to those of the wild type plant, and on day 70 there was an increase of approximately 1 stem per plant in the T3 transgenic plants compared to the wild type plant. The extent of increase in main flower stalks of the T3 transgenic plants and the wild type plant continued about the same until day 91, and the final number of main flower stalks was higher in the T3 transgenic plants than in the wild type plant.

Figure 6:
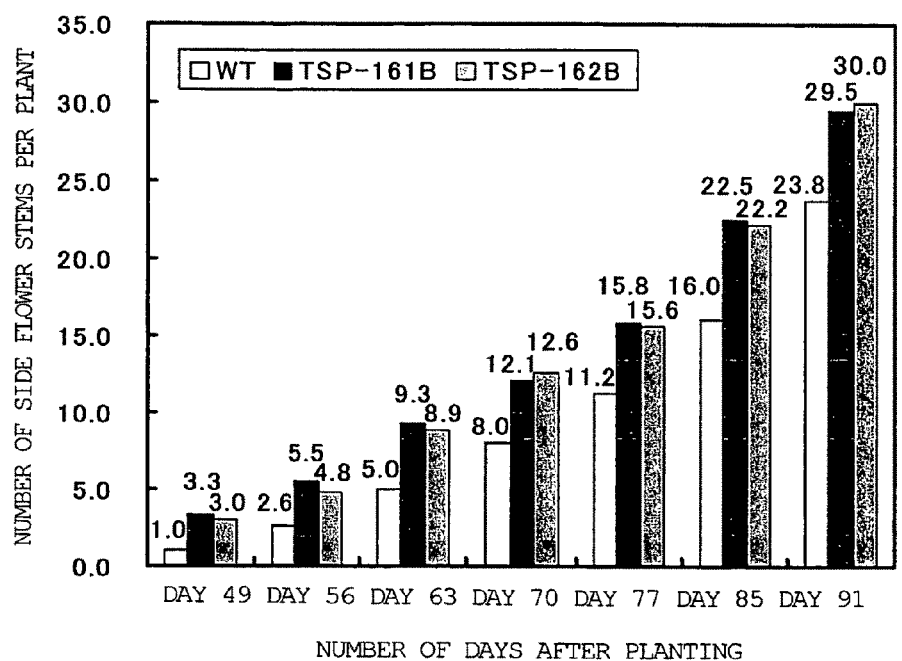
FIG. 6 is a diagram indicating a comparison of the number of side stems of a wild type plant and of a plant in which a polyamine metabolism-related enzyme gene has been introduced.

From the results of FIG. 6, the number of side flower stalks of the T3 transgenic plants increased significantly from day 49 compared to those of the wild type plant, and on day 70 there was an increase of approximately 4 stems per plant in the T3 transgenic plants compared to the wild type plant. On day 91, there was an increase of approximately 5 to 6 stems per plant in the T3 transgenic plants compared to the wild type plant, and the final number of side flower stalks was notably higher in the T3 transgenic plants than in the wild type plant.

(3) Evaluation of the Number of Leaves, Flowers and Pods

From the results of (1), it was confirmed that the number of leaves, flowers and pods (ovaries) significantly increased in the T3 transgenic plants compared to the wild type plant. Then, a detailed study of the number of various organs was conducted. Seeds of a T3 transgenic plant (cell lines: TSP-15-3, 16-1, in which FSPD1 was introduced in the sense direction) and of a wild type plant (WT: Columbia strain) were planted in plastic pots containing Metromix potting soil (manufactured by Hyponex Japan, Co.). After planting and treating at a low temperature of 4° C. for approximately 2 days, the pots were placed in plastic vats, and cultivation under long day conditions (day length of daylight/dark: 16 hours/8 hours) at 23° C. was started. The plants were grown for 67 days after planting, and the number of leaves (cauline leaves), flowers with white petals, and pods (pod length 5 mm or more) per individual (plant) in each line was investigated on day 67. Thirty individual plants of each line were studied. The results are indicated in Table 5.

TABLE 5

| | (Number per plant) | | |
|---|---|---|---|
| Cell line | True leaves | Flowers | Pods |
| Wild type plant (WT) | 10.73 | 9.60 | 6.67 |
| TSP-15-3 | 19.27 | 13.93 | 10.00 |
| TSP-16-1 | 18.33 | 14.27 | 12.67 |

The results of Table 5 demonstrate that T3 transgenic plants have a significantly increased number of true leaves, flowers and pods per plant compared to the wild type plant. After this investigation, the pods of all lines were allowed to mature and dehisce, and the mature seeds were harvested. No significant difference between the T3 transgenic plants and the wild type plant was revealed in the number of seeds per pod, but it was demonstrated that the total number of seeds harvested per plant increased significantly in the T3 transgenic plants as a result of the number of pods increasing about 1.6 to 2.0 times per plant. When conducting a comparative test of the germination rate using seeds from the wild type plant and T4 seeds harvested from the T3 transgenic plants, a high germination rate of 95 to 100% was obtained for both the T4 seeds and the wild type seeds.

(4) Evaluation of Flower Blooming Period, And Ovary (Pod) Development Period

Seeds of the T3 transgenic plant obtained in example 2 (cell lines: TSP-15-3, 16-1, in which FSPD1 was introduced in the sense direction) and of a wild type plant (WT: Columbia strain) were planted in plastic pots containing Metromix potting soil (manufactured by Hyponex Japan, Co.). After planting and treating at a low temperature of 4° C. for approximately 2 days, the pots were placed in plastic vats, and cultivation under long day conditions (day length of daylight/dark: 16 hours/8 hours) at 23° C. was begun. The days to initial bolting and the days to blooming (first flower) were studied in all plants of the various lines, and the plants were studied from the day that the first flower bloomed until the day that the pod (ovary) matured (day to beginning of dehiscence). Thirty individual plants of each line were studied. The results of the days to blooming are indicated in FIG. 7, and the results of the pod (ovary) development period are indicated in Table 6.

Figure 7:
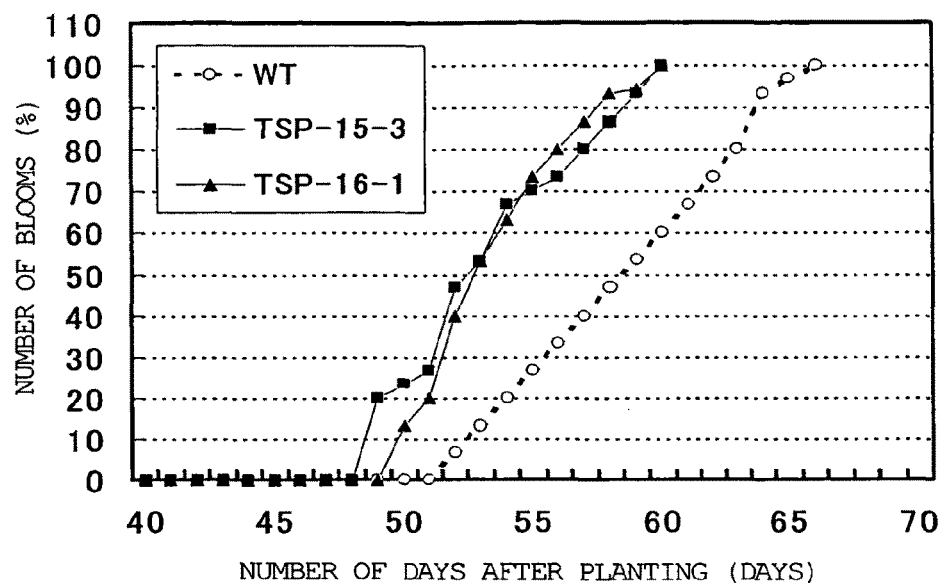
FIG. 7 is a diagram indicating a comparison of the day of blooming of a wild type plant and of a plant in which a polyamine metabolism-related enzyme gene has been introduced.

The results of FIG. 7 demonstrate that the days to blooming of the T3 transgenic plant is earlier than that of the wild type plant. It was confirmed that, on average, T3 transgenic plants are about 6 to 7 days earlier than the wild type plant.

TABLE 6

| | (Number of days after planting) | | |
|---|---|---|---|
| Line | Days to blooming | Days to pod maturation | Development period |
| Wild type plant (WT) | 59 | 78 | 19 |
| TSP-15-3 | 52 | 76 | 24 |
| TSP-16-1 | 53 | 76 | 23 |

The results of Table 6 demonstrate that the pod (ovary) development period of the T3 transgenic plants is significantly increased compared to that of the wild type plant.

Example 6

Evaluation of Transgenic Petunia (1) Production of Transgenic Petunia pBI101-35S-FSPD1+ and pBI101-35S-FSAM24+ were introduced into *Agrobacterium tumefacience* Ag10 strain (Lazo et al. BioTechnology 9:963-967 (1991)) by a method using calcium chloride (for example, Handbook of New Biochemistry Experiments 3, Kagaku Dojin page 121-122, 1996). The transformed *Agrobacterium* thus obtained was transmitted respectively onto leaf disks derived from the petunia (*Petunia hybrida*) variety Safinia Purple Mini (Suntory Flowers Co., Ltd.), and transgenic petunia were obtained by selecting plant cells indicating resistance to hygromycin, and by re-differentiation. The transformation of petunia was conducted using well-known methods (Horsch et al. Science 227: 1229-1231 (1985)). The various petunia transformed by pBI101-35S-FSPD1+ and pBI101-35S-FSAM24+ were taken to be Experiment PT144 and Experiment PT146. Twenty-three independent transgenic plants were obtained in PT144, and 43 plants in PT 146.

(2) Analysis of the Expression of Introduced Genes

The chromosomal DNA and RNA from these plants were prepared using the DNeasy Plant Mini Kit and RNeasy Plant Mini Kit (Qiagen Co., Ltd., Tokyo) respectively. It was found that PT144 and PT146 petunia are transgenic plants that retain SPDS (FSPD1) and SAMDC (FSAM24) genes respectively based on PCR reactions conducted using chromosomal DNA as a template (for PT144, the PCR reaction was conducted using primer FSPD1F (5'-TAGTAGAGGGATTAT-TATGTCTGCGGA-3'), designated as SEQ ID NO: 13, and FSPD1R (5'-ATGACGCTGATCACAATATAAAGCGAC-3'), designated as SEQ ID NO: 14; and for PT146, primer FSAM24F (5'-TGAAGGCTATGAAAAGAGGCT-TGAAGTA-3'), designated as SEQ ID NO: 15 and FSAM24R (5'-TCATGAGGATTGACCTTGGGATGACG-3'), designated as SEQ ID NO: 16). After maintaining at 95° C. for 1 minute, the reaction was conducted in 30 cycles of a cycle comprising 95° C. 1 minute, 52° C. 2 minutes, 72° C. 3 minutes, and then maintaining at 72° C. for 1 minute more.) Moreover, using whole RNAs extracted from these transgenic petunia leaves, the genetic expression of the various individuals were analyzed based on RT-PCR, wherein a reverse transcription reaction was conducted using a superscript fast strand synthesis system for RT-PCR (Invitrogen Co., Ltd., Tokyo) and using Oligo(dT) 12-18 primer, and wherein PCR was conducted by the same primers and cycles concerning chromosomal DNA using reverse transcription product as a template. The expression of foreign genes (SPDS in PT144; SAMDC in PT146) was confirmed in 9 individuals in PT144 plants, and 27 individuals in PT146 plants.

(3) Evaluation of Polyamine Content

The free polyamine content was analyzed in the individuals of the transgenic plants (cell lines) that had the most expression. Approximately 0.3 to 0.6 g of leaves from the transgenic plants (PT144, PT146) and the wild type plants (original strains: PT144-C, PT146-C), which were cultivated at the same time, were sampled, frozen and stored. Dilution internal standard solution (1,6-hexanediamine, internal standard content=7.5 nmol) and 5% perchloric acid aqueous solution (5 to 10 mL per 1.0 g specimen fresh weight) were added to the sampled specimen, and was thoroughly ground down and extracted using an omnimixer at room temperature. The ground solution was centrifuged at 4° C., 35,000×g for 20 minutes, and the supernatant was collected and was taken as the free polyamine solution. Four hundred microliters of free polyamine solution, 200 µL of saturated sodium carbonate aqueous solution, and 200 µL of dansyl chloride/acetone solution (10 mg/mL) were added into a microtube with a screw cap, and lightly mixed. After firmly closing with a tube stopper and covering with aluminum foil, dansylation was conducted by heating for 1 hour in a 60° C. water bath. After allowing the tube to cool, 200 µL of proline aqueous solution (100 mg/mL) was added and mixed. The tube was covered with aluminum foil and heated again for 30 minutes in a water bath. After standing to cool, the acetone was removed by spraying nitrogen gas, and then 600 µL of toluene was added and vigorously mixed. After allowing the tube to stand quietly and separate into 2 phases, toluene in the upper layer was separated into a 300-µL microtube. The toluene was completely removed by spraying nitrogen gas. 100 to 200 µL of methanol was added to the tube and the dansylated free polyamine was dissolved. The free polyamine content of putrescine, spermidine and spermine was assayed by the internal standard method using high performance liquid chromatography connected to a fluorescence detector. A µBondapak C18 (manufactured by Waters, Co.: 027324, 3.9×300 mm, particle size 10 µm) was used for the HPLC column. The polyamine content in the specimens was calculated by deriving the peak areas of the polyamine and internal standard from the HPLC charts of the standard solution and specimens. The results are indicated in Table 7. The mean value of free putrescine content in wild type plant (144-C, 146-C) was 29.46 nmol/gFW (FW: Fresh Weight), while the mean value in transgenic plant (144, 146) was 38.67 nmol/gFW. The mean value of free spermidine content in wild type plant was 37.03 nmol/gFW (FW: Fresh Weight), while the mean value in transgenic plant was 50.40 nmol/gFW. The amounts of free putrescine and free spermidine had both increased. The results of a t-test between the wild type plant and the transgenic plants using a 5% significance level revealed a difference in free spermidine, and demonstrated that the amount of spermidine in particular had increased in the transgenic plant. It was further confirmed that the free spermine content in the PT146 transgenic plant had increased significantly compared to the wild type plant (146-C).

TABLE 7

| Individual No. | Free putrescine (nmol/gFW) | Free spermidine (nmol/gFW) |
| --- | --- | --- |
| 144-C-1 | 24.44 | 46.2 |
| 144-C-2 | 15.05 | 31.38 |
| 144-6 | 30.12 | 65.7 |
| 144-7 | 46.92 | 55.54 |

TABLE 7-continued

| Individual No. | Free putrescine (nmol/gFW) | Free spermidine (nmol/gFW) |
| --- | --- | --- |
| 144-8 | 23.74 | 59.06 |
| 144-9 | 29.14 | 71.22 |
| 144-12 | 26.28 | 80.38 |
| 144-13 | 22.16 | 43.05 |
| 144-15 | 24.13 | 48.24 |
| 144-17 | 20.55 | 33.25 |
| 144-18 | 32.26 | 36.95 |
| 146-C-1 | 38.56 | 36.45 |
| 146-C-2 | 39.8 | 34.08 |
| 146-2 | 58.65 | 39.87 |
| 146-5 | 47.42 | 32.66 |
| 146-10 | 36.76 | 29.12 |
| 146-11 | 29.99 | 66.14 |
| 146-12 | 39.42 | 32 |
| 146-15 | 30.26 | 31.89 |
| 146-16 | 55.48 | 33.79 |
| 146-18 | 64.25 | 51.85 |
| 146-19 | 49.87 | 50.96 |
| 146-20 | 52.55 | 50.23 |
| 146-21 | 52.55 | 68.67 |
| 146-25 | 45.15 | 44.6 |
| 146-27 | 24.02 | 61.25 |
| 146-34 | 27.01 | 62.67 |
| 146-37 | 37.69 | 40.55 |
| 146-39 | 38.9 | 43.16 |
| 146-41 | 60.02 | 77.8 |

(4) Evaluation of Morphological Modification of Transgenic Petunia

Petunias were cultured in a closed system greenhouse with an air temperature of approximately 25° C. and artificial light supplementing natural light to make a 16-hour light, 8-hour dark cycle. The changes in the number of flowers per individual plant were measured over time from immediately after pruning to day 60 for individual plants that expressed foreign genes. The results are indicated in Table 8, FIGS. 8, and 9. The results of Table 8, FIGS. 8 and 9 clearly reveal that there were increased numbers of branches and flowers in the transgenic petunia compared to the original stock (wild type plant). During the measurement period, the number of flowers of the original stock Safinia Purple Mini did not exceed 10, but in 6 of the PT144 plants (67%) and in 18 of the PT146 plants (67%) the number of flowers exceeded 10. Moreover, in many of the plants of the original stock, the number of flowers per branch was 0 to 3, and hardly any branches with more than 5 flowers were observed. However, a high percentage of the transgenic plants had branches with more than 5 flowers, including 3 of the PT144 plants (33%) and 5 of the PT146 plants (19%).

TABLE 8

| Plant No. | Highest number of flowers on 1 branch | Number of branches | Number of flowers |
| --- | --- | --- | --- |
| 144-6 | 3 | 5 | 9 |
| 144-7 | 2 | 3 | 3 |
| 144-8 | 6 | 9 | 14 |
| 144-9 | 5 | 10 | 14 |
| 144-12 | 2 | 5 | 9 |
| 144-13 | 6 | 8 | 13 |
| 144-15 | 3 | 6 | 10 |
| 144-18 | 3 | 4 | 7 |
| 144-C1 | 2 | 1 | 2 |
| 144-C2 | 4 | 5 | 8 |
| 146-2 | 3 | 8 | 12 |
| 146-3 | 5 | 7 | 17 |
| 146-4 | 4 | 6 | 11 |
| 146-5 | 4 | 5 | 11 |
| 146-10 | 3 | 6 | 13 |

TABLE 8-continued

| Plant No. | Highest number of flowers on 1 branch | Number of branches | Number of flowers |
|---|---|---|---|
| 146-11 | 2 | 6 | 8 |
| 146-12 | 2 | 4 | 7 |
| 146-15 | 5 | 5 | 10 |
| 146-16 | 4 | 3 | 8 |
| 146-18 | 2 | 2 | 3 |
| 146-19 | 4 | 4 | 11 |
| 146-20 | 3 | 6 | 9 |
| 146-21 | 2 | 6 | 12 |
| 146-22 | 4 | 3 | 6 |
| 146-25 | 3 | 6 | 10 |
| 146-26 | 2 | 7 | 12 |
| 146-27 | 5 | 5 | 13 |
| 146-31 | 2 | 6 | 9 |
| 146-32 | 4 | 4 | 8 |
| 146-34 | 1 | 3 | 2 |
| 146-35 | 4 | 6 | 17 |
| 146-36 | 2 | 5 | 4 |
| 146-37 | 5 | 5 | 9 |
| 146-39 | 7 | 3 | 12 |
| 146-41 | 2 | 3 | 6 |
| 146-42 | 2 | 3 | 5 |
| 146-43 | 3 | 5 | 9 |
| 146-C1 | 1 | 1 | 1 |
| 146-C2 | 2 | 3 | 6 |

The correlation between the increase in the amount of polyamine and the increase in the number of flowers and the number of branches in petunia is found, and it has been demonstrated that introduced genes increase the amount of polyamine and bring about an increase in the number of flowers and the number of branches. In order to investigate whether the increase in the number of flowers observed here is caused by lengthening the blooming period of the individual flowers, or is caused by increasing the number of flower buds simultaneous blooming, the length of the blooming period was investigated in the individual plants that had the most flowers per branch (PT144 5 plants, PT146 9 plants), wherein the period from immediately after the flower blooms until the petals wither was taken as the blooming period; five flowers per individual plant were measured; and the mean values were compared. The mean number of blooming days of the original stock was 8.34 days, and mean number of blooming days of the transgenic plants was 9.35 days, and thus the blooming period tended to increase in the transgenic plants.

Example 7

Preparation and Analysis of Transgenic Sweet Potatoes (1) Preparation of Transgenic Sweet Potatoes Sweet potato Kokei No. 14 (donated by professor Takiko Shimada, Ishikawa Agricultural College, Agricultural Resource Institute, hereinafter referred to as "Kokei No. 14" or "wild type") was grown and cultivated in a pot under usual cultivation management to collect tens of cane tops (about 5 cm in length) containing shoot apex. The cane tops were immersed for two minutes in a 300-ml beaker to which 150 ml of 70% ethanol had been added, followed by dipped for 2 minutes in a beaker to which 150 ml of disinfecting solution (5% sodium hypochlorite, 0.02% Triton X-100) had been added. Sterilized cane tops were washed three times with a sterilized aqueous solution placed in a sterilization beaker. After washing, about 0.5 mm size of tissue containing meristematic tissue was aseptically removed under stereoscopic microscope. The tissue was then plated in embryogenic callus induction medium [4F1 plate: LS medium (1.9 g/l $KNO_3$, 1.65 g/l $NH_4NO_3$, 0.32 g/l $MgSO_4.7H_2O$, 0.44 g/l $CaCl_2.2H_2O$, 0.17 g/l $KH_2PO_4$, 22.3 mg/l $MnSO_4.4H_2O$, 8.6 mg/l $ZnSO_4.7H_2O$, 0.025 mg/l $CuSO_4.5H_2O$, 0.025 mg/l $CoCl_2.6H_2O$, 0.83 mg KI, 6.2 mg $H_3BO_3$, 27.8 mg $FeSO_4.7H_2O$, 37.3 mg/l $Na_2$.EDTA, 100 mg/l myo-inositol, 0.4 mg/l thiamine hydrochloride), 1 mg/L 4-fluorophenoxyacetic acid (4FA), 30 g/L sucrose, 3.2 g/l gellan gum, pH5.8] and then cultured in plant incubators (MLR-350HT, by Sanyo) under dark condition at 26° C. After about one month of culture, embryogenic calli capable of regeneration to plant body were selected from proliferated tissue. The selected embryogenic calli were continued to proliferate with transferred to a new 4F1 plate every month.

The transformed *Agrobacterium* strains EHA101/pBI35S-FSPD1+/−, EHA101/pBIC2-FSPD1+/−(wherein CaMV35S promoter was replaced by a promoter from horseradish peroxidase), EHA101/pBI35S-FSAM24+/− and EHA101/pBI35S-FADC76+/− were cultured for 2 nights at 27° C. on LB agar medium containing 50 mg/L kanamycin and 50 mg/L hygromycin to scrape *Agrobacterium* strains as much as about two grains of rice, which were suspended in 50 ml of infection medium (LS medium, 20 mg/l 3,5'-dimethoxy-4'-hydroxy-acetophenone, 1 mg/l 4FA, 30 g/l sucrose, pH5.8) and then shaken at 100 rpm for 1 hour at 26° C. under dark condition. The suspension was transferred to 300-ml sterilized beaker in which stainless steel basket was placed. The embryogenic calli which were cultured two to three weeks after transfer were placed on the basket of the beaker for dipping for two minutes. The calli together with the basket were placed on doubled sterilized filter paper to remove the excess moisture. The calli were transferred on co-culture medium (4F1A20 plate: LS medium, 1 mg/l 4FA, 20 mg/l 3,5'-dimethoxy-4'-hydroxy-acetophenone, 30 g/l sucrose, 3.2 g/l gellan gum, pH5.8) and co-cultured for three days at 22° C. under dark condition.

The embryogenic calli which were co-cultured for three days were transferred on the basket of the 300-ml beaker in which the sterilized stainless basket and 50 ml of disinfection solution containing carbenicillin in a final concentration of 500 mg/l in sterilized water was placed. The calli was fully washed for several minutes by anchoring the basket with tweezers. The embryogenic calli together with the basket were placed in the 300-ml beaker to which the disinfection solution was added for further washing. After repeating the same washing procedure, the excess moisture of the calli was removed on a sterilized filter paper to arrange and culture the calli in selection medium (4F1HmCar plate: LS medium, 1 mg/l 4FA, 25 mg/l hygromycin, 500 mg/l carbenicillin, 30 g/l sucrose, 3.2 g/l gellan gum, pH5.8) at 26° C. under dark condition.

Selection of the transformed calli which were cultured for two weeks was conducted by culturing the embryogenic calli with transfer to a new 4F1 HmCar plate every two weeks. Non-transformed calli turned brown, but part of transformants were embryogenic calli with pale yellow. After 60 days of culture on the selection medium, the transformed embryogenic calli were transferred to somatic cell embryogenic medium (A4G1HmCar plate: LS medium, 4 mg/l ABA, 1 mg/l GA3, 25 mg/l hygromycin, 500 mg/l carbenicillin, 30 g/l sucrose, 3.2 g/l gellan gum, pH5.8) to culture for two weeks at 26° C. under weak light and all long-day condition (30~40 μmol/m²/s) and then transferred to plant body forming medium (A0.05HmCar plate: LS medium, 0.05 mg/l ABA, 25 mg/l hygromycin, 500 mg/l carbenicillin, 30 g/l sucrose, 3.2 g/l gellan gum, pH5.8) to culture in the same condition. The transformants were transferred to a new A0.05HmCar plate every two weeks. Since the transformed cells turned green to form somatic cell embryo derived from embryogenic calli, somatic cell embryo was transferred to plant growth medium (0G plate: LS medium, 30 g/l sucrose, 3.2 g/l gellan gum, pH5.8) to form shoot.

The resulting transformants were subjected to confirmation and expression analysis of introduced gene. Specifically, confirmation of introduced gene was conducted by PCR and Southern hybridization after preparation of genome DNA. The expression analysis of introduced gene was conducted by Northern hybridization after preparation of RNA. It was confirmed that transgenic sweet potato in which target gene was introduced was obtained.

(2) Analysis of Polyamine

Cell lines were selected upon confirmation that the target gene had been introduced by PCR (or Southern analysis) and Northern analysis of the transformed sweet potatoes prepared in (1). Polyamine analysis was conducted with respect to cell lines in which polyamine metabolism-related enzyme gene was confirmed to be introduced and stably expressed. Cell lines TSP-SS-1, TSP-SS-2, TSP-SS-3, TSP-CS-1, TSP-CS-3 and TSP-CS-4 in which FSPD1 was introduced in sense direction (+) were selected. TSP-SS-1, TSP-SS-2 and TSP-SS-3 were cell lines in which a CaMV35S promoter was introduced. TSP-CS-1, TSP-CS-3 and TSP-CS-4 were cell lines in which a peroxidase promoter from horseradish (C2 promoter) was introduced. Cell lines TSP-SA-1 and TSP-SA-2 in which FSPD1 was introduced in antisense direction (−) were selected, which were cell lines in which a CaMV35S promoter was introduced. Cell lines TSP-SM-1, TSP-SM-2 and TSP-SM-5 in which FSAM24 was introduced in sense direction (+) were selected. TSP-SM-1, TSP-SM-2 and TSP-SM-5 were cell lines in which a CaMV35S promoter was introduced.

Approximately 0.3 to 0.9 g of young leaves from the transgenic plants (TSP) and the wild type plants (WT), which were cultivated at the same time, were sampled, frozen and stored. Dilution internal standard solution (1,6-hexanediamine, internal standard content=7.5 or 12 nmol) and 5% perchloric acid aqueous solution (5 to 10 mL per 1.0 g specimen fresh weight) were added to the sampled specimen, and was thoroughly ground down and extracted using an omnimixer at room temperature. The ground solution was centrifuged at 4° C., 35,000×g for 20 minutes, and the supernatant was collected and was taken as the free polyamine solution. Four hundred microliters of free polyamine solution, 200 μL of saturated sodium carbonate aqueous solution, and 200 μL of dansyl chloride/acetone solution (10 mg/mL) were added into a microtube with a screw cap, and lightly mixed. After firmly closing with the screw cap and covering with aluminum foil, dansylation was conducted by heating for 1 hour in a 60° C. water bath. After allowing the tube to cool, 200 μL of proline aqueous solution (100 mg/mL) was added and mixed. The tube was covered with aluminum foil and heated again for 30 minutes in a water bath. After standing to cool, the acetone was removed by spraying nitrogen gas, and then 600 μL of toluene was added and vigorously mixed. After allowing the tube to stand quietly and separate into 2 phases, toluene in the upper layer was separated into a 300-μL microtube. The toluene was completely removed by spraying nitrogen gas. 200 μL of methanol was added to the tube and the dansylated free polyamine was dissolved. The free polyamine contents of putrescine, spermidine and spermine were assayed by the internal standard method using high performance liquid chromatography connected to a fluorescence detector (exitation wavelength is 365 nm, emission wavelength is 510 nm). A μBondapak C18 (manufactured by Waters, Co.: 027324, 3.9× 300 mm, particle size 10 μm) was used for the HPLC column. The polyamine content in the specimens was calculated by deriving the peak areas of the polyamine and internal standard from the HPLC charts of the standard solution and specimens. The results are indicated in Table 8.

TABLE 8

| | Free polyamine content (nmolg$^{-1}$fw) | | | |
|---|---|---|---|---|
| Cell line | Putrescine | Spermidine | Spermine | Total polyamines |
| Wild type: WT | 38.98 ± 12.53 | 78.65 ± 11.83 | 43.98 ± 5.78 | 161.61 |
| TSP-SS-1 | 55.24 ± 5.71 | 148.91 ± 10.01 | 59.22 ± 3.57 | 263.37 |
| TSP-SS-2 | 49.98 ± 5.11 | 145.01 ± 12.17 | 65.19 ± 9.92 | 260.18 |
| TSP-SS-3 | 59.66 ± 3.98 | 140.94 ± 22.73 | 66.36 ± 6.48 | 266.96 |
| TSP-CS-1 | 57.66 ± 0.13 | 145.82 ± 3.62 | 74.24 ± 3.46 | 277.72 |
| TSP-CS-3 | 47.90 ± 4.86 | 122.78 ± 0.34 | 62.66 ± 5.71 | 233.34 |
| TSP-CS-4 | 52.73 ± 3.68 | 105.15 ± 1.30 | 54.79 ± 10.80 | 212.67 |
| TSP-SM-1 | 63.37 ± 7.75 | 106.64 ± 16.47 | 61.94 ± 7.11 | 231.95 |
| TSP-SM-2 | 48.28 ± 6.68 | 134.06 ± 15.03 | 75.32 ± 13.13 | 257.66 |
| TSP-SM-5 | 57.78 ± 3.72 | 139.99 ± 12.93 | 59.54 ± 2.90 | 257.31 |
| TSP-SA-1 | 69.89 ± 5.69 | 44.11 ± 8.47 | 38.37 ± 2.16 | 152.37 |
| TSP-SA-2 | 70.99 ± 3.10 | 40.31 ± 8.71 | 34.11 ± 2.03 | 145.41 |

Table 8 shows that cell lines in which the polyamine metabolism-related enzyme gene was introduced in sense direction had significantly higher levels of putrescine, spermidine and spermine contents than the wild type (WT), and that the total polyamine content was also significantly higher than in the wild type (WT). In particular, spermidine and spermine contents were increased remarkably. In addition, cell lines in which the polyamine metabolism-related enzyme gene was introduced in antisense direction had significantly lower levels of, in particular, spermidine and spermine contents than the wild type (WT), and that the total polyamine content was also significantly lower than in the wild type (WT), although putrescine content was increased.

The results showed that the introduction of the polyamine metabolism-related enzyme gene into sweet potato in sense or actisence direction allowed the polyamine content to be increased or decreased. The results showed that the introduction of the polyamine metabolism-related enzyme gene into sweet potato allowed the polyamine content to be controlled through the manipulation of polyamine metabolism.

Example 8

Evaluation of Morphological Modification of Transgenic Sweet Potatoes (1) Cultivation Test Under Normal Conditions Young seedlings of transformants (TSP) obtained in Example 7 and of a wild type (WT: Kokei No. 14) were fix-planted in a planter filled with commercial nursery soil (Sansan soil, by Takii & Co., Ltd.), and were cultivated for rooting for 7 days at 23° C. under long day conditions (16 hours light/8 hours darkness) and humid conditions. The plants were then acclimated and grown at 23° C. for about 1 month under soft-light/long day conditions and were transferred to a natural light-type growth chamber (Koitotron SBH-3030 from Koito Industries) where normal cultivation started under the following conditions: temperature (day/night: 26° C./24° C.), humidity (50 to 60%), and light (natural day length). The vines (stems) and leaves were examined after 1 month of normal cultivation. The results are shown in FIG. 10. FIG. 10 demonstrates that the transformant (TSP) had longer stems (vines) and more leaves than the wild type (WT). Upon closer examination of the vines, the transformant (TSP) turned out to have less space between knots than the wild type (WT), while the 17 petioles (leaves) of the transformant (TSP) showed a marked increase compared to the 5 petioles (leaves) of the wild type (WT). After three months of normal culture the tuberous roots (potatoes) were also examined. The results are given in FIGS. 11A and 11B. When comparing the number of tuberous roots per stock between the transformant and the wild type, the transformant had a greater number of tuberous roots (potatoes) than the wild type. Upon examination of the yields of tuberous root, the transformant showed a dramatic increase in yield, with fresh weights of 325.99 g and 200.18 g of sweet potatoes per plant against 79.08 g and 101.36 g of the wild type (WT).

(2) Cultivation Test Under Moderately Stressful Conditions

Lines (TSP-SS-1, TSP-SS-2, TSP-SS-4) were selected from transformed independent line. Stems (15-20 per one line) were cut from the shoots of three transformed lines (TSP-SS-1, TSP-SS-2, TSP-SS-4) and of the wild type (WT: Kokei No. 14), were planted in a plastic pod filled with commercial nursery soil (Sansan soil, by Takii & Co., Ltd.), and were cultivated for rooting. After rooting, the plants were uniformly cultivated for about 1 month in close-type glass house (temperature: 22 to 25° C., humidity: 55%, natural day length) until full development of fifth leaf. After three months of cultivation under moderately stressful conditions of light intensity (40 $\mu molm^{-2}s^{-1}$ PPFD; 16 hours day length) and temperature of 21 to 22° C., the formation of tuberous roots (sweet potatoes) was examined. Examined tuberous roots are shown in FIG. 12 (regarding transformant, rootlets were removed for better viewing of tuberous roots). Tuberous roots were not formed in the wild type plant. In contrast, tuberous roots were formed in the three transgenic plants with a tuberous root formation rate of 33%, 80% and 89%, respectively. In reproducibility test cultivated for six months under the same moderately stressful environment as above, similar results were obtained with a tuberous root formation rate of 50 to 83% depending on the transformant lines.

(3) Cultivation Test Under Various Stress Conditions

Two transformed independent lines (TSP-SS-1 and TSP-SS-4) were selected from the transformed independent line. Two transformant and the wild type (WT: Kokei No. 14) were subjected to a cultivation test in a close-type glass house. Stems with one bud cut from the shoots of two transformed lines and the wild type plant were planted in a planter filled with commercial nursery soil (Sansan soil, by Takii & Co., Ltd.), and were cultivated for rooting. After rooting, the plants were cultivated in close-type glass house (temperature: 23° C./21° C., humidity: 55%, natural day length) until full development of fifth leaf. After three weeks of cultivation, seedling with the same stage of growth and development were selected. Four seedlings were fix-planted in a 30-L planter filled with 20 L of commercial nursery soil (Sansan soil, by Takii & Co., Ltd.) in such a manner that six planter were used per one independent line (2 planters per one treatment) and were cultivated in close-type glass house (temperature: 23 to 24° C./21 to 22° C., humidity: 55%, natural day length). Potassium sulfate (3.6 g) and ECOLONG (14-12-14, 100 day-type; 13.4 g) were fertilized to a planter as fertilizer. Soil water was determined by tensiometer (DM-8M, SANSY-OUSYA) installed in all the planters. Stress treatments including non-stress (control) salt stress and drought stress were conducted using two planters per one stress treatment. Salt stress treatment was conducted by mixing 80 g of NaCl per 100 L of commercial nursery soil throughout the composite when planting, followed by adding 40 g of NaCl per 100 L of commercial nursery soil 1.5 months after the planting. NaCl level was 21 mmol/L per planter. Salt stress was applied from the beginning of planting. Tap water (1.5 to 6 L/time/planter) was distributed in control and salt stress until pF was decreased to field moisture capacity (pF 1.5) with taking pF 2.3 as an affusion point. Drought stress was applied by limitation of water distribution. Tap water (0.75 to 3 L) was distributed when pF was 2.9. Drought stress treatment was started after one week of planting in view of rooting. The fresh weight and number of tuberous roots were examined after four months from planting (harvesting stage). With respect to polyamine analysis, free polyamine contents in leaves and tuberous roots were examined. FIG. 13 shows growth (fresh weight) of roots (tuberous roots), four months after the planting. Regarding control, the fresh weight of tuberous roots was significantly heavier in transgenic plant than in wild type plant. The fresh weight of tuberous roots per stock was 40 g heavier in transgenic plant than in wild type plant. The fresh weight of tuberous roots in salt stress was significantly heavier in transgenic plant than in wild type plant. The fresh weight of tuberous roots per stock was 60 g heavier in transgenic plant than in wild type plant. The fresh weight of tuberous roots in drought stress was significantly heavier in transgenic plant than in wild type plant. The fresh weight of tuberous roots per stock was 30 g heavier in transgenic plant than in wild type plant. The results of the number of tuberous roots are shown in table 9. The transgenic plants had additional two pieces of tuberous roots compared to wild type plant per plant of stress treatment. It was confirmed that the transgenic plants were increased in yield and the number of tuberous roots compared to the wild type plant. Polyamine contents in leaves and tuberous root were analyzed after two months from planting and also harvesting stage. The results at harvesting stage were shown in FIG. 14. The transgenic plants had two times higher spermidine (Spd) level than wild type plant independent of stress treatment. In some treatments, putrescine (Put) and spermine (Spm) levels were also increased in transgenic plant. In view of the results as indicated above, it was demonstrated that increase of polyamine level in sweet potatoes resulted in improved morphological modification of tuberous roots (roots) and also increase of yield and number of tuberous roots. Next, content of starch (major component in tuberous roots) was examined. Tuberous roots with uniform size were selected from each stock and 100 to 200 g of tuberous root samples were cut from a central region of the tuberous roots. The tuberous root samples were chopped and grinded for 1.5 minutes with a blender mixer by adding 500 ml of distilled water. The grinded solution was filtered with a 75 μm filter, and the filtrate was collected. The filter was washed with 500 ml of distilled water and the washings and the filtrate were combined and allowed to stand for several hours to precipitate starch. The supernatant was decanted and 500 ml of distilled water was added to the precipitate to wash the starch and then allowed to stand for precipitation of starch. The supernatant was then decanted. To the precipitate was added 500 ml of distilled water and the mixture was stirred and allowed to stand for precipitation of starch. The supernatant was then decanted. After repeating the process at least three times to fully wash starch. The washed and precipitated starch was subjected to airflow dry ing for at least 2 days at room temperature. The dried starch was recovered and weighed to calculate starch content (%) per fresh weight. The starch content per fresh weight of tuberous root was higher in transgenic plants than wild type plant in all treatment. In particular, in drought stress treatment, starch content of wild type plant was 12%, while two lines of transgenic plants (TSP-SS-1, TSP-SS-4) were as high as 17%. As shown above, it was demonstrated that the content of starch which was a major component of tuberous root was increased by elevating polyamine levels in plant.

TABLE 9

The number of tuberous root of sweet potatoes cultivated under stress environment per one stock

|  | Non-stress | NaCl | Drought |
|---|---|---|---|
| WT | 3.28 ± 0.28 | 4.00 ± 0.57 | 2.71 ± 0.35 |
| TSP-SS-1 | 5.00 ± 0.43 | 6.12 ± 0.61 | 4.50 ± 0.32 |
| TSP-SS-4 | 5.00 ± 0.43 | 5.28 ± 0.68 | 4.00 ± 0.43 |

The invention claimed is:

1. A method for producing plants with improved morphogenesis, which method comprises the steps of:
(1) transforming cells of a plant with at least one expression vector containing a plant spermidine synthase (SPDS) gene under the control of one or more promoters capable of functioning in plants,
(2) regenerating plant bodies from the transformed cells,
(3) cultivating the plant bodies under normal conditions,
(4) evaluating the cultivated plants for improved morphogenesis and increased spermidine content compared to the plant prior to transformation with the plant SPDS gene, and
(5) selecting cultivated plants having improved morphogenesis as compared to the plant prior to transformation with the plant SPDS gene, wherein the improved morphogenesis is one or more traits selected from the group consisting of:
(i) increased number of seeds, grains or ovules,
(ii) increased number of flowers,
(iii) increased number of ovaries, fruit, cotton balls, pods, ears, or capsules,
(iv) increased number of stems, main stems, side stems, flower stalks, trunks, or branches,
(v) increased number of leaves,
(vi) extended flower blooming period,
(vii) increased development period from bearing to maturity of ovaries, fruit, pods, or capsules, and
(viii) increased number of roots or tuberous roots.

2. The method of claim 1, wherein the plant bodies are cultivated under normal conditions for at least 7 weeks.

3. The method of claim 1, wherein the improved morphogenesis is improved in the reproductive stage more than in the vegetative stage.

4. A method for producing a plant that is a homozygote with respect to a plant spermidine synthase (SPDS) gene and which has improved morphogenesis, which method comprises the steps of:
(1) transforming a plant with at least one expression vector containing the SPDS gene under the control of one or more promoters capable of functioning in plants,
(2) regenerating plants with increased spermidine content and improved morphogenesis compared to the plant prior to transformation with the plant SPDS gene,
(3) harvesting seeds from the regenerated plants, and
(4) analyzing the SPDS gene in the seeds by cultivating the seeds to provide plants and selecting a plant that is homozygous with respect to the SPDS gene, wherein the improved morphogenesis is one or more traits selected from the group consisting of:
(i) increased number of seeds, grains or ovules,
(ii) increased number of flowers,
(iii) increased number of ovaries, fruit, cotton balls, pods, ears, or capsules,
(iv) increased number of stems, main stems, side stems, flower stalks, trunks, or branches,
(v) increased number of leaves,
(vi) extended flower blooming period,
(vii) increased development period from bearing to maturity of ovaries, fruit, pods, or capsules, and
(viii) increased number of roots or tuberous roots.

5. A method for producing plants with improved morphogenesis, which method comprises the steps of:
(1) transforming cells of a plant with at least one expression vector containing a plant spermidine synthase (SPDS) gene under the control of one or more promoters capable of functioning in plants,
(2) regenerating plant bodies from the transformed cells,
(3) cultivating the plant bodies under normal conditions until at least one increased morphogenetic trait and increased spermidine content compared to the plant prior to transformation with the plant SPDS gene are exhibited, and
(4) selecting cultivated plants having improved morphogenesis, wherein the improved morphogenesis is one or more traits selected from the group consisting of:
(i) increased number of seeds, grains or ovules,
(ii) increased number of flowers,
(iii) increased number of ovaries, fruit, cotton balls, pods, ears, or capsules,
(iv) increased number of stems, main stems, side stems, flower stalks, trunks, or branches,
(v) increased number of leaves,
(vi) extended flower blooming period,
(vii) increased development period from bearing to maturity of ovaries, fruit, pods, or capsules, and
(viii) increased number of roots or tuberous roots.

* * * * *

SEQUENCE LISTING

<160> NUMBER OF SEQ ID NOS: 16

<210> SEQ ID NO 1
<211> LENGTH: 1328
<212> TYPE: DNA
<213> ORGANISM: Cucurbita ficifolia
<220> FEATURE:
<221> NAME/KEY: CDS
<222> LOCATION: (77)..(1060)

<400> SEQUENCE: 1

```
ccaacgggtc atacagaagc actccccact gtattgggat ttgggattttt agcgagtcga      60 tagtagaggg attatt atg tct gcg gaa cat atc gtt ggg tcg gcg gcc gat     112
               Met Ser Ala Glu His Ile Val Gly Ser Ala Ala Asp
                 1               5                  10 gcg gcg gcg aag aaa cct gag att gag aat ggg gta tcc gcc tca cag      160
Ala Ala Ala Lys Lys Pro Glu Ile Glu Asn Gly Val Ser Ala Ser Gln
             15                  20                  25 ccc gat tct att tcc tct gta att cct gga tgg ttt tct gaa att agc      208
Pro Asp Ser Ile Ser Ser Val Ile Pro Gly Trp Phe Ser Glu Ile Ser
     30                  35                  40 cca atg tgg cct gga gag gcc cat tcc ttg aag gtg gag aag gtt ttg      256
Pro Met Trp Pro Gly Glu Ala His Ser Leu Lys Val Glu Lys Val Leu
 45                  50                  55                  60 ttt caa ggg aag tct gat tac cag aac gtt ttg gta ttt cag tca tca      304
Phe Gln Gly Lys Ser Asp Tyr Gln Asn Val Leu Val Phe Gln Ser Ser
                 65                  70                  75 act tat ggg aag gtt ctg gtt ttg gat ggc gtg att cag ctt aca gag      352
Thr Tyr Gly Lys Val Leu Val Leu Asp Gly Val Ile Gln Leu Thr Glu
             80                  85                  90 aga gat gaa tgt gct tac caa gag atg atc acc cac ctt cca ctt tgc      400
Arg Asp Glu Cys Ala Tyr Gln Glu Met Ile Thr His Leu Pro Leu Cys
         95                  100                 105 tca att cca aac ccc aaa aag gtt ctc gtt atc ggt gga gga gac ggc      448
Ser Ile Pro Asn Pro Lys Lys Val Leu Val Ile Gly Gly Gly Asp Gly
    110                 115                 120 ggt gtt ttg cga gag gtg gct cgc cat tca tct gtt gag cag ata gat      496
Gly Val Leu Arg Glu Val Ala Arg His Ser Ser Val Glu Gln Ile Asp
125                 130                 135                 140 atc tgt gaa atc gac aag atg gta gtt gat gtt tcc aaa gaa ttt ttc      544
Ile Cys Glu Ile Asp Lys Met Val Val Asp Val Ser Lys Glu Phe Phe
                145                 150                 155 cct cgc gta gct gtc ggg ttt gag gat cct cgt gtc act ctt cat att      592
Pro Arg Val Ala Val Gly Phe Glu Asp Pro Arg Val Thr Leu His Ile
            160                 165                 170 ggt gat ggc gtc gca ttt ctg aag gct gtt cct gaa ggc act tat gat      640
Gly Asp Gly Val Ala Phe Leu Lys Ala Val Pro Glu Gly Thr Tyr Asp
        175                 180                 185 gca gtg ata gtg gat tct tct gat cct att ggt cct gca caa gag ctc      688
```

```
Ala Val Ile Val Asp Ser Ser Asp Pro Ile Gly Pro Ala Gln Glu Leu
    190             195             200 ttt gag aag cct ttt ttt gct tca gtt gcc aaa gct ctt cga cca gga         736
Phe Glu Lys Pro Phe Phe Ala Ser Val Ala Lys Ala Leu Arg Pro Gly
205             210             215             220 ggc gtt gtg tgt act caa gca gag agc att tgg ctt cac atg cat atc         784
Gly Val Val Cys Thr Gln Ala Glu Ser Ile Trp Leu His Met His Ile
                225             230             235 att gaa gac att gta aca aac tgc cgc caa ata ttc aaa ggc tct gtc         832
Ile Glu Asp Ile Val Thr Asn Cys Arg Gln Ile Phe Lys Gly Ser Val
            240             245             250 aac tat gca tgg act aca gtt cct aca tat cca agc gga gtg att ggg         880
Asn Tyr Ala Trp Thr Thr Val Pro Thr Tyr Pro Ser Gly Val Ile Gly
                255             260             265 ttt atg ctc tgc tca act gag ggg cct cct ctt gat ttc aag cat cca         928
Phe Met Leu Cys Ser Thr Glu Gly Pro Pro Leu Asp Phe Lys His Pro
270             275             280 gtc aac cca gta gag gtg aac ggt atc gac acc gtg aag agt ccg ctc         976
Val Asn Pro Val Glu Val Asn Gly Ile Asp Thr Val Lys Ser Pro Leu
285             290             295             300 aag ttt tac aac tcg gag att cat aca gca gct ttc tgt ttg cct tct        1024
Lys Phe Tyr Asn Ser Glu Ile His Thr Ala Ala Phe Cys Leu Pro Ser
                305             310             315 ttt gcg aag aag atc atc gat tca aaa gca aaa tga aaaggtttcc             1070
Phe Ala Lys Lys Ile Ile Asp Ser Lys Ala Lys
                320             325 cccacagcgt tgaagaagca gaaattggcg tcttggagt gtgccaatgt aataagtgga       1130
ggcttaaatt agagtcgaaa tggtcgcttt atattgtgat cagcgtcata agtttcttg       1190 agatgttatg agtagtagaa atagcttttg ttttcctccc caaaattttc cccgtccttt      1250
ttcattgaaa agtgacatct ggtgttctag cttctataaa taaatatgct aaataaatat      1310
atttagccaa aaaaaaaa                                                    1328

<210> SEQ ID NO 2
<211> LENGTH: 327
<212> TYPE: PRT
<213> ORGANISM: Cucurbita ficifolia

<400> SEQUENCE: 2

Met Ser Ala Glu His Ile Val Gly Ser Ala Ala Asp Ala Ala Ala Lys
1               5                   10                  15

Lys Pro Glu Ile Glu Asn Gly Val Ser Ala Ser Gln Pro Asp Ser Ile
            20                  25                  30

Ser Ser Val Ile Pro Gly Trp Phe Ser Glu Ile Ser Pro Met Trp Pro
        35                  40                  45

Gly Glu Ala His Ser Leu Lys Val Glu Lys Val Leu Phe Gln Gly Lys
    50                  55                  60

Ser Asp Tyr Gln Asn Val Leu Val Phe Gln Ser Ser Thr Tyr Gly Lys
65                  70                  75                  80

Val Leu Val Leu Asp Gly Val Ile Gln Leu Thr Glu Arg Asp Glu Cys
                85                  90                  95

Ala Tyr Gln Glu Met Ile Thr His Leu Pro Leu Cys Ser Ile Pro Asn
            100                 105                 110

Pro Lys Lys Val Leu Val Ile Gly Gly Asp Gly Val Leu Arg
        115                 120                 125

Glu Val Ala Arg His Ser Ser Val Glu Gln Ile Asp Ile Cys Glu Ile
    130                 135                 140
```

```
Asp Lys Met Val Val Asp Val Ser Lys Glu Phe Phe Pro Arg Val Ala
145                 150                 155                 160

Val Gly Phe Glu Asp Pro Arg Val Thr Leu His Ile Gly Asp Gly Val
            165                 170                 175

Ala Phe Leu Lys Ala Val Pro Glu Gly Thr Tyr Asp Ala Val Ile Val
        180                 185                 190

Asp Ser Ser Asp Pro Ile Gly Pro Ala Gln Glu Leu Phe Glu Lys Pro
    195                 200                 205

Phe Phe Ala Ser Val Ala Lys Ala Leu Arg Pro Gly Gly Val Val Cys
210                 215                 220

Thr Gln Ala Glu Ser Ile Trp Leu His Met His Ile Ile Glu Asp Ile
225                 230                 235                 240

Val Thr Asn Cys Arg Gln Ile Phe Lys Gly Ser Val Asn Tyr Ala Trp
            245                 250                 255

Thr Thr Val Pro Thr Tyr Pro Ser Gly Val Ile Gly Phe Met Leu Cys
        260                 265                 270

Ser Thr Glu Gly Pro Pro Leu Asp Phe Lys His Pro Val Asn Pro Val
    275                 280                 285

Glu Val Asn Gly Ile Asp Thr Val Lys Ser Pro Leu Lys Phe Tyr Asn
290                 295                 300

Ser Glu Ile His Thr Ala Ala Phe Cys Leu Pro Ser Phe Ala Lys Lys
305                 310                 315                 320

Ile Ile Asp Ser Lys Ala Lys
                325

<210> SEQ ID NO 3
<211> LENGTH: 1814
<212> TYPE: DNA
<213> ORGANISM: Cucurbita ficifolia
<220> FEATURE:
<221> NAME/KEY: CDS
<222> LOCATION: (456)..(1547)

<400> SEQUENCE: 3
tccgtctgcg gcctcttgaa ttctcatcgt ttctctctct ttcgaatttt gttttctttc      60
gctctcagcc cttcttgca agttttattt taggcattct ccgggtttcc ttctcctccg     120
ctaattcttt tcatcgcgaa tgatttaatg gagtcaaaag gtggtaagaa gtctagtagt     180
agtagtagta gaagcagtaa atccctttc tacgaagctc ccctcggata cagcattgaa     240
gacgttagac cacacggtgg aatcaagaag ttcagatctg ctgcctactc caactgcgtt     300
cgtaaaccat cctgagttct gctgaattcc gtttttcctg cgcaccgaga tccttagttt     360
tctataattt ttactgtgtc tttttttcttt agtactctac tttcctcgtt ctctcgttca     420
atctctcaac attagtaact tccttttaag aaaag atg acg ttt cct acc tct        473
                                    Met Thr Phe Pro Thr Ser
                                      1               5 gca atc gga ttt gaa ggc tat gaa aag agg ctt gaa gta tca ttc ttt        521
Ala Ile Gly Phe Glu Gly Tyr Glu Lys Arg Leu Glu Val Ser Phe Phe
              10                  15                  20 gag ccc ggc att ttt gct gac cca agg ggc atg ggc ctt cgt gct ttg        569
Glu Pro Gly Ile Phe Ala Asp Pro Arg Gly Met Gly Leu Arg Ala Leu
         25                  30                  35 tcc aag gca caa cta gat gaa att ctg aca tta gcc gag tgc acc att        617
Ser Lys Ala Gln Leu Asp Glu Ile Leu Thr Leu Ala Glu Cys Thr Ile
     40                  45                  50 gtt gat tct ttg tcc aat gac tat ctt gat tca tat gtc ctt tcg gag        665
Val Asp Ser Leu Ser Asn Asp Tyr Leu Asp Ser Tyr Val Leu Ser Glu
 55                  60                  65                  70
```

```
tcg agc ctc ttt gtc tac cca tac aag ttc atc atc aaa act tgc ggc      713
Ser Ser Leu Phe Val Tyr Pro Tyr Lys Phe Ile Ile Lys Thr Cys Gly
                 75                  80                  85 act act aag ctg ctt ctg tct att cca gct ctg ata aag ttg gct gat      761
Thr Thr Lys Leu Leu Leu Ser Ile Pro Ala Leu Ile Lys Leu Ala Asp
             90                  95                 100 tct cta tcc ctt aat gtg aaa tct gtg agg tac act cgt gga agc ttt      809
Ser Leu Ser Leu Asn Val Lys Ser Val Arg Tyr Thr Arg Gly Ser Phe
            105                 110                 115 atc ttt cct ggt gcc cag tct ttt ccc cat cgc agc ttc tct gag gaa      857
Ile Phe Pro Gly Ala Gln Ser Phe Pro His Arg Ser Phe Ser Glu Glu
        120                 125                 130 gtt gct gtt ctt gat ggc tac ttg gcc aag ctt ggc ctc cat ggc tct      905
Val Ala Val Leu Asp Gly Tyr Leu Ala Lys Leu Gly Leu His Gly Ser
135                 140                 145                 150 gct tat gtg atg gga agt cct gat gag aca agg aaa tgg cac gtt tac      953
Ala Tyr Val Met Gly Ser Pro Asp Glu Thr Arg Lys Trp His Val Tyr
                155                 160                 165 tct gcc tgt gcc aaa atg ggt agc cga agc tac aat ccc gtc tat act     1001
Ser Ala Cys Ala Lys Met Gly Ser Arg Ser Tyr Asn Pro Val Tyr Thr
            170                 175                 180 ctg gag atg tgc atg act ggc tta gac aag gag aag gcg tct gtc ttc     1049
Leu Glu Met Cys Met Thr Gly Leu Asp Lys Glu Lys Ala Ser Val Phe
        185                 190                 195 ttc aaa aca gac aca agt tct gct gct gca atg act gaa aac tcc ggt     1097
Phe Lys Thr Asp Thr Ser Ser Ala Ala Ala Met Thr Glu Asn Ser Gly
    200                 205                 210 atc agg aag atc ctt ccg aaa tct gat ata tgc gac ttt gag ttt gac     1145
Ile Arg Lys Ile Leu Pro Lys Ser Asp Ile Cys Asp Phe Glu Phe Asp
215                 220                 225                 230 cca tgt ggg tat tcc atg aat gct att gaa gga gat gcg gag tct acc     1193
Pro Cys Gly Tyr Ser Met Asn Ala Ile Glu Gly Asp Ala Glu Ser Thr
                235                 240                 245 atc cat gtc act cca gaa gaa ggg ttt agc tat gca agc ttt gaa gca     1241
Ile His Val Thr Pro Glu Glu Gly Phe Ser Tyr Ala Ser Phe Glu Ala
            250                 255                 260 gct ggt tat gaa ttg gac gac ctg gac ctg tgt aag gtg att ggg agg     1289
Ala Gly Tyr Glu Leu Asp Asp Leu Asp Leu Cys Lys Val Ile Gly Arg
        265                 270                 275 gtg ctg gca tgc ttc cag cca tct gat ttc tct gtt gcc ctc cac tca     1337
Val Leu Ala Cys Phe Gln Pro Ser Asp Phe Ser Val Ala Leu His Ser
    280                 285                 290 gat gtg gtc ggt gag gat ctg aaa gat tta ctg tgc ctg gac ctg aag     1385
Asp Val Val Gly Glu Asp Leu Lys Asp Leu Leu Cys Leu Asp Leu Lys
295                 300                 305                 310 ggg tac gag ggt gga gag aag agc tgt gaa atg ctt ggg gaa aat gga     1433
Gly Tyr Glu Gly Gly Glu Lys Ser Cys Glu Met Leu Gly Glu Asn Gly
                315                 320                 325 tcc gtc atc tat cag agc ttt aag aat aga gga gat tat gcg tca tct     1481
Ser Val Ile Tyr Gln Ser Phe Lys Asn Arg Gly Asp Tyr Ala Ser Ser
            330                 335                 340 cca agg tca atc ctc atg aaa tgc tgt tgg aga gag gac gag gcg gac     1529
Pro Arg Ser Ile Leu Met Lys Cys Cys Trp Arg Glu Asp Glu Ala Asp
        345                 350                 355 gag gaa gtt gag aag tag tagtagttac ttactttcaa cttttgctgc            1577
Glu Glu Val Glu Lys
360 gttttatctt ttaatactat agtatcttcg gggtcgttct gttctgtgct gttctgttct   1637 ttcattatgt cctttgtgt tgtttccttt gcgaataata attcccaggt ggggatggta    1697
```

-continued

```
ggctgtcgtg tcctgtcctg gagagtctat cgtctgatgt tattatgatc atcaaactat    1757
ataatgataa tatcgtattt ccttatttaa aaaaaaaaaa aaaaaaaaaa aaaaaaa       1814
```

<210> SEQ ID NO 4
<211> LENGTH: 363
<212> TYPE: PRT
<213> ORGANISM: Cucurbita ficifolia

<400> SEQUENCE: 4

```
Met Thr Phe Pro Thr Ser Ala Ile Gly Phe Glu Gly Tyr Glu Lys Arg
1               5                   10                  15

Leu Glu Val Ser Phe Phe Glu Pro Gly Ile Phe Ala Asp Pro Arg Gly
            20                  25                  30

Met Gly Leu Arg Ala Leu Ser Lys Ala Gln Leu Asp Glu Ile Leu Thr
        35                  40                  45

Leu Ala Glu Cys Thr Ile Val Asp Ser Leu Ser Asn Asp Tyr Leu Asp
    50                  55                  60

Ser Tyr Val Leu Ser Glu Ser Ser Leu Phe Val Tyr Pro Tyr Lys Phe
65                  70                  75                  80

Ile Ile Lys Thr Cys Gly Thr Thr Lys Leu Leu Ser Ile Pro Ala
                85                  90                  95

Leu Ile Lys Leu Ala Asp Ser Leu Ser Leu Asn Val Lys Ser Val Arg
            100                 105                 110

Tyr Thr Arg Gly Ser Phe Ile Phe Pro Gly Ala Gln Ser Phe Pro His
        115                 120                 125

Arg Ser Phe Ser Glu Glu Val Ala Val Leu Asp Gly Tyr Leu Ala Lys
    130                 135                 140

Leu Gly Leu His Gly Ser Ala Tyr Val Met Gly Ser Pro Asp Glu Thr
145                 150                 155                 160

Arg Lys Trp His Val Tyr Ser Ala Cys Ala Lys Met Gly Ser Arg Ser
                165                 170                 175

Tyr Asn Pro Val Tyr Thr Leu Glu Met Cys Met Thr Gly Leu Asp Lys
            180                 185                 190

Glu Lys Ala Ser Val Phe Phe Lys Thr Asp Thr Ser Ala Ala Ala
        195                 200                 205

Met Thr Glu Asn Ser Gly Ile Arg Lys Ile Leu Pro Lys Ser Asp Ile
    210                 215                 220

Cys Asp Phe Glu Phe Asp Pro Cys Gly Tyr Ser Met Asn Ala Ile Glu
225                 230                 235                 240

Gly Asp Ala Glu Ser Thr Ile His Val Thr Pro Glu Glu Gly Phe Ser
                245                 250                 255

Tyr Ala Ser Phe Glu Ala Ala Gly Tyr Glu Leu Asp Asp Leu Asp Leu
            260                 265                 270

Cys Lys Val Ile Gly Arg Val Leu Ala Cys Phe Gln Pro Ser Asp Phe
        275                 280                 285

Ser Val Ala Leu His Ser Asp Val Val Gly Asp Leu Lys Asp Leu
    290                 295                 300

Leu Cys Leu Asp Leu Lys Gly Tyr Glu Gly Glu Lys Ser Cys Glu
305                 310                 315                 320

Met Leu Gly Glu Asn Gly Ser Val Ile Tyr Gln Ser Phe Lys Asn Arg
                325                 330                 335

Gly Asp Tyr Ala Ser Ser Pro Arg Ser Ile Leu Met Lys Cys Cys Trp
            340                 345                 350

Arg Glu Asp Glu Ala Asp Glu Glu Val Glu Lys
```

<210> SEQ ID NO 5
<211> LENGTH: 3037
<212> TYPE: DNA
<213> ORGANISM: Cucurbita ficifolia
<220> FEATURE:
<221> NAME/KEY: CDS
<222> LOCATION: (541)..(2661)

<400> SEQUENCE: 5

```
gtttattaaa cgcattctat tgtctctccg agggctctcc aattcttccc gttaggtttc      60
cgtttgttcc tcttttctc cgccttttc ccggaaaatc tgtttgttga agcaattgca      120
tcctcttttg ttttgttttt cttcttttgt tgaatccctg gtttgaattt ttgtgtggat      180
tctttgattt ccagatctgc atggtgaaga gcggtttcgg tgtttgatgt ttgattggtt      240
ttgaattcgt agcttgattt ttgtgtttgt tgttatcaaa ttcttcttct gagcggatcg      300
cggtgggata ttggaagtgt ataggggagc gcggtggatt tgacggtgga aatagctact      360 tttttgctt cttttgaggg ggtagccggg gcctcggcct cggcgggttt taaagccccc      420
acttggacga actctggatt taccattcct ttctcttaac aatttctcta actaatcttt      480
tcgtttttta aattttccgt ctccattttc ttattctttt cttgatccgt cgtcggagag      540
```

```
atg ccg gcc cta gct tat tgc gtg gaa gct gct gca gct cct cct cct       588
Met Pro Ala Leu Ala Tyr Cys Val Glu Ala Ala Ala Ala Pro Pro Pro
1               5                   10                  15 ggc tgc gct ttt gct ggg gat agc tct ctt ccg tcg ccg gtc tta ttt       636
Gly Cys Ala Phe Ala Gly Asp Ser Ser Leu Pro Ser Pro Val Leu Phe
            20                  25                  30 tcc ggc gga cct ccg gag act acc atc ttc acc tct ccc gct gct gct       684
Ser Gly Gly Pro Pro Glu Thr Thr Ile Phe Thr Ser Pro Ala Ala Ala
        35                  40                  45 ccc att tct gaa aat ccc tct tgg tct cct tct ctg tct tcc tcc ctt       732
Pro Ile Ser Glu Asn Pro Ser Trp Ser Pro Ser Leu Ser Ser Ser Leu
    50                  55                  60 tac aag ata gat gga tgg ggt gcc cct tat ttc tct gtc aat ggc tct       780
Tyr Lys Ile Asp Gly Trp Gly Ala Pro Tyr Phe Ser Val Asn Gly Ser
65                  70                  75                  80 ggg aat atg gcc gtt cgg cct tac ggt aca gcc acc ttg ccc cat cag       828
Gly Asn Met Ala Val Arg Pro Tyr Gly Thr Ala Thr Leu Pro His Gln
                85                  90                  95 gag att gat ctc ttg aaa att gtg aag aag gct tca gat ccg att agc       876
Glu Ile Asp Leu Leu Lys Ile Val Lys Lys Ala Ser Asp Pro Ile Ser
            100                 105                 110 tct ggt ggg ctt ggc ttg cag ctt cct ctt att gtg cgc ctt cct gat       924
Ser Gly Gly Leu Gly Leu Gln Leu Pro Leu Ile Val Arg Leu Pro Asp
        115                 120                 125 gtg ctt aag aac cgt ttg gag tct ctc caa tcg gca ttt gat tgt gct       972
Val Leu Lys Asn Arg Leu Glu Ser Leu Gln Ser Ala Phe Asp Cys Ala
    130                 135                 140 att caa tct cag gga tat ggg tct cat tac cag ggc gtt tat ccg gtc      1020
Ile Gln Ser Gln Gly Tyr Gly Ser His Tyr Gln Gly Val Tyr Pro Val
145                 150                 155                 160 aaa tgc aac cag gac agg ttc gtt gtt gaa gac atc gtg aaa ttc ggt      1068
Lys Cys Asn Gln Asp Arg Phe Val Val Glu Asp Ile Val Lys Phe Gly
                165                 170                 175 tct cct ttc cgt ttc ggt ctc gag gct gga tcg aaa ccg gag ctc ctc      1116
Ser Pro Phe Arg Phe Gly Leu Glu Ala Gly Ser Lys Pro Glu Leu Leu
            180                 185                 190 ctg gca atg agc tgt ttg tgc aaa ggg aat aga gat gcc ctt ttg gtg      1164
```

|  |  |
|---|---|
| Leu Ala Met Ser Cys Leu Cys Lys Gly Asn Arg Asp Ala Leu Leu Val<br>            195                  200                  205 | |
| tgt aat ggt ttc aag gat gcg gag tac att tct ctg gct ctt att gct<br>Cys Asn Gly Phe Lys Asp Ala Glu Tyr Ile Ser Leu Ala Leu Ile Ala<br>210                  215                  220 | 1212 |
| agg aag ctc gct ttg aac act gtg att gtg ctt gaa caa gag gaa gag<br>Arg Lys Leu Ala Leu Asn Thr Val Ile Val Leu Glu Gln Glu Glu Glu<br>225                  230                  235                  240 | 1260 |
| ctt gat ttg gtt atc gat ttg agt aaa acg ctc ttc gtt cgc cct gtg<br>Leu Asp Leu Val Ile Asp Leu Ser Lys Thr Leu Phe Val Arg Pro Val<br>            245                  250                  255 | 1308 |
| atc ggc atg cgt gcg aag cta aga acc aag cat tct ggt cat ttt ggg<br>Ile Gly Met Arg Ala Lys Leu Arg Thr Lys His Ser Gly His Phe Gly<br>                260                  265                  270 | 1356 |
| tct aca tca ggc gag aaa ggg aaa ttt ggt ctt acg acc aca caa att<br>Ser Thr Ser Gly Glu Lys Gly Lys Phe Gly Leu Thr Thr Thr Gln Ile<br>            275                  280                  285 | 1404 |
| ctt cgt gtg gtt agg aag ctt aaa cag gct gat atg ctt gat tgt ctt<br>Leu Arg Val Val Arg Lys Leu Lys Gln Ala Asp Met Leu Asp Cys Leu<br>290                  295                  300 | 1452 |
| caa ttg ctc cat ttt cat att ggt tcc cag atc ccc tcc acc gtg tta<br>Gln Leu Leu His Phe His Ile Gly Ser Gln Ile Pro Ser Thr Val Leu<br>305                  310                  315                  320 | 1500 |
| ctc acc gat ggc att agc gag gct gct caa atc tat tgt gaa ttg gtt<br>Leu Thr Asp Gly Ile Ser Glu Ala Ala Gln Ile Tyr Cys Glu Leu Val<br>                325                  330                  335 | 1548 |
| cgt ctc ggt gcc aac atg cta gtt att gac att gga ggt ggt ctt ggt<br>Arg Leu Gly Ala Asn Met Leu Val Ile Asp Ile Gly Gly Gly Leu Gly<br>            340                  345                  350 | 1596 |
| atc gac tat gac ggg tcg aag tca ggg gat tct gag tta tct gtt gct<br>Ile Asp Tyr Asp Gly Ser Lys Ser Gly Asp Ser Glu Leu Ser Val Ala<br>            355                  360                  365 | 1644 |
| tat gaa ctc gga gag tat gcc tct acg gtt gtt gat gca gtc cgc tgt<br>Tyr Glu Leu Gly Glu Tyr Ala Ser Thr Val Val Asp Ala Val Arg Cys<br>370                  375                  380 | 1692 |
| gta tgc gac cgt agg gcc gtt aag cac ccg ata att tgc agt gaa agt<br>Val Cys Asp Arg Arg Ala Val Lys His Pro Ile Ile Cys Ser Glu Ser<br>385                  390                  395                  400 | 1740 |
| ggc cga gca atc gtc tct cat cac tct gtt ctg ata ttt gag gct gtt<br>Gly Arg Ala Ile Val Ser His His Ser Val Leu Ile Phe Glu Ala Val<br>                405                  410                  415 | 1788 |
| tct gct agt tct tat gag gtc cca tcc atg agc tcg att gaa cgt cag<br>Ser Ala Ser Ser Tyr Glu Val Pro Ser Met Ser Ser Ile Glu Arg Gln<br>            420                  425                  430 | 1836 |
| tat ctt gtc gat gga cta acc gac gat gct cgt att gat tat cag aac<br>Tyr Leu Val Asp Gly Leu Thr Asp Asp Ala Arg Ile Asp Tyr Gln Asn<br>            435                  440                  445 | 1884 |
| ctt ttg act gca gct tat atg ggt gag tac aag gcg tgc ttg cta tat<br>Leu Leu Thr Ala Ala Tyr Met Gly Glu Tyr Lys Ala Cys Leu Leu Tyr<br>450                  455                  460 | 1932 |
| gca gat caa ttg aag caa tgc tgt gtt gag aaa ttc aag gat ggg tgt<br>Ala Asp Gln Leu Lys Gln Cys Cys Val Glu Lys Phe Lys Asp Gly Cys<br>465                  470                  475                  480 | 1980 |
| ttg gga atg gaa gaa cta gct gcg gta gat ggg ctt tgt gcc ctt gtt<br>Leu Gly Met Glu Glu Leu Ala Ala Val Asp Gly Leu Cys Ala Leu Val<br>                485                  490                  495 | 2028 |
| tca aag gca att gga gag ttg gat gct gta aga act tac cat gtg aac<br>Ser Lys Ala Ile Gly Glu Leu Asp Ala Val Arg Thr Tyr His Val Asn<br>            500                  505                  510 | 2076 |
| ctc tcc att ttc acc tct atc cca gat ttc tgg ggt att gac cag ctg | 2124 |

```
              Leu Ser Ile Phe Thr Ser Ile Pro Asp Phe Trp Gly Ile Asp Gln Leu
                  515                 520                 525 ttt cca att gtc cct att cat cgt ctc gat caa aga ccg tca gtg agg          2172
Phe Pro Ile Val Pro Ile His Arg Leu Asp Gln Arg Pro Ser Val Arg
530                 535                 540 ggc att cta tcc gat cta acc tgt gac agt gac ggt aag atc gat agg          2220
Gly Ile Leu Ser Asp Leu Thr Cys Asp Ser Asp Gly Lys Ile Asp Arg
545                 550                 555                 560 ttt atc aat ggc gag tcg agc ttg ccg ttg cat gag ctc aaa ggc aac          2268
Phe Ile Asn Gly Glu Ser Ser Leu Pro Leu His Glu Leu Lys Gly Asn
                565                 570                 575 agc agt tta tca ggt gga ggt ggg cga tac tat ctt ggg atg ttt cta          2316
Ser Ser Leu Ser Gly Gly Gly Gly Arg Tyr Tyr Leu Gly Met Phe Leu
            580                 585                 590 ggt ggg gct tat gag gag gct ctc ggt ggt gtt cac aac ctg ttt ggg          2364
Gly Gly Ala Tyr Glu Glu Ala Leu Gly Gly Val His Asn Leu Phe Gly
        595                 600                 605 agc ccg agc gtg att cgg gta atg cag agc gat gga ccg cat agc ttt          2412
Ser Pro Ser Val Ile Arg Val Met Gln Ser Asp Gly Pro His Ser Phe
    610                 615                 620 gcg gtg act cgc act gtg cct ggg cca tca tgt gcg gat atc ctc cga          2460
Ala Val Thr Arg Thr Val Pro Gly Pro Ser Cys Ala Asp Ile Leu Arg
625                 630                 635                 640 gtg atg cag tac gag ccc gag ctc atg ttt gag acc ctc aag cat cga          2508
Val Met Gln Tyr Glu Pro Glu Leu Met Phe Glu Thr Leu Lys His Arg
                645                 650                 655 gct gag gag ttt ggg cag gag gag gag gat gat gtt gga ggc att gcc          2556
Ala Glu Glu Phe Gly Gln Glu Glu Glu Asp Asp Val Gly Gly Ile Ala
            660                 665                 670 aat agc ttg gcc atg tcc ttc cgc aac atg cct tat ttg gct agc gca          2604
Asn Ser Leu Ala Met Ser Phe Arg Asn Met Pro Tyr Leu Ala Ser Ala
        675                 680                 685 tct tcc tgc gcc aat ggt gct ggc gat gcc gag cag tgg act tac tgc          2652
Ser Ser Cys Ala Asn Gly Ala Gly Asp Ala Glu Gln Trp Thr Tyr Cys
    690                 695                 700 tat gct tga tgaataatgt ttgaaggttt agtcgttagc cacatccta                   2701
Tyr Ala
705 aataagctat tggtctgttt tcgttgtcgt ggtcgtcgtc gtcgtaggtc cgtcaaccct        2761 ttttttttc ttctttggct tgttgcaaag ggttatgaga gcacagcaac agcagccaag         2821 ctcctcttcc tttggcttta ttttgttta gataggagag gggattagta gaacaccgaa         2881 tccacccttt tgttaattcg ggatcttgat ctctcttggt tatatcatgg tgtacaactt       2941 ttaagaagcc gtcaatggct gttttctttt tagatctcaa ctttggatgg ctcaaccca         3001 cttcgaatta taaaaaaaaa aaaaaaaaaa aaaaaa                                  3037

<210> SEQ ID NO 6
<211> LENGTH: 706
<212> TYPE: PRT
<213> ORGANISM: Cucurbita ficifolia

<400> SEQUENCE: 6

Met Pro Ala Leu Ala Tyr Cys Val Glu Ala Ala Ala Pro Pro Pro
1               5                   10                  15

Gly Cys Ala Phe Ala Gly Asp Ser Ser Leu Pro Ser Pro Val Leu Phe
                20                  25                  30

Ser Gly Gly Pro Pro Glu Thr Thr Ile Phe Thr Ser Pro Ala Ala Ala
            35                  40                  45
```

```
Pro Ile Ser Glu Asn Pro Ser Trp Ser Pro Ser Leu Ser Ser Leu
 50                  55                  60

Tyr Lys Ile Asp Gly Trp Gly Ala Pro Tyr Phe Ser Val Asn Gly Ser
 65                  70                  75                  80

Gly Asn Met Ala Val Arg Pro Tyr Gly Thr Ala Thr Leu Pro His Gln
                 85                  90                  95

Glu Ile Asp Leu Leu Lys Ile Val Lys Lys Ala Ser Asp Pro Ile Ser
            100                 105                 110

Ser Gly Gly Leu Gly Leu Gln Leu Pro Leu Ile Val Arg Leu Pro Asp
        115                 120                 125

Val Leu Lys Asn Arg Leu Glu Ser Leu Gln Ser Ala Phe Asp Cys Ala
130                 135                 140

Ile Gln Ser Gln Gly Tyr Gly Ser His Tyr Gln Gly Val Tyr Pro Val
145                 150                 155                 160

Lys Cys Asn Gln Asp Arg Phe Val Val Glu Asp Ile Val Lys Phe Gly
                165                 170                 175

Ser Pro Phe Arg Phe Gly Leu Glu Ala Gly Ser Lys Pro Glu Leu Leu
            180                 185                 190

Leu Ala Met Ser Cys Leu Cys Lys Gly Asn Arg Asp Ala Leu Leu Val
        195                 200                 205

Cys Asn Gly Phe Lys Asp Ala Glu Tyr Ile Ser Leu Ala Leu Ile Ala
210                 215                 220

Arg Lys Leu Ala Leu Asn Thr Val Ile Val Leu Glu Gln Glu Glu Glu
225                 230                 235                 240

Leu Asp Leu Val Ile Asp Leu Ser Lys Thr Leu Phe Val Arg Pro Val
                245                 250                 255

Ile Gly Met Arg Ala Lys Leu Arg Thr Lys His Ser Gly His Phe Gly
            260                 265                 270

Ser Thr Ser Gly Glu Lys Gly Lys Phe Gly Leu Thr Thr Gln Ile
        275                 280                 285

Leu Arg Val Val Arg Lys Leu Lys Gln Ala Asp Met Leu Asp Cys Leu
290                 295                 300

Gln Leu Leu His Phe His Ile Gly Ser Gln Ile Pro Ser Thr Val Leu
305                 310                 315                 320

Leu Thr Asp Gly Ile Ser Glu Ala Ala Gln Ile Tyr Cys Glu Leu Val
                325                 330                 335

Arg Leu Gly Ala Asn Met Leu Val Ile Asp Ile Gly Gly Gly Leu Gly
            340                 345                 350

Ile Asp Tyr Asp Gly Ser Lys Ser Gly Asp Ser Glu Leu Ser Val Ala
        355                 360                 365

Tyr Glu Leu Gly Glu Tyr Ala Ser Thr Val Val Asp Ala Val Arg Cys
370                 375                 380

Val Cys Asp Arg Arg Ala Val Lys His Pro Ile Ile Cys Ser Glu Ser
385                 390                 395                 400

Gly Arg Ala Ile Val Ser His His Ser Val Leu Ile Phe Glu Ala Val
                405                 410                 415

Ser Ala Ser Ser Tyr Glu Val Pro Ser Met Ser Ser Ile Glu Arg Gln
            420                 425                 430

Tyr Leu Val Asp Gly Leu Thr Asp Asp Ala Arg Ile Asp Tyr Gln Asn
        435                 440                 445

Leu Leu Thr Ala Ala Tyr Met Gly Glu Tyr Lys Ala Cys Leu Leu Tyr
450                 455                 460

Ala Asp Gln Leu Lys Gln Cys Cys Val Glu Lys Phe Lys Asp Gly Cys
465                 470                 475                 480
```

-continued

```
Leu Gly Met Glu Glu Leu Ala Ala Val Asp Gly Leu Cys Ala Leu Val
                485                 490                 495
Ser Lys Ala Ile Gly Glu Leu Asp Ala Val Arg Thr Tyr His Val Asn
            500                 505                 510
Leu Ser Ile Phe Thr Ser Ile Pro Asp Phe Trp Gly Ile Asp Gln Leu
        515                 520                 525
Phe Pro Ile Val Pro Ile His Arg Leu Asp Gln Arg Pro Ser Val Arg
    530                 535                 540
Gly Ile Leu Ser Asp Leu Thr Cys Asp Ser Asp Gly Lys Ile Asp Arg
545                 550                 555                 560
Phe Ile Asn Gly Glu Ser Ser Leu Pro Leu His Glu Leu Lys Gly Asn
                565                 570                 575
Ser Ser Leu Ser Gly Gly Gly Arg Tyr Tyr Leu Gly Met Phe Leu
            580                 585                 590
Gly Gly Ala Tyr Glu Glu Ala Leu Gly Gly Val His Asn Leu Phe Gly
        595                 600                 605
Ser Pro Ser Val Ile Arg Val Met Gln Ser Asp Gly Pro His Ser Phe
    610                 615                 620
Ala Val Thr Arg Thr Val Pro Gly Pro Ser Cys Ala Asp Ile Leu Arg
625                 630                 635                 640
Val Met Gln Tyr Glu Pro Glu Leu Met Phe Glu Thr Leu Lys His Arg
                645                 650                 655
Ala Glu Glu Phe Gly Gln Glu Glu Asp Asp Val Gly Gly Ile Ala
            660                 665                 670
Asn Ser Leu Ala Met Ser Phe Arg Asn Met Pro Tyr Leu Ala Ser Ala
        675                 680                 685
Ser Ser Cys Ala Asn Gly Ala Gly Asp Ala Glu Gln Trp Thr Tyr Cys
    690                 695                 700
Tyr Ala
705
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 7
gttttggatg gagtgattca                                                  20

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 8
gtgaatctca gcgttgta                                                    18

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 9
tatgtgctgt ctgagtcgag c					21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 10
gctaaaccca tcttcagggg t					21

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 11
gggctkggar tsgactay					18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 12
yccrtcrctg tcrcasgt					18

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 13
tagtagaggg attattatgt ctgcgga				27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 14
atgacgctga tcacaatata aagcgac				27

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 15
tgaaggctat gaaagaggc ttgaagta				28

<210> SEQ ID NO 16
<211> LENGTH: 26
<212> TYPE: DNA
<213> ORGANISM: Artificial Sequence
<220> FEATURE:

-continued

```
<223> OTHER INFORMATION: Description of Artificial Sequence:primer

<400> SEQUENCE: 16
tcatgaggat tgaccttggg atgacg                                          26
```